(12) United States Patent
Otsuka et al.

(10) Patent No.: US 10,676,783 B2
(45) Date of Patent: Jun. 9, 2020

(54) ANALYSIS CHIP

(71) Applicant: Toray Industries, Inc., Tokyo (JP)

(72) Inventors: Hiroki Otsuka, Kamakura (JP); Yoji Ueda, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 208 days.

(21) Appl. No.: 15/561,573

(22) PCT Filed: Mar. 31, 2016

(86) PCT No.: PCT/JP2016/060840
§ 371 (c)(1),
(2) Date: Sep. 26, 2017

(87) PCT Pub. No.: WO2016/159324
PCT Pub. Date: Oct. 6, 2016

(65) Prior Publication Data
US 2018/0087100 A1    Mar. 29, 2018

(30) Foreign Application Priority Data

Mar. 31, 2015 (JP) .................................. 2015-072737
Dec. 25, 2015 (JP) .................................. 2015-255380

(51) Int. Cl.
*C12Q 1/6837* (2018.01)
*G01N 35/02* (2006.01)
(Continued)

(52) U.S. Cl.
CPC .......... *C12Q 1/6837* (2013.01); *B01L 3/5088* (2013.01); *C12Q 1/6825* (2013.01);
(Continued)

(58) Field of Classification Search
CPC .... C12Q 1/6837; C12Q 1/6825; G01N 35/02; G01N 37/00; B01L 3/5088;
(Continued)

(56) References Cited

U.S. PATENT DOCUMENTS 8,309,035 B2 * 11/2012 Chen .................. C07K 16/2896
                                                              422/407
9,310,362 B2    4/2016 Muraguchi et al.
(Continued)

FOREIGN PATENT DOCUMENTS

CN      1591012 A      3/2005
CN      1882838 A     12/2006
(Continued)

OTHER PUBLICATIONS

The First Office Action dated Jul. 1, 2019, of counterpart Chinese Application No. 201680017553.5, along with an English translation.
(Continued)

*Primary Examiner* — Samuel P Siefke
*Assistant Examiner* — Quocan B Vo
(74) *Attorney, Agent, or Firm* — DLA Piper LLP (US)

(57) ABSTRACT

An analysis chip includes a substrate main body having a plurality of reaction portions in which a selective binding substance selectively binding to a substance to be examined is immobilized; a corner portion in which different straight lines or curved lines intersect with each other in a cross section in which a plane passing through a surface of the substrate main body on which the reaction portions are provided is a cut surface; a partition portion formed by applying water repellent treatment to the surface of the substrate main body on which the reaction portions are provided, the partition portion being configured to partition the reaction portions inside an outer edge formed by the surface, and a connection portion having water repellency, the connection portion being configured to connect between a part of the partition portion and the corner portion.

20 Claims, 51 Drawing Sheets

(51) Int. Cl.
*G01N 37/00* (2006.01)
*B01L 3/00* (2006.01)
*C12Q 1/6825* (2018.01)

(52) U.S. Cl.
CPC ............ *G01N 35/02* (2013.01); *G01N 37/00* (2013.01); *B01L 2200/141* (2013.01); *B01L 2300/0819* (2013.01); *B01L 2300/161* (2013.01); *B01L 2300/165* (2013.01)

(58) Field of Classification Search
CPC ........ B01L 2300/161; B01L 2200/141; B01L 2300/165; B01L 2300/0819
See application file for complete search history.

(56) References Cited

U.S. PATENT DOCUMENTS

| | | | | |
|---|---|---|---|---|
| 2002/0192600 | A1* | 12/2002 | Okamura | B01J 19/0046 430/320 |
| 2005/0064482 | A1 | 3/2005 | Mino | |
| 2005/0214841 | A1 | 9/2005 | Nakamura | |
| 2008/0014631 | A1* | 1/2008 | Muraguchi | G01N 33/54366 435/288.7 |
| 2009/0042734 | A1* | 2/2009 | Yoshida | B01J 19/0046 506/9 |
| 2014/0004539 | A1* | 1/2014 | Simon | G01N 33/5306 435/7.92 |
| 2014/0287423 | A1 | 9/2014 | Nurse | |

FOREIGN PATENT DOCUMENTS

| | | |
|---|---|---|
| JP | 2003-14760 A | 1/2003 |
| JP | 2004-515776 A | 5/2004 |
| JP | 2007-529015 A | 10/2007 |
| JP | 4856057 B2 | 11/2011 |
| WO | 02/48676 A2 | 6/2002 |
| WO | 2005/069001 A1 | 7/2005 |
| WO | 2005/089945 A1 | 9/2005 |
| WO | 2006/101229 A1 | 9/2006 |
| WO | 2013/063230 A1 | 5/2013 |

OTHER PUBLICATIONS

Extended Search Report dated Aug. 22, 2018, of counterpart European Patent Application No. 16773204.9.
Notice of Reasons for Refusal dated Feb. 4, 2020, of counterpart Japanese Application No. 2016-521811, along with an English translation.

* cited by examiner

ANALYSIS CHIP

TECHNICAL FIELD

This disclosure relates to an analysis chip having a plurality of reaction portions.

BACKGROUND

An analysis chip having a substrate on which a selective binding substance such as genes, proteins, lipids, sugars or the like selectively binding to a substance to be examined is immobilized and in which the selective binding substance on the substrate is reacted with a sample to analyze the presence/absence, the state, or the amount of the substance to be examined contained in the sample has been known. As such a substrate, substrates made of glasses, metals, or plastics have been generally used.

As one aspect of the analysis chip, there is a microarray in which molecules such as DNA, proteins, sugar chains or the like are arranged on a substrate at high density to simultaneously measure a large number of gene expression of several hundreds to several tens of thousands. Use of the microarray enables detection and quantification of nucleic acids based on a hybridization reaction between nucleic acids/nucleic acids and detection and quantification of proteins or sugar chains based on specific reactions between proteins/proteins, between sugar chains/sugar chains, or between sugar chains/proteins. For example, the use of the microarrays allows systematic and comprehensive gene expression analysis in various disease animal models and cell biological phenomena to be carried out. Specifically, the use of the microarrays allows the function of gene, that is, the protein encoded by the gene to be clarified and the time when the protein is expressed and the site where the protein is affected to be specified. Searches for disease genes and treatment-related genes and searches for therapeutic methods can be carried out by analyzing variations in gene expression at the cell or tissue level of an organism using the microarray and constructing a gene expression profile database in combination with physiological, cell biological, and biochemical phenomenon data.

Among analysis chips, a DNA chip (or a DNA microarray) in which DNA is arranged on a substrate is used for nucleic acid detection, quantification and the like based on a hybridization reaction between nucleic acids/nucleic acids. As the DNA chip, a DNA chip in which a large number of DNA fragments are aligned and immobilized, for example, on a plane substrate made of glass at high density is used. The DNA chip is used to detect each gene or measure the amount of each of the genes in a sample. For example, the DNA chip is used at the time of measurement using a method of hybridizing a sample in which the expression gene of research target cells is labeled with a fluorescent dye or the like on a flat substrate and binding nucleic acids (DNA or RNA) complementary to each other to rapidly read the fluorescent light at the site by a high resolution detection apparatus (a scanner) or a method of detecting responses such as electric current values based on an electrochemical reaction. In addition, the DNA chip is highly expected to be applied not only to gene expression analysis by detecting and quantifying expressed genes but also in application fields such as detection of the single nucleotide polymorphism (SNP) of genes.

In addition, the analysis chip is used as an inspecting and analyzing means for not only the nucleic acid such as DNA, but also proteins, saccharides and the like. In particular, proteins such as antibodies, antigens, enzyme substrates and the like are immobilized on a substrate in an analysis chip for protein.

In recent years, efforts to realize inspection and diagnosis by genes and proteins have been actively carried out using analysis chips including the above DNA chip. When the analysis chips are used for mass screening such as health checks and comprehensive medical examinations, the number of samples to be processed becomes enormous and thus a system capable of measuring a large number of samples at a time is essential. For this reason, development of an analysis chip capable of inspecting a plurality of samples with one chip has been developed.

In a reaction step carried out after a sample is dropped, for example, when the sample spills out from the reaction portion, the spilled sample may cause contamination with the adjacent reaction portions in the analysis chip having a plurality of reactive portions to which the selective binding substance is immobilized. To solve this problem, an analysis chip in which the sample contamination to the adjacent reaction portions is avoid by surrounding and partitioning the outer periphery of each of the reaction portions with a water repellent material has been devised (for example, refer to Japanese Patent No. 4856057).

Specifically, JP '057 discloses a probe array in which a detachable sheet-like separator partially having a water repellent region is provided to prevent the sample contamination among adjacent reaction portions. As a reason for the detachment, it is described that the chemical properties of the substrate surface can be uniformly retained by attaching a separator after treating the substrate surface. The separator can be detached at the time of washing and signal detection.

As described above, the analysis chip in which the outer periphery of the reaction portion is partitioned by the water repellent material can avoid sample contamination to the adjacent reaction portions. On the other hand, in the analysis chip, a labeled substance that is unreacted (unreacted labeled substance) having strong hydrophobicity may adhere to the water repellent material after the reaction. In JP '057, a large amount of the unreacted labeled substance adheres to the separator because the entire surface of the analysis chip surface other than the reaction portions is a water repellent surface due to a sheet-like separator. In general, the analysis chip is washed by immersing the analysis chip into a washing liquid one time or more times and thus a large amount of the unreacted labeled substance adhering to the chip is in a state of being floated in the washing liquid after the immersion when the analysis chip is treated in the subsequent washing process in a state where a large amount of the unreacted labeled substance adheres. When the analysis chip immersed in the washing liquid is taken out, the unreacted labeled substance does not adhere to the separator because the washing liquid on the separator runs out, while the washing liquid containing the unreacted labeled substance remains on the reaction portions having hydrophilicity without running out. The unreacted labeled substance remaining on the reaction portions remains in the reaction portion in a dried state after the subsequent centrifugal drying process and the remaining unreacted labeled substance may act as background noise at the time of inspection. Therefore, an analysis chip capable of reducing generation of the background noise due to the remaining unreacted labeled substance and obtaining accurate analysis result is desired.

It could therefore be helpful to provide an analysis chip capable of reducing generation of the background noise generated after washing.

SUMMARY

We discovered an analysis chip capable of reducing generation of background noise affecting the data by not leaving the unreacted labeled substance on the water repellent surface of the outer periphery of the reaction portion, the analysis chip being useful for inspection and diagnosis.

Our analysis chip thus includes: a substrate main body having a plurality of reaction portions in which a selective binding substance selectively binding to a substance to be examined is immobilized; a corner portion in which different straight lines or curved lines intersect with each other in a cross section in which a plane passing through a surface of the substrate main body on which the reaction portions are provided is a cut surface; a partition portion formed by applying water repellent treatment to the surface of the substrate main body on which the reaction portions are provided, the partition portion being configured to partition the reaction portions inside an outer edge formed by the surface, and a connection portion having water repellency, the connection portion being configured to connect between a part of the partition portion and the corner portion.

The corner portion is the outer edge of the surface of the substrate main body, and the connection portion has one extension portion or a plurality of extension portions formed by applying water repellent treatment to the surface of the substrate main body on which the reaction portions are provided and extending from a part of the partition portion to at least a part of the corner portion.

The substrate main body has a rectangular shape formed by the outer edge, and the extension portion is in contact with a part of one edge side out of four sides of the outer edge.

The substrate main body has a rectangular shape formed by the outer edge, and the plurality of extension portions are in contact with a part of different edge sides from each other out of four edge sides of the outer edge.

The analysis chip further includes an indicator portion indicating a position of the extension portion.

The connection portion is a cutout portion being a part of the substrate main body, formed by cutting out a region from the outer edge of the substrate to the partition portion, and having the corner portion.

The analysis chip further includes a projection portion connected to a water repellent surface of the partition portion, the projection portion being configured to project from the substrate main body. The corner portion is formed from a side surface along a projecting direction of the projecting portion by at least a top surface of the projection portion in the projecting direction and the side surface, the side surface being connected to the partition portion; and a projecting length of the top surface of the projection portion from the substrate main body is longer than a protruding length of the water repellent surface of the partition portion from the substrate main body.

The connection portion has one extension portion or a plurality of extension portions formed by applying water repellent treatment to the surface of the substrate main body on which the reaction portions are provided, extending from a part of the partition portion toward the outer edge of the substrate main body, and connected to the corner portion at an end portion of the projection portion opposite to an end portion of the projection portion connected to the partition portion; and the projection portion is connected to the water repellent surface of the partition portion via the extension portion and includes one or more projection portions depending on number of the extension portion(s).

The projection portion is provided adjacent to a part of the partition portion.

The partition portion has a rectangular shape formed by the outer edge; the projection portion is in contact with a linear portion in the outer edge; and the connection portion is integrally provided with the projection portion.

The partition portion has a rectangular shape formed by the outer edge; the projection portion is in contact with a corner portion in the outer edge; and the connection portion is integrally provided with the projection portion.

The projection portion comprises a sheet-like member.

The projection portion is integrally formed with the substrate main body.

The analysis chip further includes a recessed portion having one end connected to a water repellent surface of the partition portion and having a recessed shape in the cross section of the substrate main body. The corner portion is formed by an end of an opening of the recessed portion.

The connection portion has one extension portion or a plurality of extension portions formed by applying water repellent treatment to the surface of the substrate main body on which the reaction portions are provided, extending from a part of the partition portion toward the outer edge of the substrate main body, and connected to a part of the opening of the recessed portion at an end portion of the recessed portion opposite to an end portion of the recessed portion connected to the partition portion; and the recessed portion is connected to the water repellent surface of the partition portion via the extension portion and includes one or more recessed portions depending on number of the extension portion(s).

The extension portion is connected to the water repellent surface of the partition portion and includes a water repellent surface extending from a part of a side that is a side surface of the recessed portion along a depression direction of the recessed portion and that is connected to the partition portion to a part of a side surface of the recessed portion different from the side via a bottom surface of the recessed portion in the depression direction of the recessed portion.

The extension portion is configured to form a part of the partition portion.

The partition portion is configured to independently partition each of the reaction portions.

The partition portion is configured to partition the reaction portions as each set of a plurality of reaction portions.

The reaction portion has a recessed shape with respect to the surface of the substrate main body.

Generation of the background noise affecting the data can be reduced by not leaving the unreacted labeled substance on the water repellent surface of the outer periphery of the reaction portion at the time of washing. Therefore, a substance to be examined contained in a sample can be accurately detected or quantified by analyzing it with the use of the analysis chip.

REFERENCE SIGNS LIST 1, 1a to 1p, 2, 3, 4, 5, 100, 100a to 100r, 110, 200, 200a, 300, 400 Analysis Chip
10, 10a, 10A, 10d, 10e, 10f, 20, 40, 50, 700 Substrate
10b, 10d, 10e, 10f Main Body Portion
10c, 71-76 Projection Portion
11, 21, 41, 51 Reaction Portion
12, 12a to 12i, 22, 42, 52, 701 Partition Portion
13, 13a to 13d, 15, 15a, 15b, 16, 16a, 16b, 17, 17a, 23, 43, 61, 61a, 61b, 62, 62a, 62b, 63, 63a, 64, 64a, 65, 91, 93, 94 Extension Portion
14 Indicator Portion
18 Cutout Portion
81 Recessed Portion
100 Analysis Chip
121, 125, 126 Surrounding Portion
122 Coupling Portion
123 Outer Peripheral Portion
124 Second Coupling Portion
500 Sample Plate
501 Well
600 Container
601 Washing Liquid
$C_1$-$C_{13}$ Corner Portion

DETAILED DESCRIPTION

Hereinafter, construction/examples will be described in detail with reference to the drawings. This disclosure, however, is not limited to the following construction/examples. In addition, each of the drawings referred to in the following description only schematically illustrates a shape, a size, and a positional relation to the extent that the contents can be understood. In other words, our chips are not limited only to the shape, the size, and the positional relation exemplified in each of the drawings. In addition, in the description of the drawings, the same reference signs are assigned to the same parts.

The analysis chip is used to measure the presence or absence, the amount, the properties and the like of the substance to be examined by dropping a sample to the reaction portion of the analysis chip. Specifically, examples of the analysis chip include a biochip that measures the presence or absence, the amount and the like of the substance to be examined by a reaction of a selective binding substance immobilized on the surface of a carrier and a substance to be examined. More specifically, the examples of the analysis chip include a DNA chip in which a nucleic acid is immobilized on the surface of a carrier, a protein chip in which a protein represented by an antibody is immobilized on the surface of a carrier, a sugar chain chip in which a sugar chain is immobilized on the surface of a carrier, and a cell chip in which cells are immobilized on the surface a carrier.

First Construction

Figure 1:
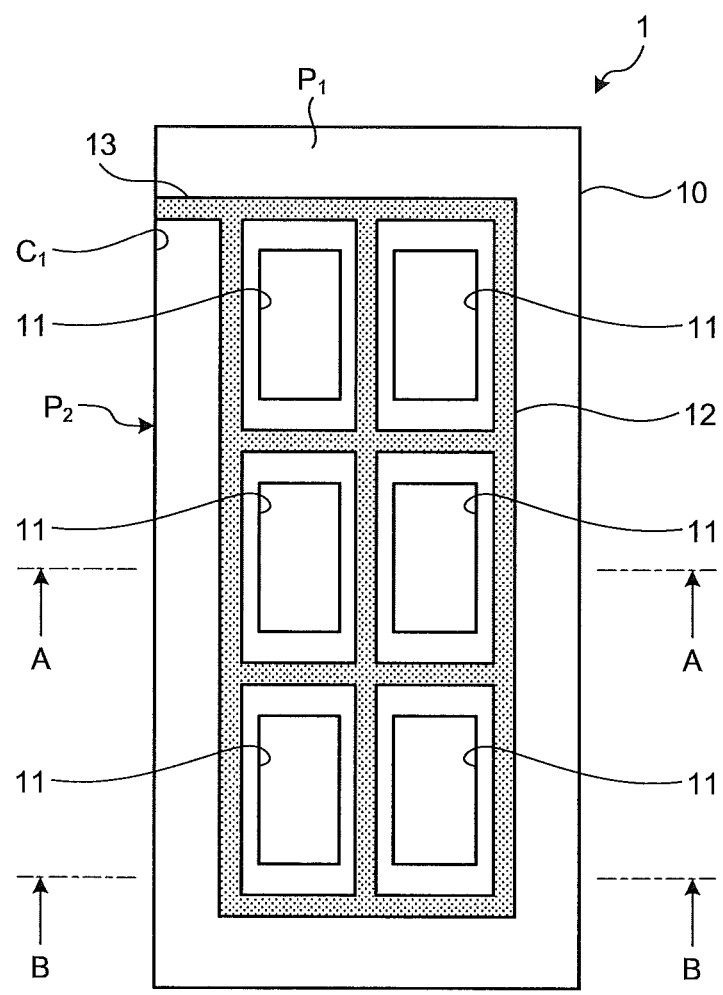
FIG. 1 is a plan view schematically illustrating an analysis chip according to a first construction.
Figure 2:
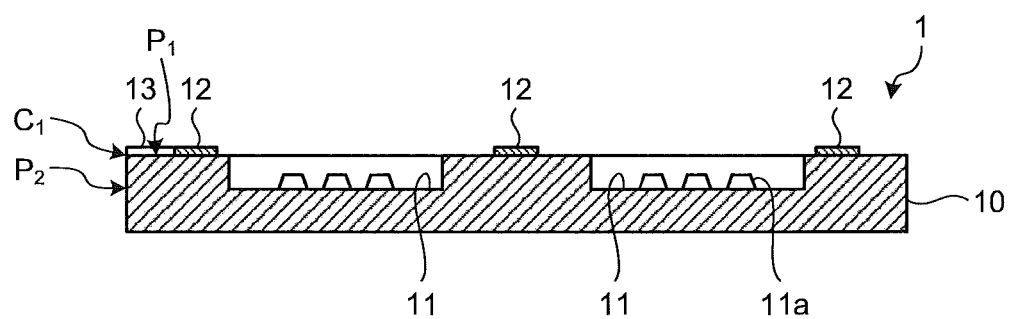
FIG. 2 is a cross-sectional view taken along the line A-A of FIG. 1.

An analysis chip according to a first construction will be described with reference to FIGS. 1 and 2. FIG. 1 is a plan view schematically illustrating an analysis chip according to the first construction. FIG. 2 is a cross-sectional view taken along the line A-A of FIG. 1. The analysis chip 1 illustrated in FIGS. 1 and 2 includes a substrate 10 having a plurality of reaction portions 11, a partition portion 12, and an extension portion 13 being a connection portion.

The substrate 10 is made of a flat plate (substrate main body) having a rectangular main surface. The main surface means a surface having the largest area. The material of the substrate 10 is preferably glass or various polymers (for example, polystyrene, polymethyl methacrylate, polycarbonate, and polyolefin). The material, however, is not particularly limited. The substrate 10 is preferably made of a material capable of reducing autofluorescence and, for example, at least a part of the protrusion portion to which the selective binding substance is immobilized is preferably black. In addition, the substrate 10 has hydrophilicity at least at the main surface on which the reaction portions 11 are formed. To impart hydrophilicity, the substrate 10 may be formed using a material having hydrophilicity or a material having hydrophilicity may be applied onto the surface of the substrate 10.

The reaction portions 11 having a recessed shape are formed on one main surface of the substrate 10. The reaction portion 11 is a place (or a region) where the substance to be examined and the selective binding substance are specifically binded. The reaction portion 11 is formed of a bottom surface and wall surfaces connecting the bottom surface and the main surface of the substrate 10. The selective binding substance is immobilized in the hollow space formed by the bottom surface and the wall surfaces. The reaction portion 11 has a plurality of protrusion portions 11a protruding from the bottom surface in a protruding shape. The selective binding substance is immobilized on the top surface of the protrusion portions 11a. In addition, the bottom surface and the wall surfaces of the reaction portion 11 preferably have hydrophilicity.

The selective binding substance means various substances capable of selectively binding directly or indirectly to the substance to be examined. Representative examples of the selective binding substance capable of binding to the substance to be examined include nucleic acids, proteins, peptides, saccharides, and lipids.

Among the selective binding substance, examples of nucleic acids include DNA and RNA and may include PNA and LNA. Usable examples of DNA include chromosomal DNA, viral DNA, DNA of bacteria, fungi and the like, cDNA obtained by reverse transcription of RNA, and fragments of a part of these DNAs. The usable examples, however, are not limited to these DNAs and fragments. In addition, usable examples of RNA include messenger RNA, ribosomal RNA, small RNA, microRNA, and fragment of a part these RNAs. The usable examples, however, are not limited to these RNAs and fragments. The nucleic acids also include chemically synthesized DNA or RNA. A single-stranded nucleic acid having a specific base sequence is selectively hybridized with a single-stranded nucleic acid having a base sequence complementary to the base sequence or a part of the base sequence to bind each other and thus the single-stranded nucleic acid corresponds to the selective binding substance referred to herein. The nucleic acid may be derived from a natural product such as a living cell or may be synthesized by a nucleic acid synthesizer. Preparation of DNA or RNA from living cells can be carried out by a known method, for example, by the method of Blin et al. (Blin et al., Nucleic Acids Res. 3: 2303 (1976)) and the like with regard to the extraction of DNA and by the method of Favaloro et al. (Favaloro et al., Methods Enzymol. 65: 718 (1980)) or the like with regard to the extraction of RNA. As the nucleic acid to be immobilized, linear or cyclic plasmid DNA or chromosomal DNA, DNA fragments obtained by cleaving these DNAs with a restriction enzyme or chemically, DNA synthesized with an enzyme and the like in a test tube, or a chemically synthesized oligonucleotide can also be used.

Examples of the proteins may include antibodies and antigen-binding fragments of antibodies such as Fab fragments and F(ab')2 fragments, and various antigens. The antibody or its antigen-binding fragment selectively binds to the corresponding antigen, and the antigen selectively binds to the corresponding antibody and thus corresponds to the selective binding sub stance.

Examples of the saccharide include sugar chains made of various monosaccharides, oligosaccharides, and polysaccharides.

As the lipids, complex lipids may be included in addition to simple lipids.

Moreover, substances having antigenicity other than the nucleic acids, proteins, saccharides, and lipids can also be immobilized. In addition, cells may be immobilized as a selective binding substance on the surface of a carrier.

Among these selective binding substances, DNA, RNA, proteins, peptides, sugars, sugar chains, and lipids are particularly preferably included.

The number of the reaction portions 11 can be set to any number such as 2, 4, 8, 12, 16, 24, 36, 48, and 96. In addition, the reaction portions 11 are arranged in a matrix. When a sample is placed in a microtiter plate or the like and the sample is dispensed to each of the reaction portions 11 using a multi-pipette having, for example, 4, 6, 8, or 12 channels, the number of reaction portions 11 is preferably the multiple number of the pipette channels, that is, for example, the multiple number of 4, the multiple number of 6, the multiple number of 8, or the multiple number of 12, respectively.

The partition portion 12 is provided on the main surface of the substrate 10 and partitions the reaction portions 11 by surrounding each of the reaction portions 11 with a water repellent material inside the outer edge formed by the main surface. The partition portion 12 surrounds the reaction portions 11 at a predetermined distance from the outer edge the reaction portions 11. The partition portion 12 extends in a strip-like shape along the outer edge of the reaction portion 11 and forms a water repellent surface having water repellent properties. As shown in FIG. 1, the partition portion 12 partitions the reaction portions 11 in a grid pattern.

The partition portion 12 is formed by, for example, coating (application) the main surface of the substrate 10 with a water repellent material. The partition formed by the partition portion 12 means a state in which the reaction portion 11 is surrounded without any gap. In the first construction, water repellent surface surrounding each of the reaction portions 11 is continuous in the partition portion 12. Water repellency means, in short, the property of repelling water and, for example, can be quantitatively indicated by the contact angle of water. The contact angle is a value obtained by quantifying the degree of wetting of a surface such that a clean glass surface is well wetted by water while a surface coated with fluorine coating repels water (for example, refer to "Nure Gijutu Handbook (Wetting Technology Handbook)," 2001, published by Techno System Co., Ltd.).

The extension portion 13 is provided on the main surface of the substrate 10 and extends from a part of the partition portion 12 to a corner portion $C_1$ formed by the outer edges (the edge sides) of the substrate 10. In FIG. 2, the corner portion $C_1$ is an angle formed by a surface $P_1$ on which the reaction portions 11 of the substrate 10 is provided and a surface $P_2$ to which the extension portion 13 extending from the partition portion 12 reaches at the shortest distance among the four side surfaces orthogonal to the surface $P_1$. The surface $P_1$ and the surface $P_2$ are cross sections of the substrate 10 and form straight lines each other in a cross section (for example, refer to FIG. 2) in which a plane passing through the surface on which the reaction portions 11 are provided is a cut surface. The corner portion $C_1$ is formed by intersecting these strait lines each other. The extension portion 13 extends in a strip-like shape and forms a water repellent surface having water repellency. The extension portion 13 is continuous with the partition portion 12. In other words, the water repellent surface of the partition portion 12 and the water repellent surface of the extension portion 13 form a continuous surface. The same water repellent material as or a different water repellent material from the material of the partition portion 12 may be used for the extension portion 13. The extension portion 13, however, is preferably formed by using the same water repellent material from the continuity of boundary surface. In addition, the extension portion 13 preferably extends linearly with respect to the partition portion 12 from the viewpoint of easily forming the water repellent surface. The water repellent surface formed of the partition portion 12 and the extension portion 13 preferably has a small occupied area to the main surface of the substrate 10 from the viewpoint of reducing the adhering amount of the unreacted labeled substance during washing. In addition, the corner portion $C_1$ preferably has an angle formed by the surface $P_1$ and the surface $P_2$ of more than 0° and less than 180°. The angle is preferably 60° or more and 120° or less and more preferably 70° or more and 110° or less in the above range. The angle is further preferably 80° or more and 100° or less. In consideration of industrially forming and processing the substrate, the angle is particularly advantageously set to 90°.

Examples of the method of forming the partition portion 12 and the extension portion 13 include a water repellent process as a surface treatment. For example, when the substrate 10 is coated with a water repellent material, examples of the method include a method of coating the substrate 10 with commercially available coating agents capable of imparting water repellency by, for example, spray coating, dip coating, dip spin coating, roll coating, spin flow coating, and coating with a brush, an ink brush, and a pen. Preferably useable examples of the commercially available coating agents capable of imparting water repellency include AsahiGuard E-SERIES (manufactured by Asahi Glass Co., Ltd.), Novec™ high performance coating agent (manufactured by 3M Japan Ltd.), SIFEL 2000 series for adhesion and coating and fluorine antifouling additive KY-100 series and KY-1200 series (manufactured by Shin-Etsu Chemical Co., Ltd.), fluorine-based ultra-thin coating MX-031 (manufactured by Surf Kogyo Co., Ltd.), NK guard S series and NEOSEED NR-90 (manufactured by Nicca Chemical Co., Ltd.), and Each series of FG-1010, FG-1060, FG-4010, FG-5040, FS-1010C, FS-1020C, FS-1030C, FS1040C, and FS-1060C (manufactured by Fluoro Technology Co., Ltd.). In addition, various water repellent coating agents for automobiles may be used or a method of applying a fine structure imitating the surface of a lotus leaf to the surface of the substrate 10 by coating or surface processing (for example, knurling) may be used.

The analysis chip is characterized in that a part of the water repellent surface (extension portion 13) described above is in contact with at least a part of the edge side on the surface of the substrate 10. Although the number of the edge sides is not particularly limited, one edge side is sufficient, that is, it is sufficient that the extension portion 13 is formed on one edge side. In addition, the number of water repellent surfaces in contact with the edge side is not particularly limited and is preferably one. In other words, a state in which one water repellent surface is in contact with the same one edge side of the substrate 10 is the most preferable aspect.

Detection noises can be reduced and a detection result having a high S/N ratio (a ratio of signal to noise) can be obtained by using the analysis chip 1 having such a structure to analyze the substance to be examined and focus the scanner on the top surfaces of the protrusion portions 11a on which the selective binding substance is immobilized at the time of signal detection.

The S/N ratio can be used as an index indicating the detection sensitivity of signals and the sensitivity is preferably determined using S/N=2 as a detection limit. Generally, the concentration or amount of the substance to be examined of which the S/N ratio is 2 to 3 is adopted as the detection limit. When the S/N ratio is 2 or more, the detection can be determined to have reliability above the detection limit (for example, Makoto Niwa, "Korenarawakaru Kagakunotameno Toukeisyuhou—Tadasii Data no Atukaikata (Statistical method for chemistry that is easy to understand—How to handle data correctly," 2008, edited by Kagaku-Dojin Publishing Company, INC., p. 101).

Figure 3:
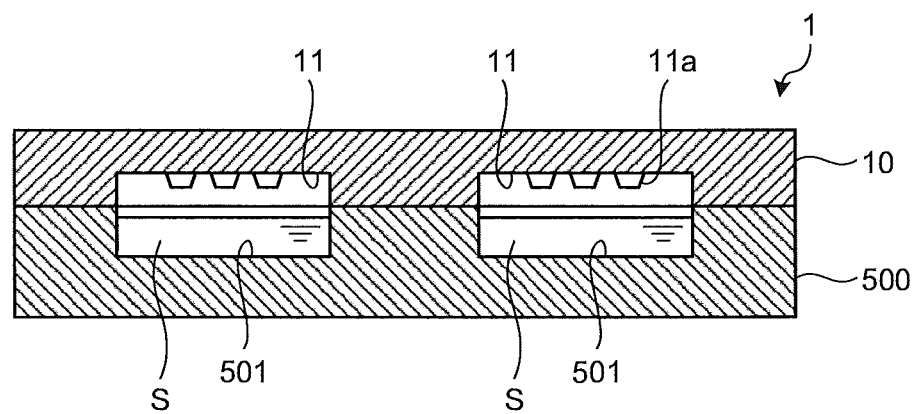
FIG. 3 is a cross-sectional view schematically illustrating the analysis chip and a sample plate when they are set according to the first construction.

Subsequently, the reaction (hybridization) process of the sample using the analysis chip 1 will be described. FIG. 3 is a cross-sectional view schematically illustrating the analysis chip and a sample plate when they are set according to the first construction. In the reaction process, first, the sample S is dropped into a well 501 provided in a sample plate 500 illustrated in FIG. 3 and the reaction portion 11 of the analysis chip 1 and the well 501 of the sample plate 500 are stacked so that they face each other. At this time, the reaction portion 11 of the analysis chip 1 is stacked above the sample plate 500 in a direction where the reaction portion 11 faces downward and fixed. The sample plate 500 is formed using an elastically deformable material. The analysis chip 1 and the sample plate 500 can be stacked in close contact with each other due to the elastic deformation of the sample plate 500.

Thereafter, the substance to be examined in the sample S and the selective binding substance immobilized on the top surface of the protrusion portions 11a are reacted by carrying out stirring treatment, for example, at 32° C. for several hours. In the stirring treatment, the sample S is stirred by moving the analysis chip 1 by rotation, vibration or the like, or a combination thereof. Examples of the rotational movement include horizontal circular movement in which the analysis chip 1 itself rotates around a rotation axis by a circular movement or an elliptical movement, revolution movement in which the analysis chip 1 revolves around the rotation axis outside the analysis chip 1, and rotation-revolution movement in which rotation and revolution are combined. In addition, a method of vibrating the analysis chip 1 itself or the sample with an ultrasonic transducer, a piezoelectric element or the like is used as the vibration. Among them, the solution is preferably stirred by the horizontal circular movement of the analysis chip 1. In the horizontal circular movement, the number of rotations may be constant or the number of rotations may be changed. The horizontal circular movement may be intermittently carried out such as stopping the movement for a certain period during the horizontal circular movement. In addition, the rotation direction is not particularly limited and may be clockwise, counterclockwise, or a combination thereof.

A stirring device that stirs the analysis chip 1 is not particularly limited as long as the device is capable of providing a centrifugal acceleration of 1×g or more in a combination of the number of rotation and the rotation radius of the horizontal circular movement. In commercially available products, plate shakers can be suitably used. Examples of the plate shakers include "BioShake 5000 elm," "BioShake 3000-T elm" and "BioShake 3000 elm" (all are manufactured by Q. Instruments GmbH.), "Monoshake," "Teleshark" and "Teleshark 1536" (all manufactured by Thermo Scientific Ltd.), "MS3 Basic," "MS3 Digital," "VXR basic Vibrax" (registered trademark), and "VORTEX 3" (all are manufactured by IKA Corporation), "Microplate Shaker N-704" (manufactured by Nissin Rika Co.), "Plate Shaker KM-M01" (manufactured by Kajixx Co., Ltd.), and "Plate Mixer P-10" (manufactured by Juji Field Inc.).

Body fluids such as blood, serum, plasma, urine, feces, cerebrospinal fluid, saliva, various tissue liquids and the like, various foods and drinks, diluted products thereof and the like are used as the solution (sample S) containing the substance to be examined. The sample S, however, is not limited thereto.

Examples of the substance to be examined include nucleic acids to be measured (target nucleic acids), for example, genes such as pathogens and viruses, causative genes of genetic diseases, and the like, and a part thereof, various biological components having antigenicity, and antibodies against pathogens, viruses and the like. The substance to be examined, however, is not limited these substances. For example, when the substance to be examined is a nucleic acid, hybridization is used for detection, while when the substance to be examined is a protein, an antigen-antibody reaction is used.

The sample S is preferably a solution in which the presence or absence, the amount, the properties and the like of the substance to be examined can be checked. Specifically, examples of the solution include solutions containing nucleic acids, antibodies, sugar chains, or the like that are recovered, extracted, and purified from bloods, tissues, cells and the like. The solution, however, is not limited to these solutions.

The nucleic acid to be the substance to be examined may be a nucleic acid labeled with a fluorescent substance or the like for nucleic acids extracted from bloods or cells or may be a nucleic acid amplified by a nucleic acid amplification method such as PCR with the nucleic acid to be the substance to be examined as a template. When a nucleic acid amplification product is used as the substance to be examined, the amplified nucleic acid can be labeled by amplifying in the presence of nucleoside triphosphate labeled with a fluorescent substance or the like. When the substance to be examined is an antigen or an antibody, the antigen or the antibody being the substance to be examined may be directly labeled by a conventional method. Alternatively, the label binded to a carrier can be measured by binding an antigen or antibody being the substance to be examined to the selective binding substance, thereafter washing the carrier, and reacting the labeled antigen or antibody with the antigen or antibody binded to the selective binding substance in an antigen-antibody reaction. In addition, when a nucleic acid which has not been amplified is used as the substance to be examined, for example, a method of reacting the substance to be examined labeled with a fluorescent substance by removing phosphoric acid group at the 5' end of the nucleic acid using alkaline phosphatase with the selective binding substance and measuring the binded label or a method of capturing the substance to be examined with the selective binding substance (a capture probe), thereafter, binding the detection probe labeled with a fluorescent substance or the like to the substance to be examined, and measuring the label of the detection probe (a sandwich hybridization method) is suitably used.

The sample S may be directly dropped on the reaction portion 11 and used. In this case, the shape of the opening of the reaction portion 11 is not particularly limited. For example, when the sample S in an amount that does not completely fill the reaction portion 11 is dropped and the dropped sample is stirred in a closed space formed by sealing with a cover or the like, the closed space preferably has a shape in which a space (or air bubbles) remaining in the reaction portion 11 that is not filled with the sample S easily moves. For example, when the outer peripheral shape of the bottom surface of the reaction portion 11 is a polygonal shape such as a quadrangular shape and a hexagonal shape, a circular shape, and an elliptical shape, the space (or the air bubbles) remaining in the reaction portion 11 easily moves (move) and thus these shapes are preferable. The cover to be used may be made of any material such as glass, various polymers (for example, polystyrene, polymethyl methacrylate, polycarbonate, and polyolefin), silicone and the like.

Figure 4:
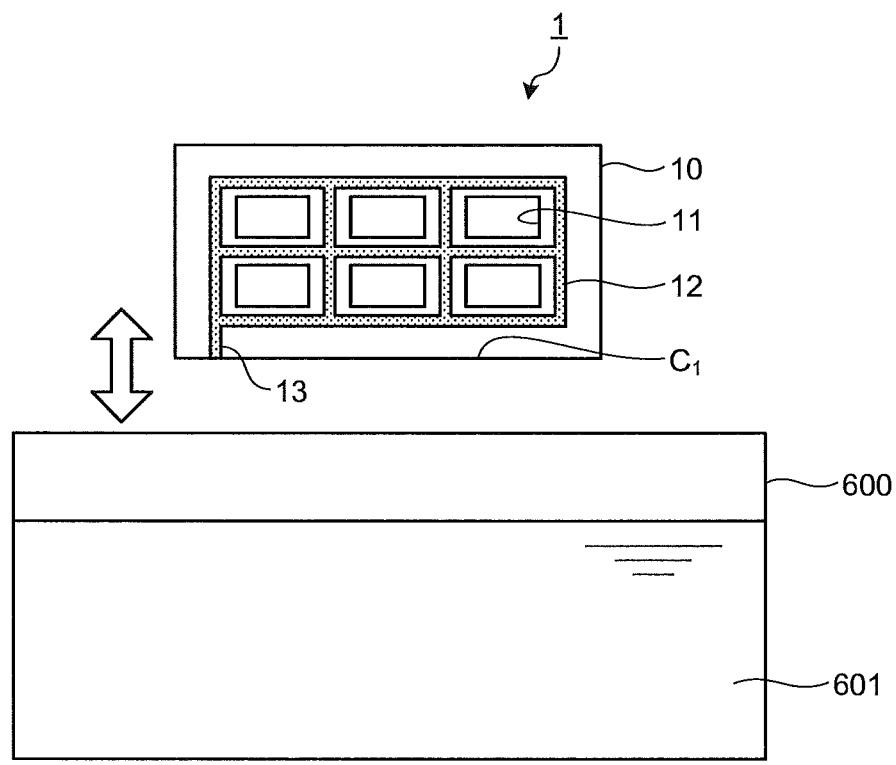
FIG. 4 is a view for illustrating the washing process of the analysis chip according to the first construction.

After the reaction treatment, the analysis chip 1 is subjected to a washing treatment to remove the labeled substance unreacted with the selective binding substance from the analysis chip 1. FIG. 4 is a view illustrating a washing process of analysis chip according to the first construction The analysis chip 1 is washed by a method in which the analysis chip 1 is entirely immersed in a washing liquid 601 filled in a container 600 or the like. In this case, for example, the analysis chip 1 is swung in the washing liquid 601 in upward, downward, rightward and leftward directions, and thereafter swing of the analysis chip 1 in upward, downward, rightward and leftward directions in the washing liquid 601 in a different container 600 is repeated several times (in several containers). In this manner, the washing process is repeated a plurality of times while replacing with a new washing liquid and, after washing, the liquid on the edge side of the analysis chip 1 runs out on a paper towel or the like. As a result, the unreacted labeled substance can be removed step by step in each container 600.

In this case, when the analysis chip 1 is pulled up from the washing liquid 601, orientation of the analysis chip 1, however, is not particularly limited. The analysis chip 1 is preferably pulled up so that the water repellent surface (the extension portion 13) in contact with the corner portion $C_1$ of the analysis chip 1 finally comes out of the liquid. The washing liquid 601 on at least the water repellent surface (the partition portion 12 and the extension portion 13) of the analysis chip 1 can efficiently run out by finally pulling the extension portion 13 out of the liquid. As a result, the unreacted labeled substance adhering to the water repellent surface can be washed off. After pulling up, as described above, the liquid runs out on a paper towel or the like and the analysis chip 1 is entirely immersed again in the container containing a new washing liquid to continue to wash or is transferred to a drying process. The edge side in contact with the water repellent surface (extension portion 13) of the analysis chip 1 is preferably brought into contact with a paper towel or the like when the liquid runs out on a paper towel or the like.

The washing liquid 601 is preferably a solution in which a surfactant is mixed in a salt-containing buffer solution. Examples of the buffer solution containing a salt include SSC (Saline Sodium Citrate buffer), PBS (Phosphate Buffered Salts), and sodium chloride aqueous solution and examples of the surfactant include SDS (Sodium Dodecyl Sulfate) and Tween (registered trademark). As the washing liquid 601 according to the first construction, a solution containing 0.5×SSC and 0.1% SDS, a solution containing 0.2×SSC and 0.1% SDS, and a solution containing 0.05× SSC are used.

Figure 5:
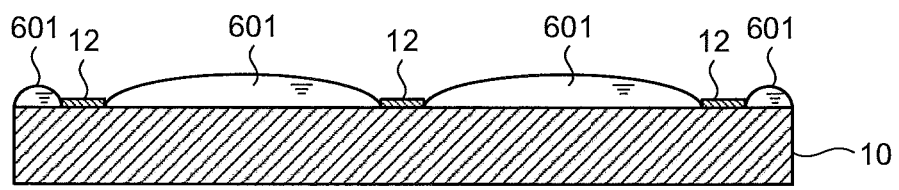
FIG. 5 is a view for illustrating a washing liquid remaining after washing of the analysis chip according to the first construction.

FIG. 5 is a view illustrating washing liquid remaining after washing the analysis chip according to the first construction. FIG. 5 is a cross-sectional view corresponding to the cross section taken along the line B-B of FIG. 1. As illustrated in FIG. 5, on the analysis chip 1 pulled up from the washing liquid 601 after the washing treatment, the washing liquid 601 remains on the main surface of the substrate 10 that is the hydrophilic surface, while the washing liquid 601 does not remain in the partition portion 12 that is the water repellent surface.

Figure 6:
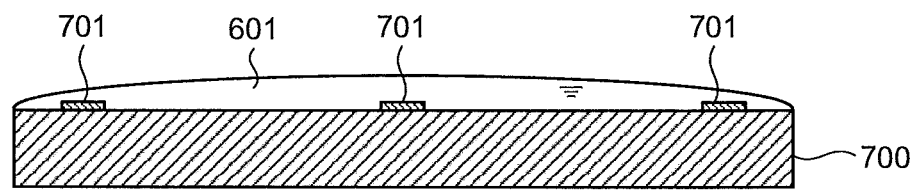
FIG. 6 is a view for illustrating the washing liquid remaining after washing of the analysis chip not having an extension portion.

FIG. 6 is a view illustrating the washing liquid remaining after washing an analysis chip not having an extension portion. FIG. 6 illustrates a configuration without the extension portion 13 in the analysis chip 1 illustrated in FIG. 1 and a partition portion 701 similar to the partition portion 12 is formed on a substrate 700 having a hydrophilic surface. As illustrated in FIG. 6, the washing liquid 601 remains on the substrate 700 to cover the partition portion 701 because the washing liquid 601 does not run out by the extension portion 13.

Examples of other washing methods include a method of completely pulling out the analysis chip 1 from the liquid surface of the washing liquid 601 to the outside of the liquid and entirely immersing the analysis chip 1 again and repeating pulling out and immersing, a method of leaving to stand the analysis chip 1 while the analysis chip is entirely immersed, and a method of stirring the washing liquid 601 with a stirrer while the analysis chip 1 is entirely immersed. The analysis chip 1 may be washed by any of the methods.

After the washing process, the analysis chip 1 is centrifugally dried using a general centrifuge dedicated for chips and slide glasses.

From the analysis chip having completed the washing and drying processes, an image is read using a high resolution fluorescence detection device or the like and digitizes the signal intensity (fluorescence intensity). Preferably, usable examples of the high resolution fluorescence detection device include 3D-Gene (registered trademark) Scanner (manufactured by Toray Industries, Inc.), SureScan microarray scanner (manufactured by Agilent Technologies), and GenePix (manufactured by Filgen, Inc.). The high resolution fluorescence detection device, however, is not limited to these examples.

According to the first construction described above, sample contamination in the adjacent reaction portions 11 can be avoided and the unreacted labeled substance adhering to the water repellent surface can be efficiently washed off because the analysis chip 1 is formed so that the water repellent surface is formed by the partition portion 12 for partitioning the reaction portions 11 and the extension portion 13 extending from a part of the partition portion 12 to the corner portion $C_1$ of the substrate 10 and the washing liquid 601 on the water repellent surface runs out via water repellent surface by surrounding each of the reaction portions 11 with the water repellent material in the analysis chip 1 having the reaction portions 11. The background noise due to the unreacted labeled substance generated after washing can be reduced by this configuration.

For example, in JP '057, the entire surface of the analysis chip other than the reaction portions is the water repellent surface with a sheet-like separator in the surface of the analysis chip. In that case, the hydrophilic region on the analysis chip surface is inside the reaction portion alone. Therefore, it is easily assumed that, when the analysis chip is pulled up from the washing liquid in the washing process, the large amount of a solution (the unreacted labeled substance) adhering to the separator flows into the reaction portion being the hydrophilic region and remains and the carry amount of the washing liquid into the subsequent washing liquid in a washing process carrying out several times increases. In addition, the amount of the liquid flowing into the reaction portion is not uniform depending on the direction and speed of pulling up the analysis chip so that a constant washing effect cannot be obtained and the analysis result may be affected. Moreover, when the washing is carried out with the separator attached, a problem in that the vicinity of the boundary between the reaction portion and the separator cannot be properly washed arises.

In contrast, in the first construction, the strip-like shape water repellent surface formed of the partition portion 12 and the extension portion 13 is only formed on a part of the substrate 10 and thus the amount the unreacted labeled substance adhering to the water repellent surface is small and the washing liquid on the water repellent surface can be removed efficiently via the extension portion 13. Consequently, the carry amount of the unreacted labeled substance in the subsequent washing treatment can also be reduced. Therefore, the analysis chip 1 can be appropriately washed by using the analysis chip 1 according to the first construction.

In the above-described first construction it has been described that the reaction portion 11 forms the recessed shape. The shape of the reaction portion 11, however, may be the same flat surface as the plane passing through the main surface of the substrate 10. In this case, the selective binding substance is immobilized on all or part of the surface of the reaction portion.

Modified Example 1 of First Construction

Figure 7:
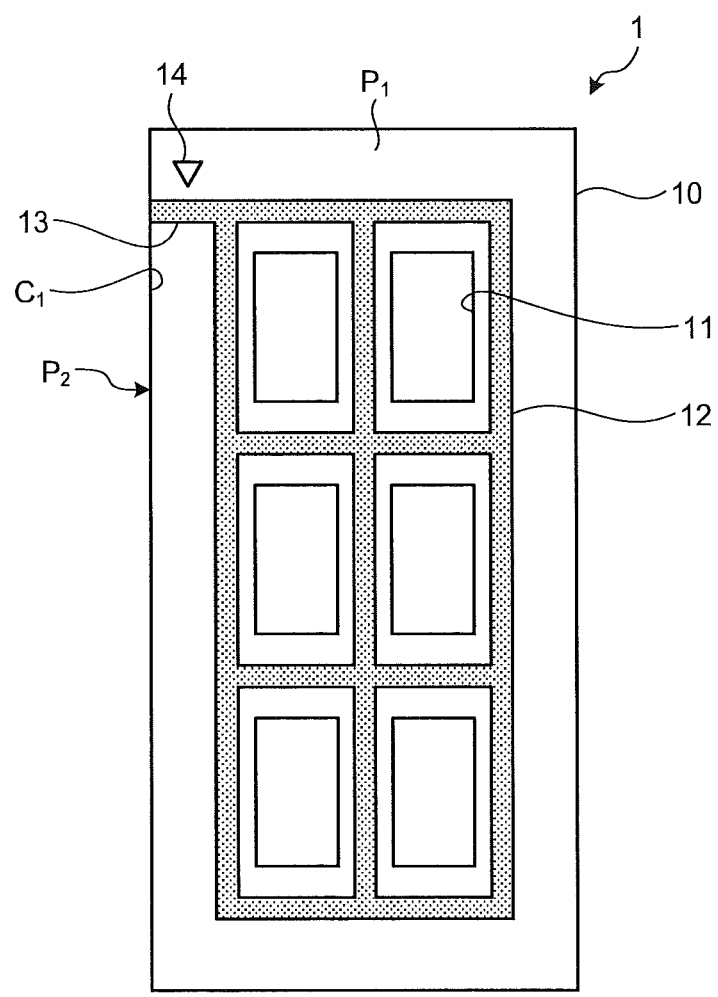
FIG. 7 is a plan view schematically illustrating an analysis chip according to Modified Example 1 of the first construction.

FIG. 7 is a plan view schematically illustrating an analysis chip according to Modified Example 1 of the first construction. In Modified Example 1, an indicator portion 14 indicating the position of the extension portion 13 is formed in the analysis chip 1 according to the above-described first construction. When a transparent material is used as the water repellent material used to form the partition portion 12 and the extension portion 13, the formation position of the extension portion 13 is checked by using the refractive index difference and the like. However, visual check of the forming position of the extension portion 13 on the main surface of the substrate 10 may be difficult. The forming position of the extension portion 13 can be easily determined and the orientation of the edge side at the time of taking out from the washing liquid 601 can be accurately determined by providing the indicator portion 14.

In Modified Example 1, it has been described that the indicator portion 14 is provided on the substrate 10. However, the indicator portion 14 is not limited to this configuration and can be provided as long as the indicator can be visually recognized. For example, the location where the extension portion 13 is formed may be indicated by an indicator portion of a symbol such as an arrow or a symbol such as a circle or a square indicating the presence of the extension portion 13 in the vicinity, an indicator portion formed by processing a recessed shape, a protruding shape, a notch shape or the like, and an indicator portion formed by providing a color (for example, green). In addition, Modified Example 1 may be an analysis chip in which a barcode provided on the substrate 10 by attaching or printing is used as an indicator portion and the barcode is provided in the vicinity of the extension portion 13 or on the end portion opposite to the end portion where the extension portion 13 is formed.

Modified Example 2 of First Construction

Figure 8:
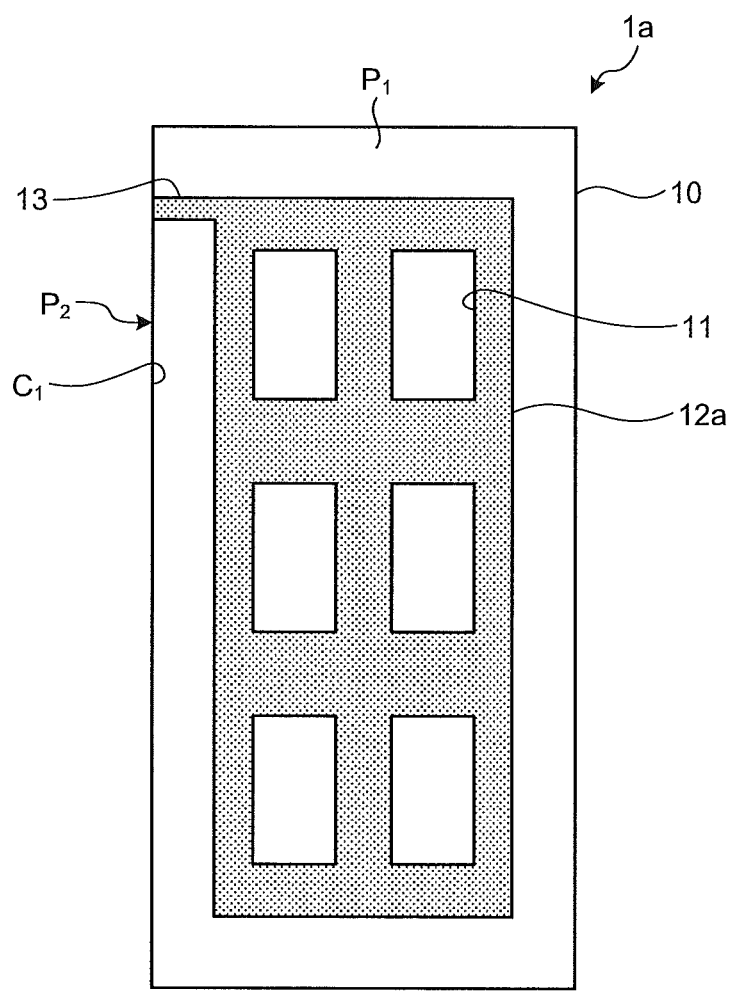
FIG. 8 is a plan view schematically illustrating an analysis chip according to Modified Example 2 of the first construction.

FIG. 8 is a plan view schematically illustrating an analysis chip according to Modified Example 2 of the first construction. In the above-described first construction, it has been described that the partition portion 12 surrounds at a predetermined distance from the outer edge of the reaction portions 11. In Modified Example 2, however, a partition portion 12a is formed in a region continuous with the outer edge of the reaction portions 11 and surrounds the reaction portions 11. An analysis chip 1a according to Modified Example 2 is formed in a rectangular region including the outer edge of the reaction portions 11 instead of the above-described partition portion 12 and has a partition portion 12a that partitions the reaction portions 11.

Modified Example 3 of First Construction

Figure 9:
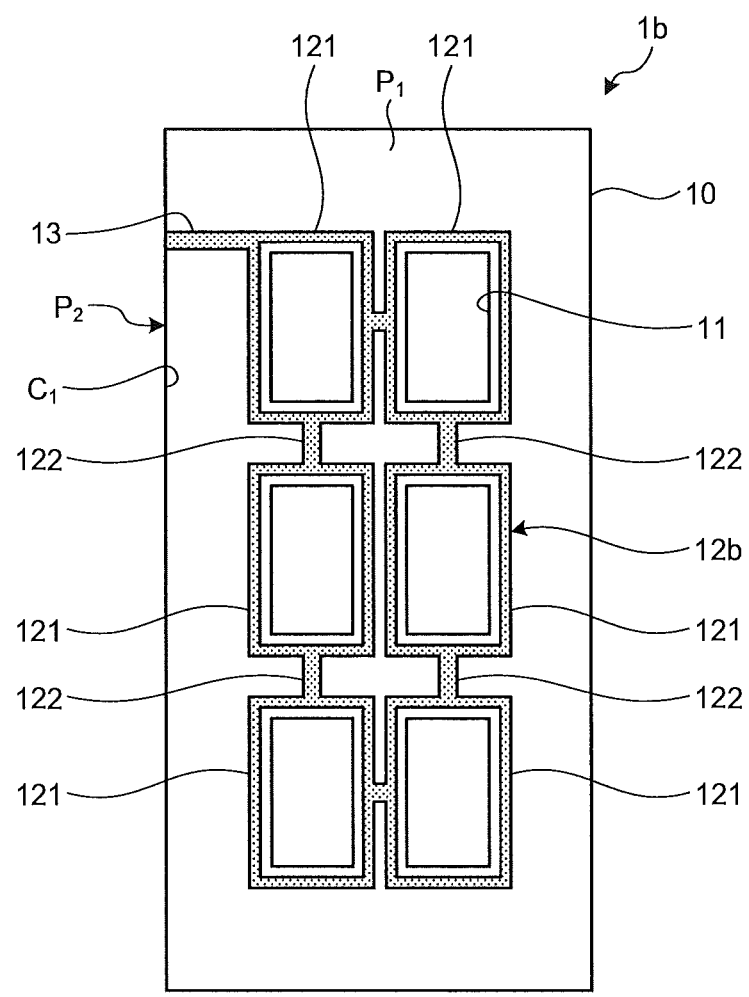
FIG. 9 is a plan view schematically illustrating an analysis chip according to Modified Example 3 of the first construction.

FIG. 9 is a plan view schematically illustrating an analysis chip according to Modified Example 3 of the first construction. In the above-described first construction, it has been described that the reaction portions 11 are partitioned by dividing the inside of the annular frame of the partition portion 12. In Modified Example 3, a partition portion 12b individually surrounds each of the reaction portions 11. An analysis chip 1b according to Modified Example 3 has a partition portion 12b having a plurality of surrounding portions 121 that individually surround the reaction portions 11 and a plurality of coupling portions 122 coupling the surrounding portions 121 to each other, instead of the above-described partition portion 12. Each of the surrounding portion 121 and the coupling portion 122 is formed of the water repellent material.

Modified Example 4 of First Construction

Figure 10:
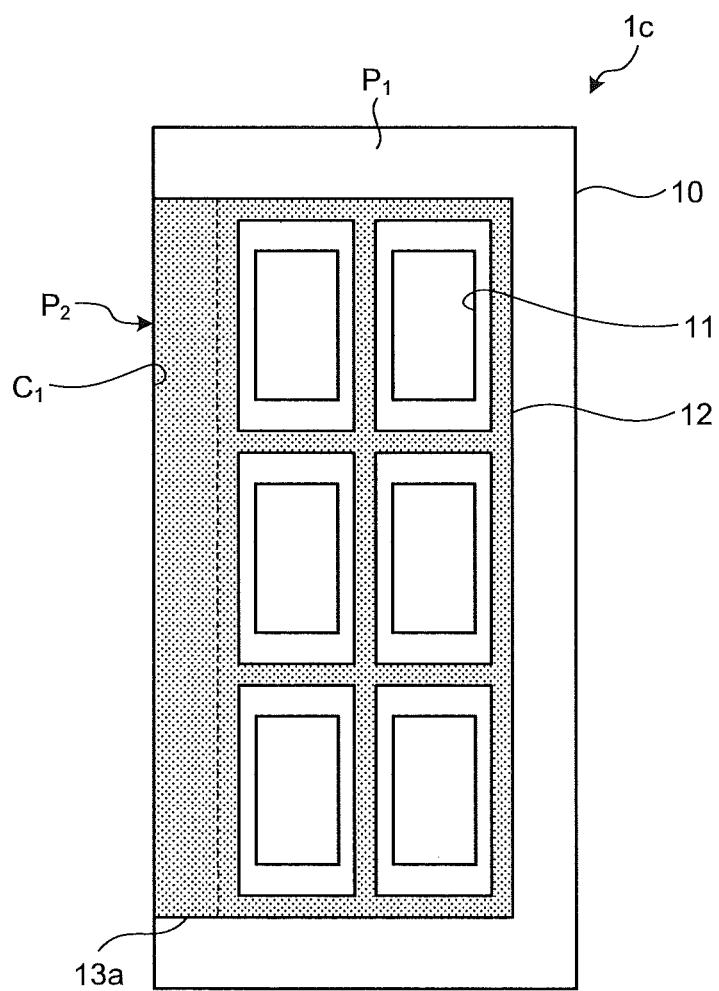
FIG. 10 is a plan view schematically illustrating an analysis chip according to Modified Example 4 of the first construction.

FIG. 10 is a plan view schematically illustrating an analysis chip according to Modified Example 4 of the first construction. In the above-described first construction, it has been described that the length of the extension portion 13 in the direction extending from the partition portion 12 toward the corner portion $C_1$ (orientation direction) is larger than the width orthogonal to the orientation direction. In Modified Example 4, however, an analysis chip 1c has an extension portion 13a the length of which in the orientation direction is shorter than the width orthogonal to the orientation direction. The analysis chip 1c according to Modified Example 4 has the extension portion 13a extending from one outside edge of the rectangular formation region of the partition portion 12 to the corner portion $C_1$, instead of the above-described extension portion 13. The extension portion 13a is connected to a large part of one edge side forming the corner portion $C_1$ of the substrate 10. By this configuration, when the analysis chip 1c is pulled up from the washing liquid 601, the state in which a part of the extension portion 13a is in contact with the liquid surface can be more reliably maintained, even if the edge side is somewhat inclined with respect to the liquid surface.

Modified Example 5 of First Construction

Figure 11:
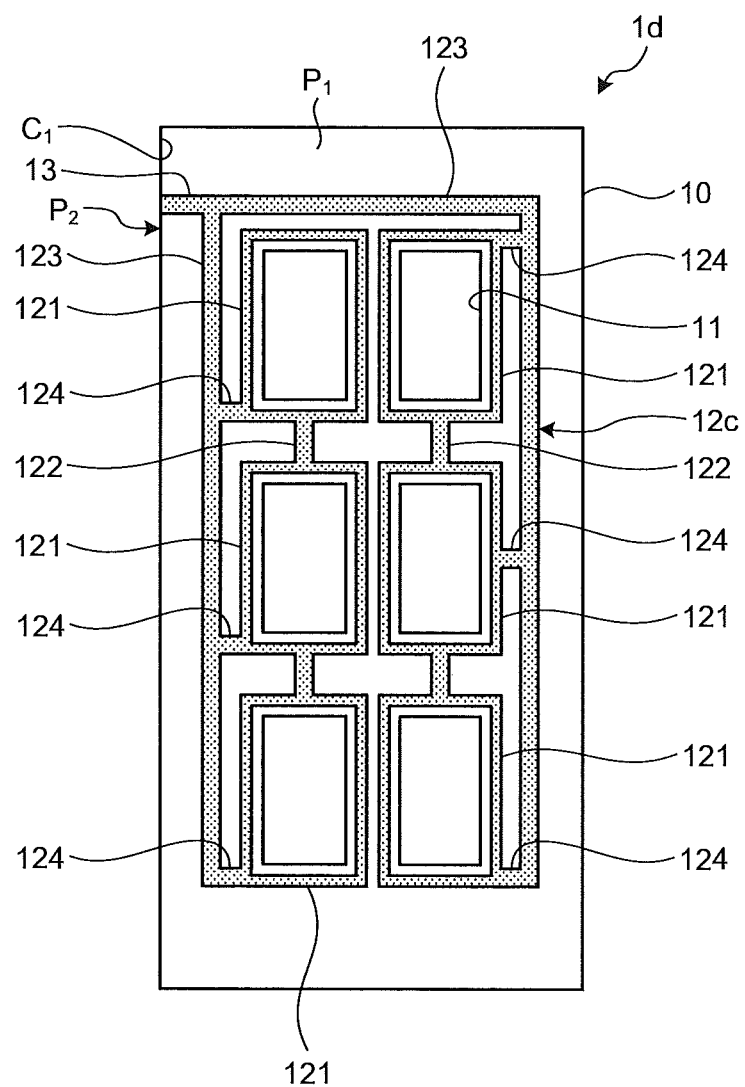
FIG. 11 is a plan view schematically illustrating an analysis chip according to Modified Example 5 of the first construction.

FIG. 11 is a plan view schematically illustrating an analysis chip according to Modified Example 5 of the first construction. In the above-described Modified Example 3 (refer to FIG. 9), it has been described that the extension portion 13 is connected to one surrounding portion 121 of the partition portion 12b. In Modified Example 5, however, the extension portion 13 is connected to an outer peripheral portion 123 of a partition portion 12c. An analysis chip 1d according to Modified Example 5 has a partition portion 12c having a plurality of surrounding portions 121 individually surrounding the reaction portions 11, a plurality of coupling portions 122 coupling the surrounding portions 121 to each other, a substantially U-shaped outer peripheral portion 123 that forms the outer periphery of the partition portion 12c and surrounds the reaction portions 11, and a plurality of second coupling portions 124 coupling the surrounding portions 121 and the outer peripheral portion 123, instead of the above-described partition portion 12. In the partition portion 12c, each of the surrounding portions 121 is connected as one water repellent surface by the outer peripheral portion 123 and the second coupling portion 124.

Modified Example 6 of First Construction

Figure 12:
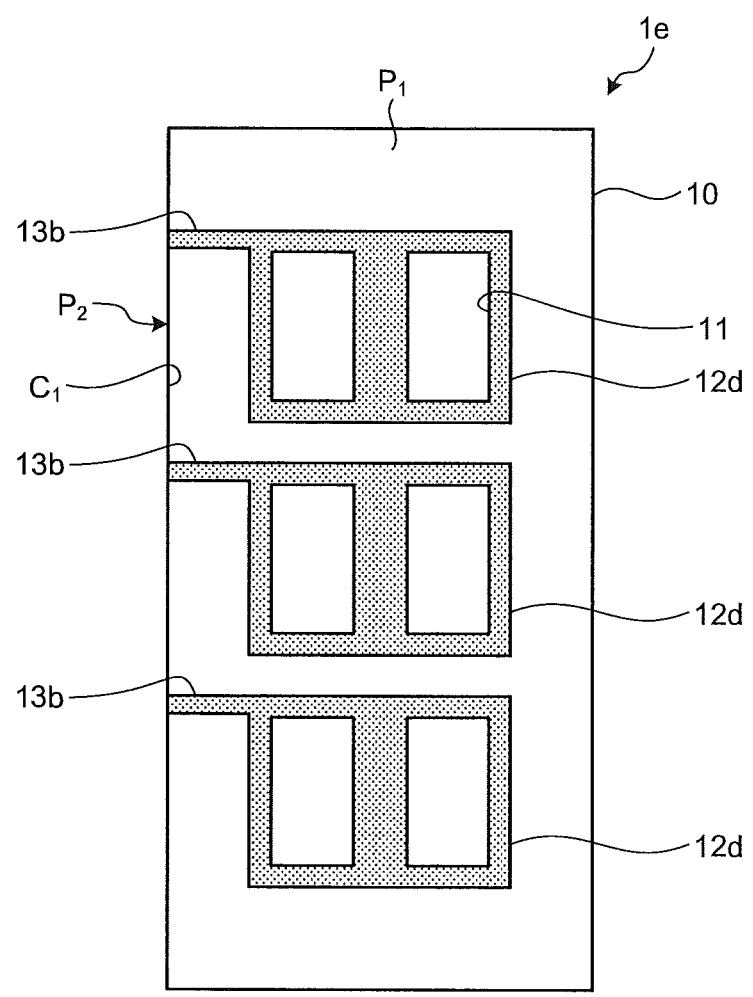
FIG. 12 is a plan view schematically illustrating an analysis chip according to Modified Example 6 of the first construction.

FIG. 12 is a plan view schematically illustrating an analysis chip according to Modified Example 6 of the first construction. In the above-described first construction, it has been described that the partition portion 12 forms one continuous water repellent surface. In Modified Example 6, however, partition portions are formed of three partition portions 12d surrounding and portioning the two reaction portions 11 as one set. An analysis chip 1e according to Modified Example 6 has the three partition portions 12d surrounding and dividing the two reaction portions 11 as one set and three extension portions 13b each extending from the partition portions 12d to the corner portion $C_1$. Even when the analysis chip 1e has extension portions 13b, the above-described effect can be obtained when each of the extension portions 13b is connected to the same edge side (corner portion $C_1$) of the substrate 10.

Modified Example 7 of First Construction

Figure 13:
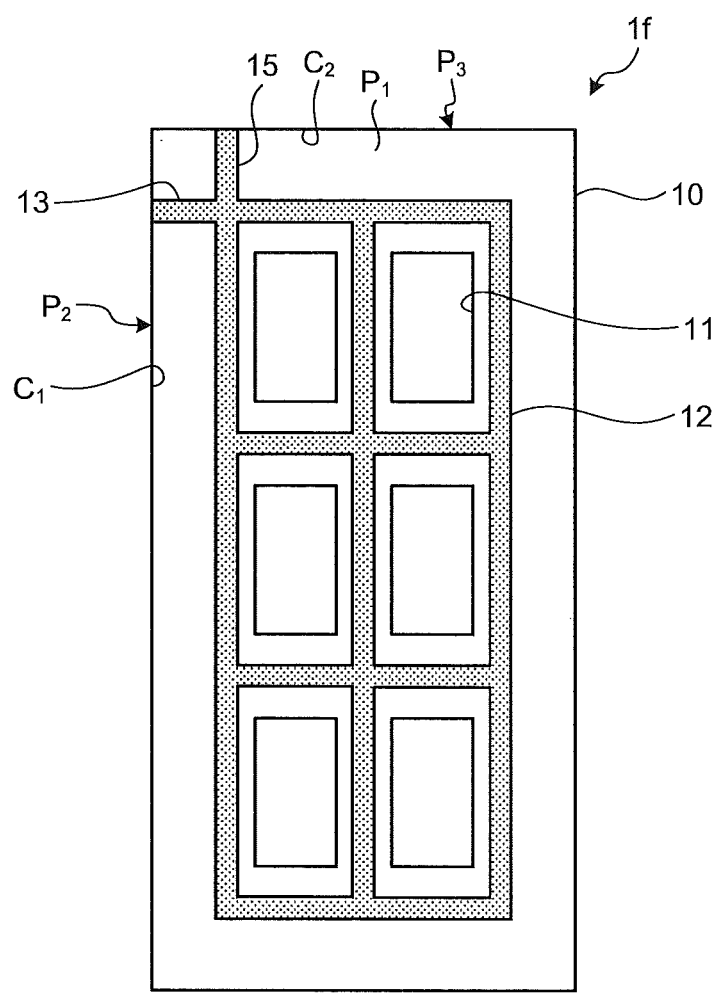
FIG. 13 is a plan view schematically illustrating an analysis chip according to Modified Example 7 of the first construction.

FIG. 13 is a plan view schematically illustrating an analysis chip according to Modified Example 7 of the first construction. In the above-described first construction, it has been described that the extension portion 13 is connected to one edge side of the substrate 10. In Modified Example 7, however, in addition to the extension portion 13, an analysis chip if has an extension portion 15 connected from the partition portion 12 to an edge side that is different from the edge side to which the extension portion 13 is connected and forms a corner portion $C_2$ formed by the surface $P_1$ and a surface $P_3$ orthogonal to the surface $P_1$ and the surface $P_2$. In addition to the configuration of the above-described analysis chip 1, the analysis chip if according to Modified Example 7 has the extension portion 15 connected to the edge side that is different from and orthogonal to the edge side to which the extension portion 13 is connected. By forming the extension portion 15, when the analysis chip if is pulled up from the washing liquid 601, the edge side where the extension portion 15 is located can also be selected as the edge side to be downward and thus the degree of freedom for pulling up can be increased. In addition, each of the extension portions are connected to the edge sides having different lengths, whereby the washing processing can be carried out by changing the orientation of the analysis chip if depending on, for example, the size of the opening of the container 600

Modified Example 8 of First Construction

Figure 14:
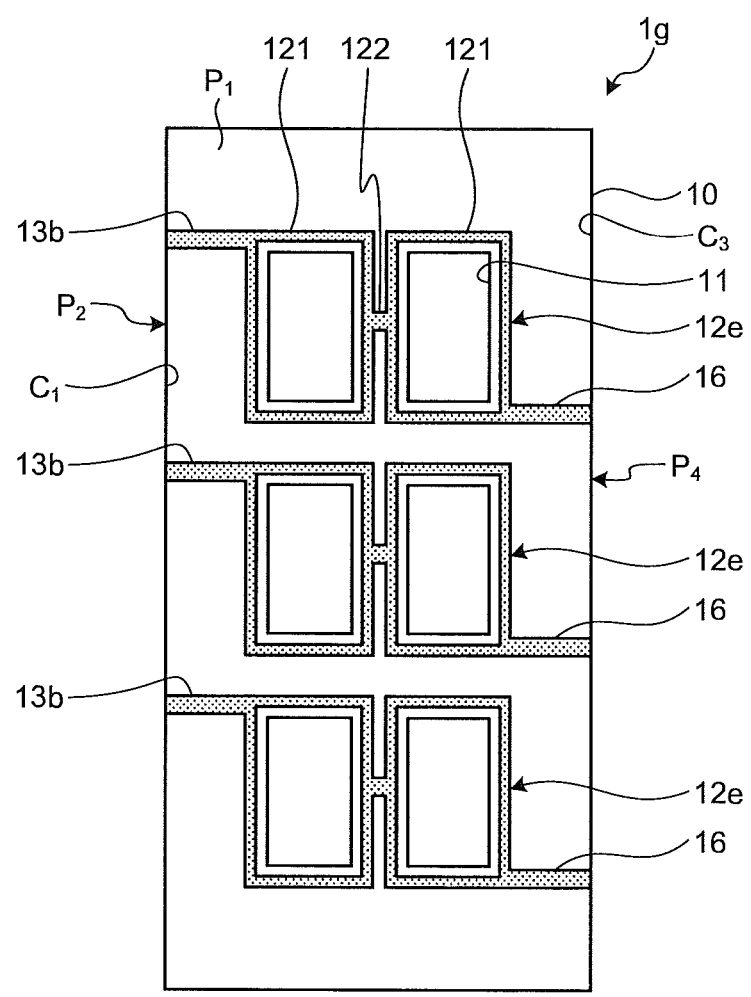
FIG. 14 is a plan view schematically illustrating an analysis chip according to Modified Example 8 of the first construction.

FIG. 14 is a plan view schematically illustrating an analysis chip according to Modified Example 8 of the first construction. In the above-described Modified Example 6, it has been described that the partition portions are formed of the three partition portions 12d surrounding and partitioning the two reaction portions 11 as one set and the extension portions 13b extend from each of the partition portions. In Modified Example 8, however, an analysis chip 1g has three partition portions 12e and extension portions 13b and 16 extending from each of the partition portions 12e. The analysis chip 1g according to Modified Example 8 has the three partition portions 12e surrounding and partitioning the two reaction portions 11 as one set, the three extension portions 13b extending from the partition portions 12e to one outer edge of the substrate 10, and the three extension portions 16 connected to edge side that is different from the edge side to which the extension portions 13b are connected and forms a corner portion $C_3$ formed by the surface $P_1$ and a surface $P_4$ facing the surface $P_2$. The partition portion 12e has the surrounding portions 121 surrounding the reaction portions 11 and the coupling portion 122 coupling the adjacent surrounding portions 121 to each other. The extension portion 16 may be connected to the partition portion 12d according to the Modified Example 6 (refer to FIG. 12).

Modified Example 9 of First Construction

Figure 15:
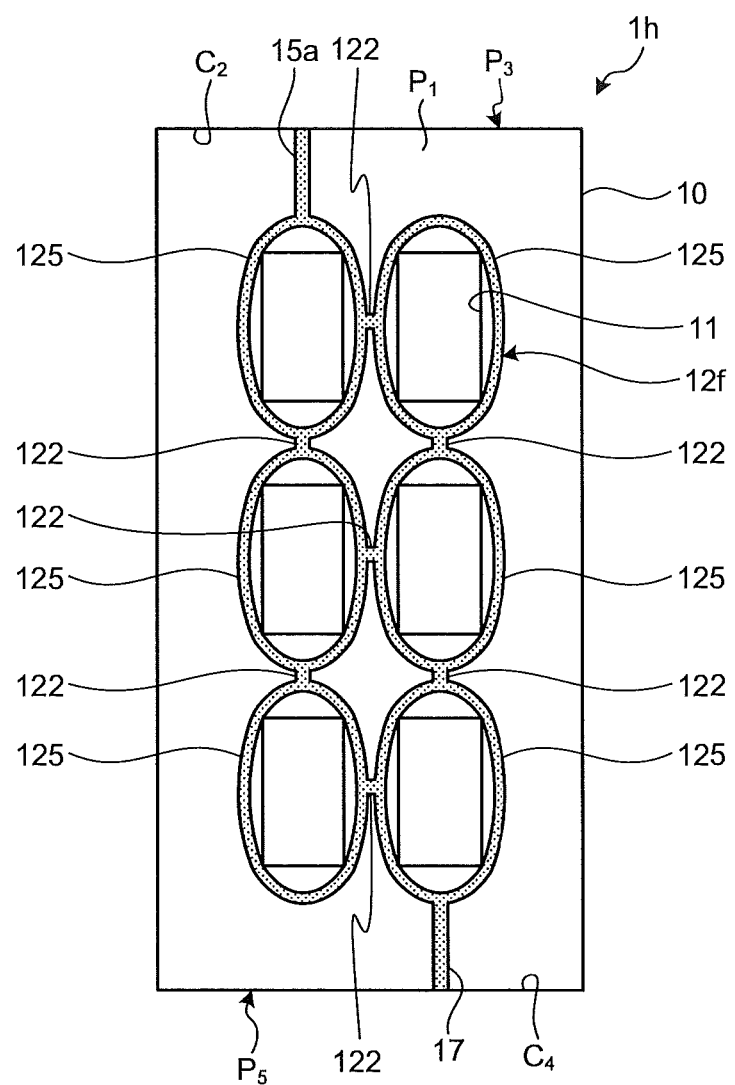
FIG. 15 is a plan view schematically illustrating an analysis chip according to Modified Example 9 of the first construction.

FIG. 15 is a plan view schematically illustrating an analysis chip according to Modified Example 9 of the first construction. In the above-described Modified Example 3 (refer to FIG. 9), it has been described that the surrounding portion 121 forms a rectangular annular shape and surrounds the reaction portions 11. In Modified Example 9, however, an analysis chip 1h has surrounding portions 125 in an elliptical annular shape surrounding the reaction portions 11. The analysis chip 1h according to Modified Example 9 has a plurality of surrounding portions 125 that individually surround the reaction portions 11, a partition portion 12f having a plurality of coupling portions 122 coupling the surrounding portions 125 to each other, an extension portion 15a connected from the surrounding portion 125 to the edge side forming the corner portion $C_2$, and an extension portion 17 connected from the surrounding portion 125 to the edge side that is different from the edge side to which the extension portion 15a is connected and forms a corner portion $C_4$ formed by the surface $P_1$ and a surface $P_5$ facing the surface $P_3$. In addition to the surrounding portion 125 that forms an elliptical annular shape surrounding the reaction portion 11 in Modified Example 9, the surrounding portion may be a surrounding portion forming a circular shape or a polygonal shape surrounding the reaction portion.

Modified Example 10 of First Construction

Figure 16:
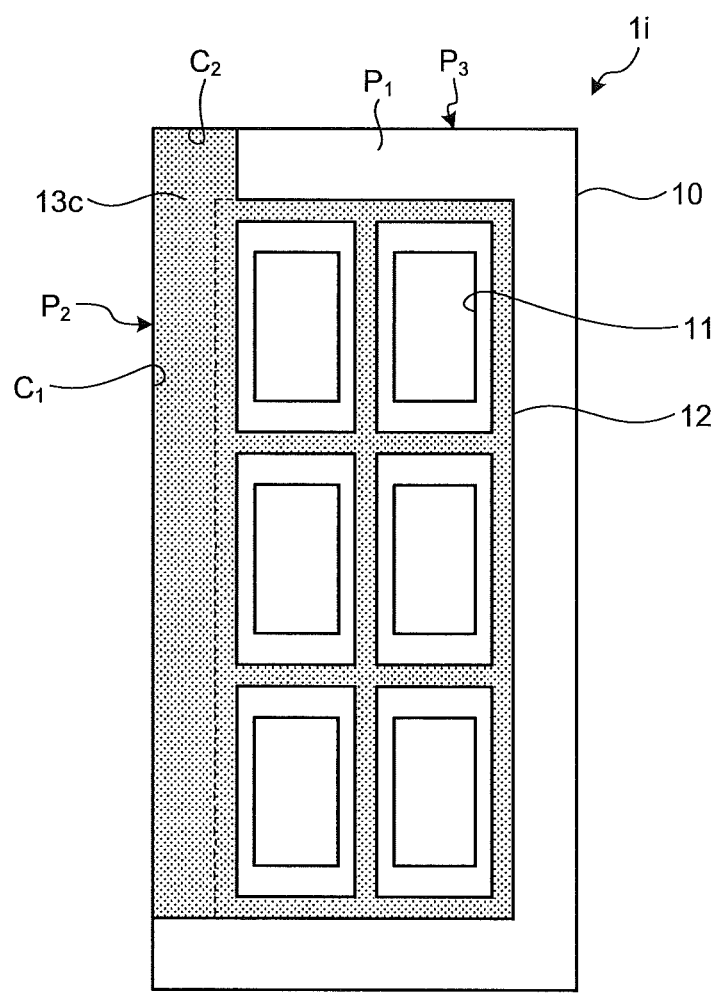
FIG. 16 is a plan view schematically illustrating an analysis chip according to Modified Example 10 of the first construction.

FIG. 16 is a plan view schematically showing an analysis chip according to Modified Example 10 of the first construction. In the above-described Modified Example 4 (refer to FIG. 10), it has been described that the length in the orientation direction of the extension portion 13a is shorter than the width orthogonal to the orientation direction. In Modified Example 4, however, an extension portion 13c is also connected to a different edge side. An analysis chip 1i according to Modified Example 10 has an extension portion 13c connected from the rectangular forming region of the partition portion 12 to two consecutive edge sides being the edge sides of the substrate 10. As described in Modified Example 10, the extension portion 13c may be connected to the two edge sides forming the corner portions $C_1$ and $C_2$ on the substrate 10 by enlarging the area of the extension portion 13c.

Modified Example 11 of First Construction

Figure 17:
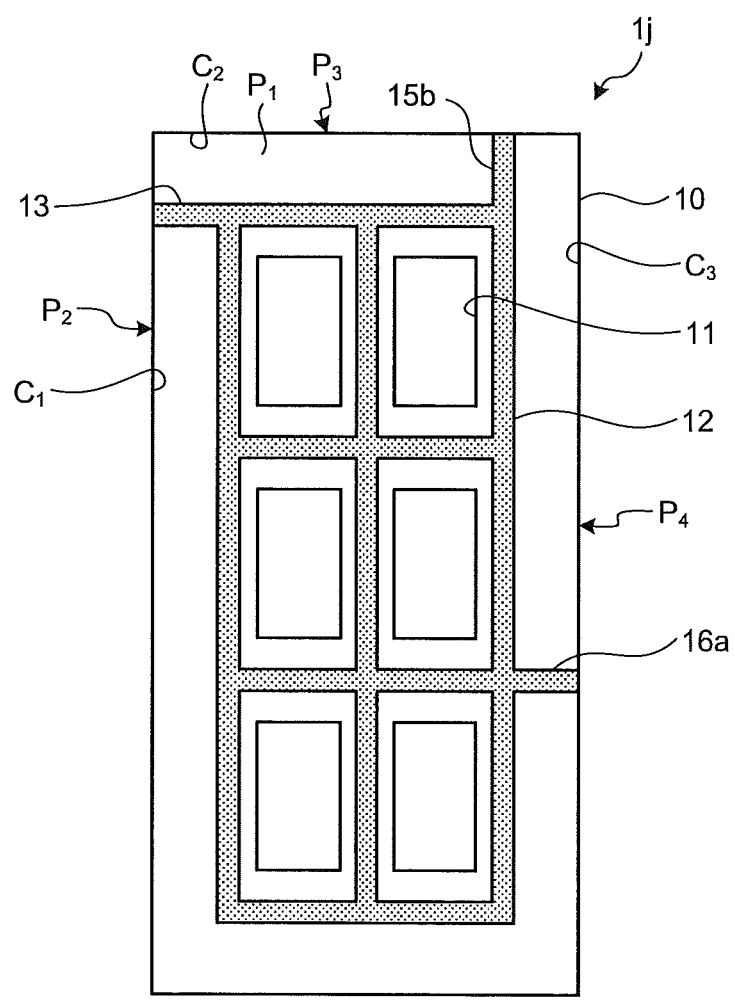
FIG. 17 is a plan view schematically illustrating an analysis chip according to Modified Example 11 of the first construction.

FIG. 17 is a plan view schematically illustrating an analysis chip according to Modified Example 11 of the first construction. In the above-described first construction, it has been described that the extension portion 13 is connected to one edge side of the substrate 10. In Modified Example 11, however, an analysis chip 1j has extension portions 15b and 16a connected to different edge sides from each other in addition to the extension portion 13. In addition to the configuration of the above-described analysis chip 1, the analysis chip 1j according to Modified Example 11 has the extension portion 15b connected to the edge side that is different from the edge side to which the extension portion 13 is connected and forms the corner portion $C_2$ formed by the surface $P_1$ and the surface $P_3$ and the extension portion 16a connected to the edge side that is different from the edge side to which the extension portion 13 is connected and forms the corner portion $C_3$ formed by the surface $P_1$ and the surface $P_4$. By forming the extension portions 15b and 16a, when the analysis chip 1j is pulled up from the washing liquid 601, the three edge sides on the sides of the extension portions 13, 15b, and 16a can be selected as the lower edge side and thus the degree of freedom for pulling up can be increased.

Modified Example 12 of First Construction

Figure 18:
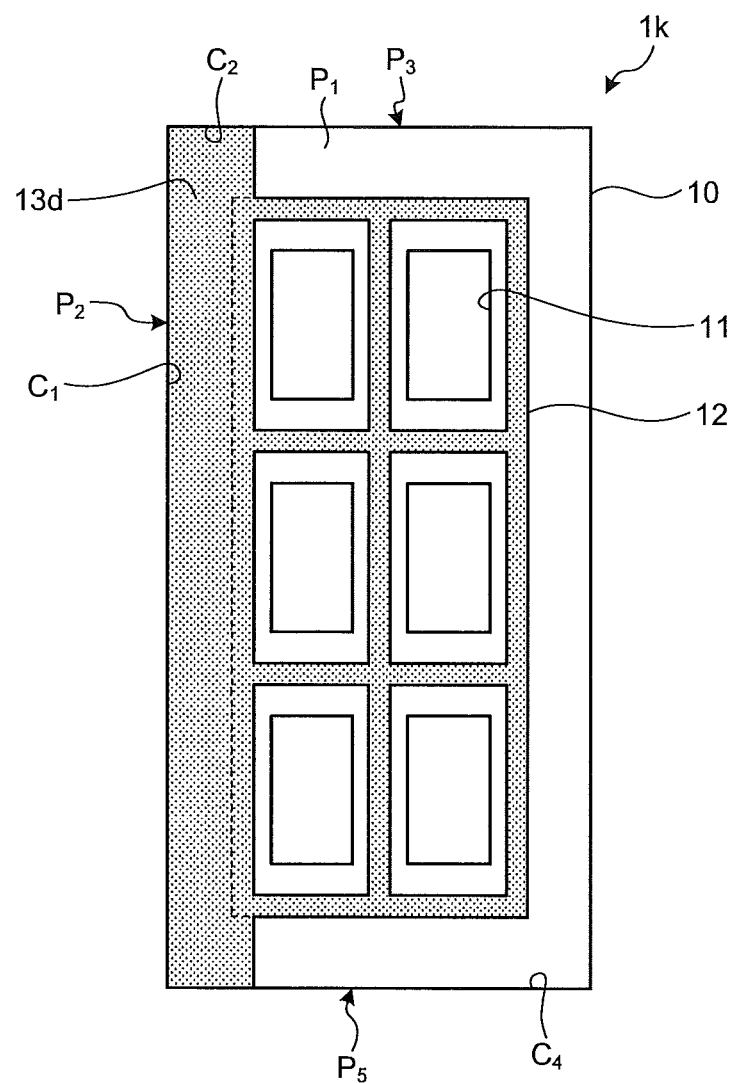
FIG. 18 is a plan view schematically illustrating an analysis chip according to Modified Example 12 of the first construction.

FIG. 18 is a plan view schematically illustrating an analysis chip according to Modified Example 12 of the first construction. In Modified Example 12, the extension portion 13c according to the above-described Modified Example 10 (refer to FIG. 16) is further extended and connected to three edge sides. An analysis chip 1k according to Modified Example 12 has an extension portion 13d connected from the rectangular forming region of the partition portion 12 to three edge sides being the edge sides of the substrate 10 and forming the corner portions of $C_1$, $C_2$, $C_3$, and $C_4$. As in Modified Example 12, the extension portion 13d may be connected to the three edge sides on the substrate 10 by enlarging the area of the extension portion 13d.

Modified Example 13 of First Construction

Figure 19:
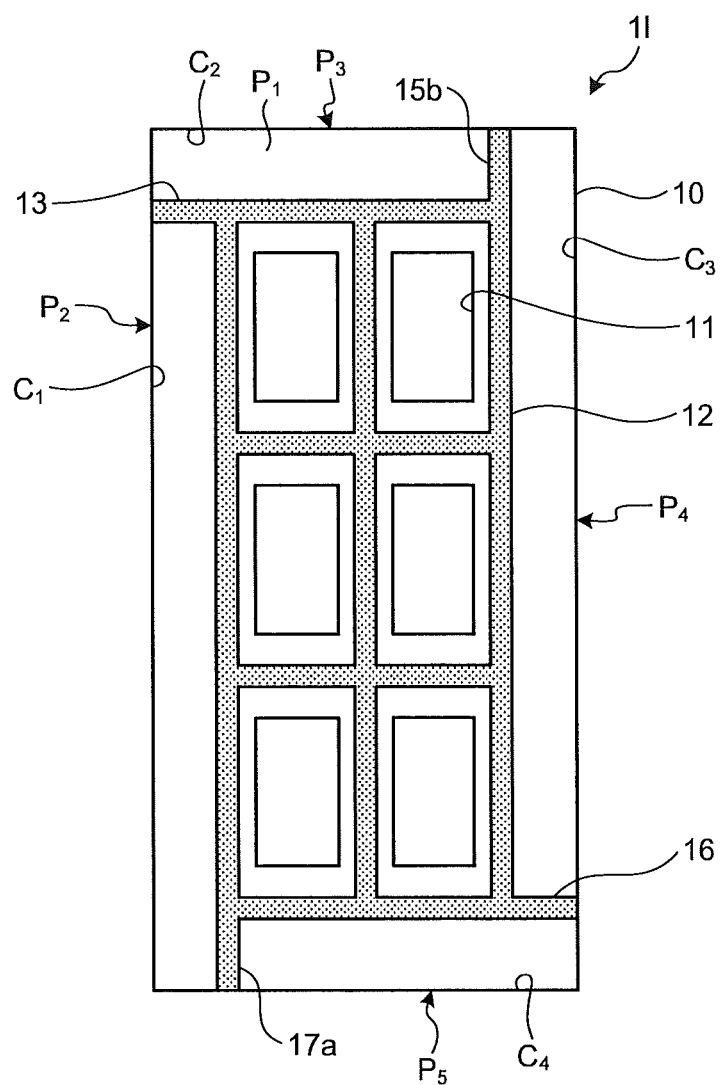
FIG. 19 is a plan view schematically illustrating an analysis chip according to Modified Example 13 of the first construction.

FIG. 19 is a plan view schematically illustrating an analysis chip according to Modified Example 13 of the first construction. In the above-described first construction, it has been described that the extension portion 13 is connected to one edge side of the substrate 10. In Modified Example 13, however, an analysis chip 1l has extension portions 15b, 16, and 17a each connected to different edge sides from each other, in addition to the extension portion 13. In addition to the configuration of the above-described analysis chip 1, the analysis chip 1l according to Modified Example 13 has extension portions 13, 15b, 16, and 17a connected to the four edge sides forming the corner portions $C_1$, $C_2$, $C_3$ and $C_4$, respectively. By forming the extension portions 13, 15b, 16, and 17a, when the analysis chip 1l is pulled up from the washing liquid 601, the washing treatment can be carried out without noticing the orientation of the edge side to be downward due to the connection of four edge sides and the extension portions.

Modified Example 14 of First Construction

Figure 20:
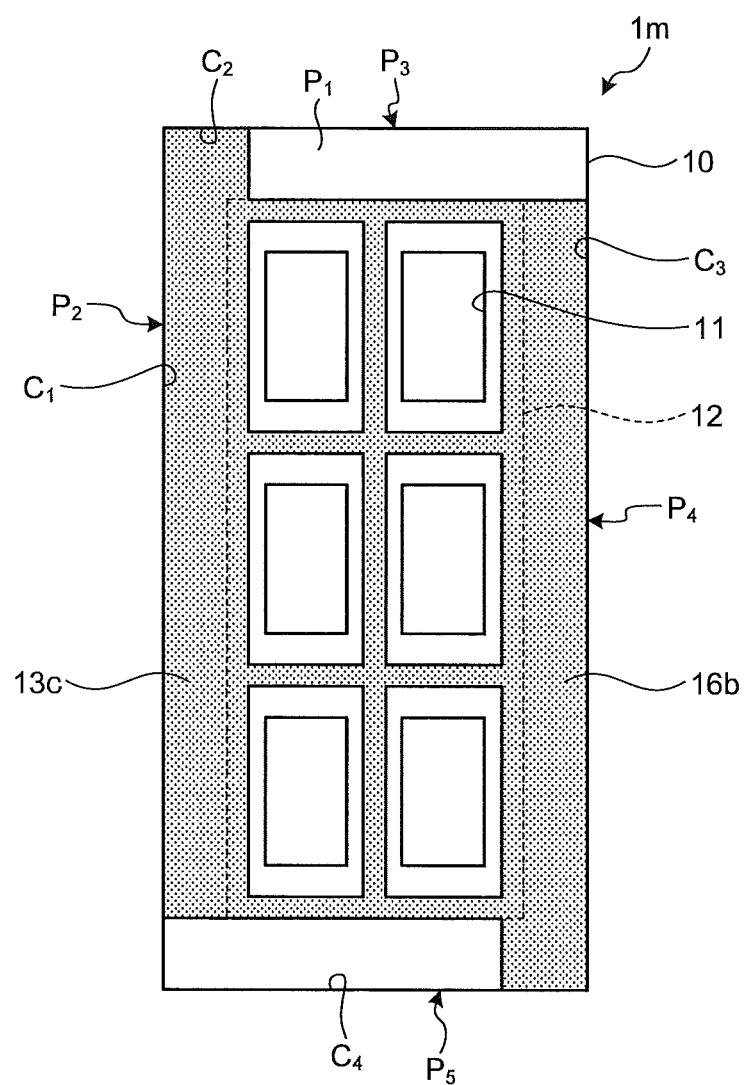
FIG. 20 is a plan view schematically illustrating an analysis chip according to Modified Example 14 of the first construction.

FIG. 20 is a plan view schematically illustrating an analysis chip according to Modified Example 14 of the first construction. The analysis chip 1m according to Modified Example 14 further has an extension portion 16b that is rotationally symmetric about the center of the substrate 10 with respect to the extension portion 13c according to Modified Example 10 (refer to FIG. 16) described above. The extension portion 16b extends from the partition portion 12 toward the outer edge of the substrate 10 and is connected to two edge sides forming the corner portions $C_3$ and $C_4$. By forming the extension portions 13c and 16b, when the analysis chip 1m is pulled up from the washing liquid 601, the washing treatment can be carried out without noticing the orientation of the edge side to be downward due to the connection of four edge sides forming the corner portions $C_1$, $C_2$, $C_3$ and $C_4$ and the extension portions.

Modified Example 15 of First Construction

Figure 21:
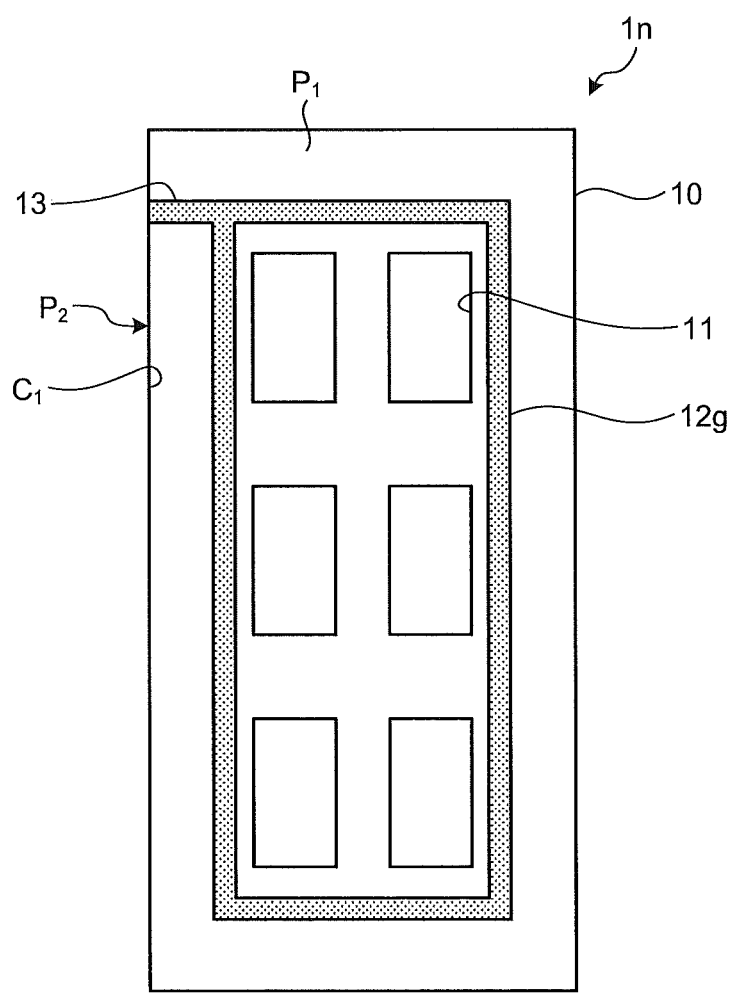
FIG. 21 is a plan view schematically illustrating an analysis chip according to Modified Example 15 of the first construction.

FIG. 21 is a plan view schematically illustrating an analysis chip according to Modified Example 15 of the first construction. In the above-described first construction and Modified Examples 1 to 14, it has been described that the partition portion individually partitions each of the reaction portions. An analysis chip 1n according to Modified Example 15, however, has a partition portion 12g collectively surrounding the reaction portions 11. As in the partition portion 12g, the partition portion may collectively surround the reaction portions 11 to prevent the leakage of the sample from the substrate 10.

Modified Example 16 of First Construction

Figure 22:
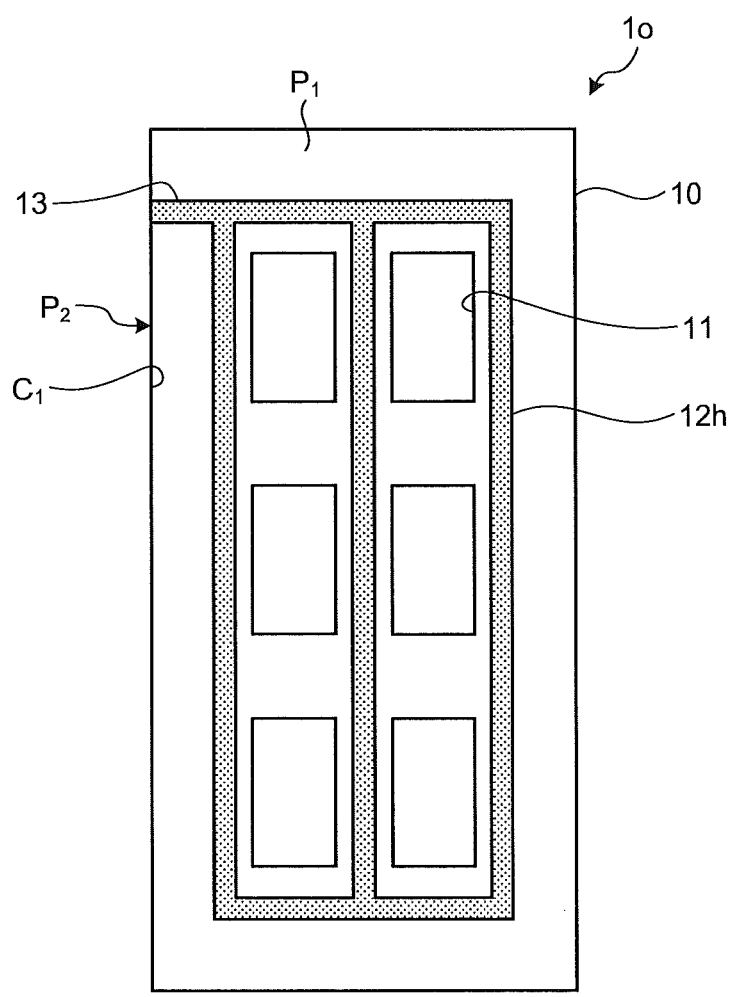
FIG. 22 is a plan view schematically illustrating an analysis chip according to Modified Example 16 of the first construction.

FIG. 22 is a plan view schematically illustrating an analysis chip according to Modified Example 16 of the first construction. In addition to the above-described Modified Example 15 (refer to FIG. 21), as in the analysis chip 1o according to Modified Example 16, the partition portion may be a partition portion 12h surrounding each of the predetermined number of the reaction portions 11 (three reaction portions in Modified Example 16).

Modified Example 17 of First Construction

Figure 23:
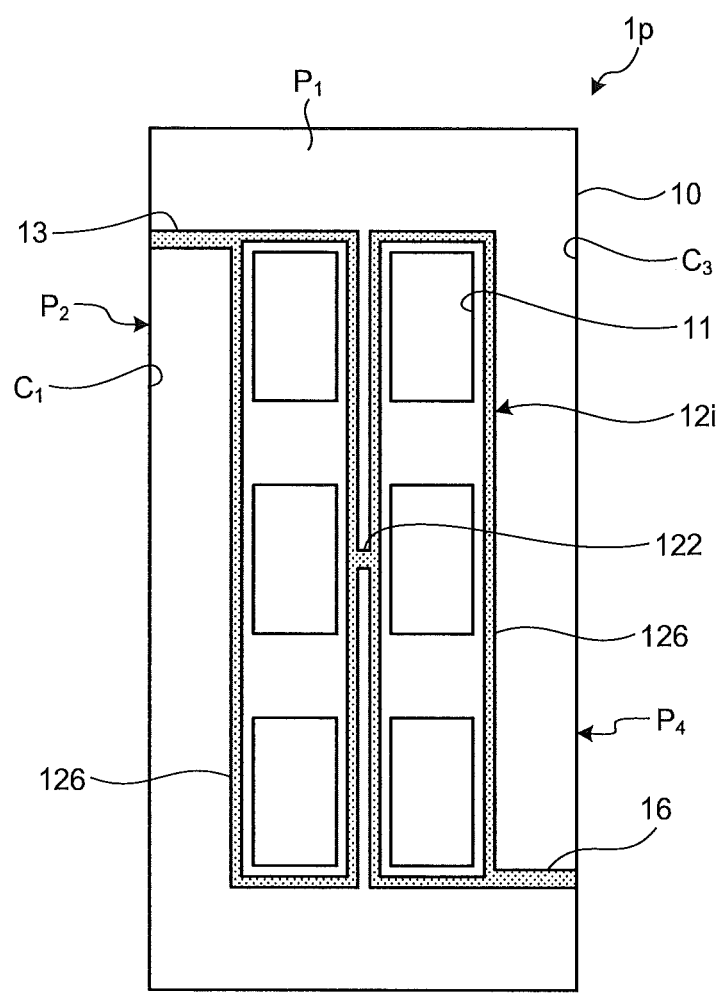
FIG. 23 is a plan view schematically illustrating an analysis chip according to Modified Example 17 of the first construction.

FIG. 23 is a plan view schematically illustrating an analysis chip according to Modified Example 17 of the first construction. With respect to the above-described Modified Example 16 (refer to FIG. 22), as in an analysis chip 1p according to Modified Example 17, the analysis chip $1p$ may have the two surrounding portions 126 each surrounding the predetermined number of the reaction portions 11 (three reaction portions in Modified Example 17), a partition portion $12i$ having a coupling portion 122 coupling the surrounding portions 126 to each other, and extension portions 13 and 16 each connected from the partition portion $12i$ to two edge sides that are different edge sides of the substrate 10 and forms the corner portions $C_1$ and $C_3$.

Second Construction

Figure 24:
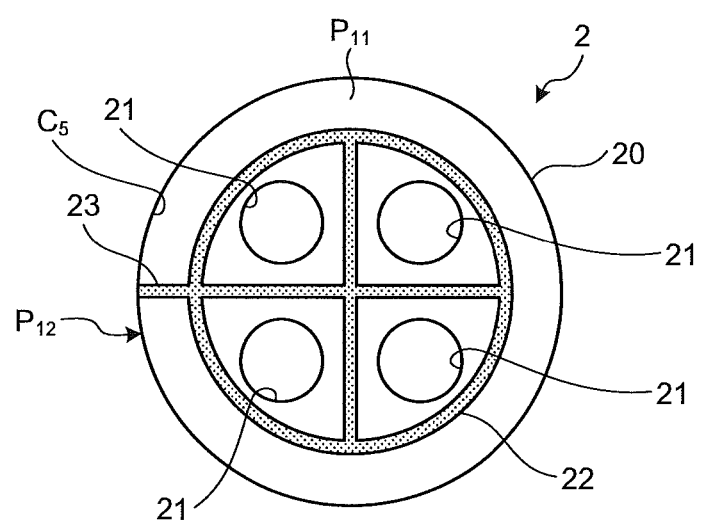
FIG. 24 is a plan view schematically illustrating an analysis chip according to a second construction.

FIG. 24 is a plan view schematically illustrating an analysis chip according to a second construction. In the above-described first construction it has been described that the substrate 10 is a flat plate the main surface of which forms a rectangular shape. An analysis chip 2 according to the second construction however, includes a planar substrate 20 having a plurality of reaction portions 21 (four reaction portions in the second construction), a partition portion 22, and an extension portion 23 being a connection portion and provided with a flat plate-like substrate 20 the main surface of which is a circular shape. The material of the substrate 20 is the same as the material of the above-described substrate 10.

A plurality of recessed reaction portions 21 are formed on one main surface of the substrate 20. The reaction portion 21 is composed of a bottom surface and a wall surface connecting the bottom surface and the main surface of the substrate 20. The selective binding substance is immobilized in the hollow space formed by the bottom surface and the wall surface. Similar to the reaction portion 11, the reaction portion 21 has a plurality of protrusion portions protruding from the bottom surface in a protruding shape.

The partition portion 22 is provided on the main surface of the substrate 20 and partitions the reaction portions 21 by surrounding each of the reaction portions 21 with a water repellent material. The partition portion 22 has a circular ring outer periphery, forms independent partitions for each of reaction portions 21, and forms a water repellent surface having a surface with water repellency.

The extension portion 23 is provided on the main surface of the substrate 20 and extends from a part of the partition portion 22 to a corner portion $C_5$ formed by the outer edge (the edge side) of the substrate 20. The corner portion $C_5$ is an angle formed by a surface $P_u$ on which the reaction portions 21 of the substrate 20 are provided and a side surface $P_{12}$ orthogonal to this surface $P_u$ in FIG. 24. The surface $P_u$ and the surface $P_{12}$ form straight lines with each other in the cross section of the substrate 20 and the corner $C_5$ is formed by these straight lines intersected with each other. The extension portion 23 extends in a strip-like shape and forms a water repellent surface having a surface with water repellency. The extension portion 23 is continuous with the partition portion 22. In other words, the water repellent surface of the partition portion 22 and the water repellent surface of the extension portion 23 form a continuous surface. The partition portion 22 and the extension portion 23 are formed by using a similar water repellent material and a method to the material and the method of the partition portion 12 and the extension portion 13 described above.

Similar to the first construction, according to the above-described second construction, sample contamination in the adjacent reaction portions 21 can be avoided and the unreacted labeled substance adhering to the water repellent surface can be efficiently washed out because, in the analysis chip 2 having the reaction portions 21, the water repellent surface is formed by the partition portion 22 partitioning the reaction portions 21 and the extension portion 23 extending from a part of the partition portion 22 to the corner portion $C_5$ of the substrate 20 by surrounding each of the reaction portions 21 with the water repellent material and the washing liquid 601 on the water repellent surface runs out via the extension portion 23. The background noise due to the unreacted labeled substance generated after washing can be reduced by this configuration.

Third Construction

Figure 25:
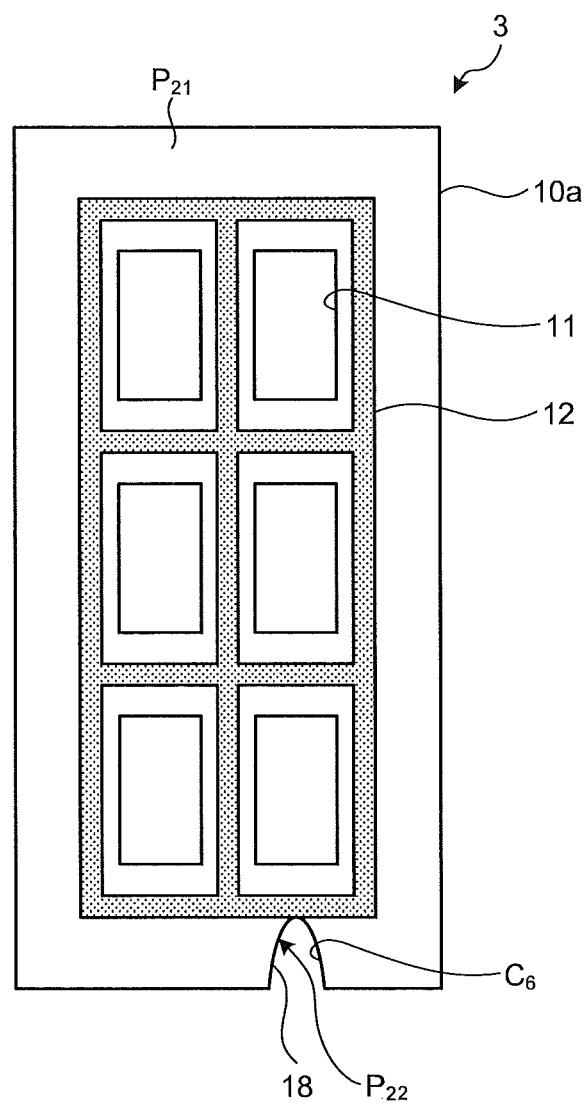
FIG. 25 is a plan view schematically illustrating an analysis chip according to a third construction.

FIG. 25 is a plan view schematically illustrating an analysis chip according to a third construction. In the above-described the first construction, it has been described that the washing liquid on the water repellent surface runs out via the extension portion 13. In an analysis chip 3 in the third construction, however, a cutout portion 18 reaching the partition portion 12 is formed in a substrate $10a$ and the partition portion 12 is in contact with the outer edge of the substrate $10a$. The material of the substrate $10a$ is the same as the material of the above-described substrate 10.

The substrate $10a$ has the cutout portion 18 formed by cutting out a region being a part of the above-described substrate 10 from the outer edge of the substrate 10 to the partition portion 12. A corner portion $C_6$ forming the outer edge of the substrate $10a$ is connected to the partition portion 12 by forming the cutout portion 18. In the third construction, a connection portion connecting the partition portion 12 and the outer edge of the substrate $10a$ is integrally provided with the partition portion 12. In addition, the corner portion in the third construction is an angle formed by a surface $P_{21}$ on which the reaction portions 11 of the substrate $10a$ are provided and a surface $P_{22}$ orthogonal to this surface $P_{21}$ and formed by the cutout portion 18. The surface $P_{21}$ and the surface $P_{22}$ form straight lines with each other in the cross section of the substrate $10a$ and the corner $C_6$ is formed by intersecting these straight lines. Therefore, the effect of efficiently running out the above-described washing liquid 601 on the water repellent surface can be obtained by carrying out the washing process with the edge side on the side of the cutout portion 18 being downward. Consequently, the cutout portion 18 functions as the connecting means.

Similar to the first construction, according to the above-described third construction, sample contamination in the adjacent reaction portions 21 can be avoided and the unreacted labeled substance adhering to the water repellent surface can be efficiently washed out because the analysis chip 3 having the reaction portions 11 has the partition portion 12 partitioning the reaction portions 11 and the a cutout portion 18 formed by cutting out a part of the substrate and connecting the corner portion $C_6$ of the substrate $10a$ and the partition portion 12 by surrounding each of the reaction portions 11 with a water repellent material. The background noise due to the unreacted labeled substance generated after washing can be reduced by this configuration.

Fourth Construction

Figure 26:
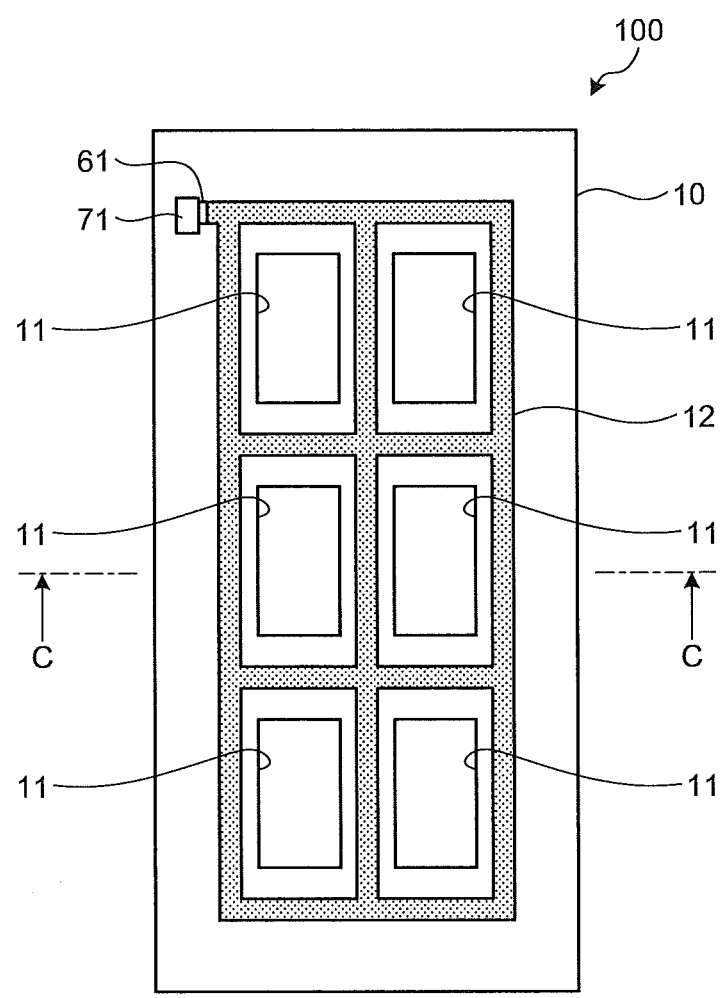
FIG. 26 is a plan view schematically illustrating an analysis chip according to a fourth construction.
Figure 27:
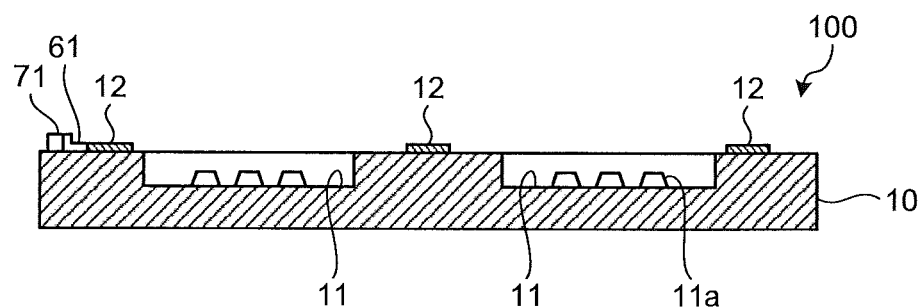
FIG. 27 is a cross-sectional view taken along the line C-C of FIG. 26.
Figure 28:
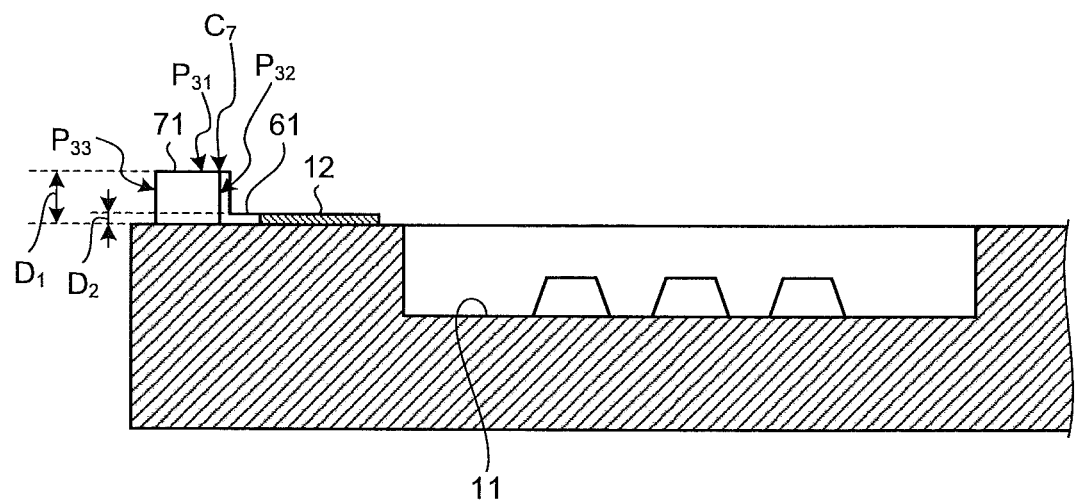
FIG. 28 is a magnified view of a part of FIG. 27.

The analysis chip according to a fourth construction will be described with reference to FIGS. 26 to 28. FIG. 26 is a plan view schematically illustrating an analysis chip according to the fourth construction. FIG. 27 is a cross-sectional view taken along the line C-C of FIG. 26. FIG. 28 is a magnified view of a part of FIG. 27. An analysis chip 100 illustrated in FIGS. 26 to 28 includes a substrate 10 having the reaction portions 11, the partition portion 12, an extension portion 61 being a connection portion, and a projection portion 71.

The extension portion 61 is provided on the main surface of the substrate 10, extends from a part of the partition portion 12 toward the outer edge (the edge side) of the substrate 10, and reaches a corner portion $C_7$ formed by the projection portion 71. The extension portion 61 extends in a strip-like shape and forms a water repellent surface with water repellency. The extension portion 61 is continuous with the partition portion 12. In other words, the water repellent surface of the partition portion 12 and the water repellent surface of the extension portion 61 form a continuous surface. The same water repellent material as or a different water repellent material from the material of the partition portion 12 may be used for the extension portion 61. The extension portion 61, however, is preferably formed by using the same water repellent material from the viewpoint of continuity of the boundary surface. In addition, the extension portion 61 preferably extends linearly with respect to the partition portion 12 from the viewpoint of easily forming the water repellent surface. The water repellent surface formed of the partition portion 12 and the extension portion 61 preferably has a small occupied area to the main surface of the substrate 10 from the viewpoint of reducing the adhering amount of the unreacted labeled substance during washing.

The partition portion 12 and the extension portion 61 can be formed in the same manner as these portions in the above-described first construction.

The projection portion 71 projects from the surface of the substrate 10 on the side where the partition portion 12 is provided in a direction perpendicular to the surface and forms a rectangular shape. In the fourth construction, the corner portion $C_7$ formed by the projection portion 71 is an angle formed by a top surface $P_{31}$ in the projection side and a side surface $P_{32}$ of the reaction portion 11 side among the side surfaces orthogonal to the top surface $P_{31}$. The top surface $P_{31}$ and the side surface $P_{32}$ form straight lines with each other in the cross section of the substrate 10 and the corner portions $C_7$ is formed by intersecting these straight lines. The top surface and the side surface are surfaces that are distinguished from each other with the corner portion as a boundary and side surfaces are also surfaces that are similarly distinguished from each other with the corner portion as a boundary. The extension portion 61 extends from the partition portion 12 to the outside edge forming the corner portion $C_7$.

As illustrated in FIG. 28, the projection portion 71 has a projection length $D_1$ from the substrate 10 longer than a projecting length $D_2$ of the partition portion 12 from the substrate 10. In other words, the projection portion 71 projects from the surface of the substrate 10 as compared with the partition portion 12. In addition, the shape of the corner portion at the top of the projection portion 71 in a projecting direction is not particularly limited and the corner portion preferably forms a right angle. In other words, the projection portion 71 preferably has a prismatic shape.

In the fourth construction, the projection portion 71 is described that the whole surface has hydrophilicity. The surface, however, may have water repellency and part of the surface has hydrophilicity or water repellency. The projection portion 71 is formed by bonding a hydrophilic columnar member made of a material subjected to water repellency to the surface of the substrate 10 or by bonding a sheet-like member, for example, a laminating material. The height of the projection portion 71 can be adjusted by laminating a plurality of sheets of the laminating material.

The analysis chip is characterized in that a part of the water repellent surface (extension portion 61) described above reaches the corner portion $C_7$ of the projection portion 71 projecting from the surface of the substrate 10. The number or the size of the projection portion 71 is not particularly limited and it is sufficient that at least one projection portion 71 is provided and the extension portion 61 extends to the corner portion $C_7$. In addition, in the fourth construction, it is described that the extension portion 61 reaches the corner portion $C_7$. The extension portion 61, however, reaches the corner portion formed by the top surface $P_{31}$ and a side surface $P_{33}$ on the side opposite to the side surface $P_{32}$.

When the analysis chip 100 is pulled up from the washing liquid 601 at the time of washing the analysis chip 100, the orientation of the analysis chip 100 is not particularly limited. The analysis chip 100, however, is preferably pulled up so that the projection portion 71 among the reaction portions 11, the partition portion 12, the extension portion 61, and the projection portion 71 finally pulls out of the liquid. The washing liquid 601 on at least the water repellent surface (the partition portion 12 and the extension portion 61) of the analysis chip 100 can efficiently run out by finally pulling the projection portion 71 out of the liquid. As a result, the unreacted labeled substance adhering to the water repellent surface can be washed off. After pulling up, as described above, the liquid is removed with a paper towel or the like and the analysis chip 100 is entirely immersed again in a container containing a new washing liquid to continue to wash or is transferred to a drying process.

According to the fourth construction described above, sample contamination in the adjacent reaction portions 11 can be avoided and the unreacted labeled substance adhering to the water repellent surface can be efficiently washed off because the analysis chip 100 having reaction portions 11 is formed so that the water repellent surface is formed by the partition portion 12 partitioning the reaction portions 11 and the extension portion 61 extending from a part of the partition portion 12 to the corner portion $C_7$ formed by the projection portion 71 by surrounding each of the reaction portions 11 using the water repellent material and the washing liquid 601 on the water repellent surface runs out via the projection portion 71 provided in the opposite side of the side where the extension portion 61 is connected to the partition portion 12 and projecting in a projection length longer than the projection lengths of the partition portion 12 and the extension portion 61 from the substrate 10. Generation of the background noise due to the unreacted labeled substance generated after washing can be reduced by this configuration.

In addition, in the fourth construction, the projection portion 71 projects from the surface of the substrate 10 and thus the position of the projection portion 71 on the substrate 10 can be easily visually checked. When a laminating material such as a bar code or the like provided on the substrate 10 by attaching or printing is higher than the projection length of the partition portion 12, this laminating material may be used as the projection portion. In this case, when the laminating material has water repellency, this laminating material forms a part of the extension portion 61.

In the above-described fourth construction, it has been described that the reaction portion 11 forms the recessed shape. The shape of the reaction portion 11, however, may be the same flat surface as the plane passing through the main surface of the substrate 10. In this case, the selective binding substance is immobilized on all or part of the surface of the reaction portion.

Modified Example 1 of Fourth Construction

Figure 29:
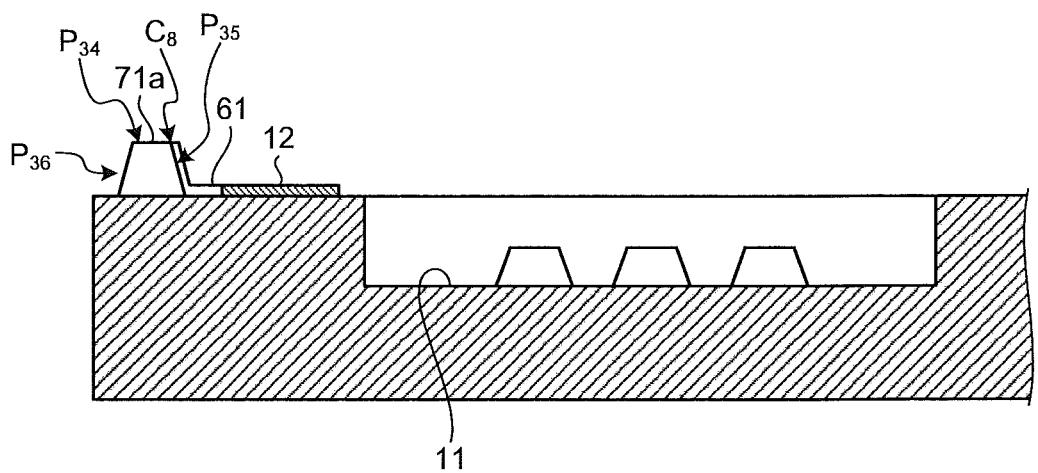
FIG. 29 is a cross-sectional view schematically illustrating an analysis chip according to Modified Example 1 of the fourth construction.

FIG. 29 is a cross-sectional view schematically illustrating an analysis chip according to Modified Example 1 of the fourth construction. It has been described that the projecting portion 71 of the analysis chip 100 according to the fourth construction described above protrudes in a rectangular shape and the side surface extends orthogonal to the surface of the substrate 10. The projection portion 71 may be a projection portion 71a also having a tapered side surface as in the case of Modified Example 1 illustrated in FIG. 29. In Modified Example, a corner portion $C_8$ formed by the projection portion 71a is an angle formed by a top surface $P_{34}$ at the projected top side and an inclined surface $P_{35}$ on the reaction portion 11 side or an inclined surface $P_{36}$ on the opposite side of the inclined surface $P_{35}$ among the inclined surfaces continuous with the top surface $P_{34}$. The top surface $P_{34}$ and the inclined surface $P_{35}$ and $P_{36}$ form straight lines with each other in the cross section of the substrate main body and, for example, the corner portions $C_8$ is formed by intersecting these straight lines. In addition to the projection portion 71a, the projection portion according to the fourth construction may have a shape having an apex at the top such as a pyramid shape.

Modified Example 2 of Fourth Construction

Figure 30:
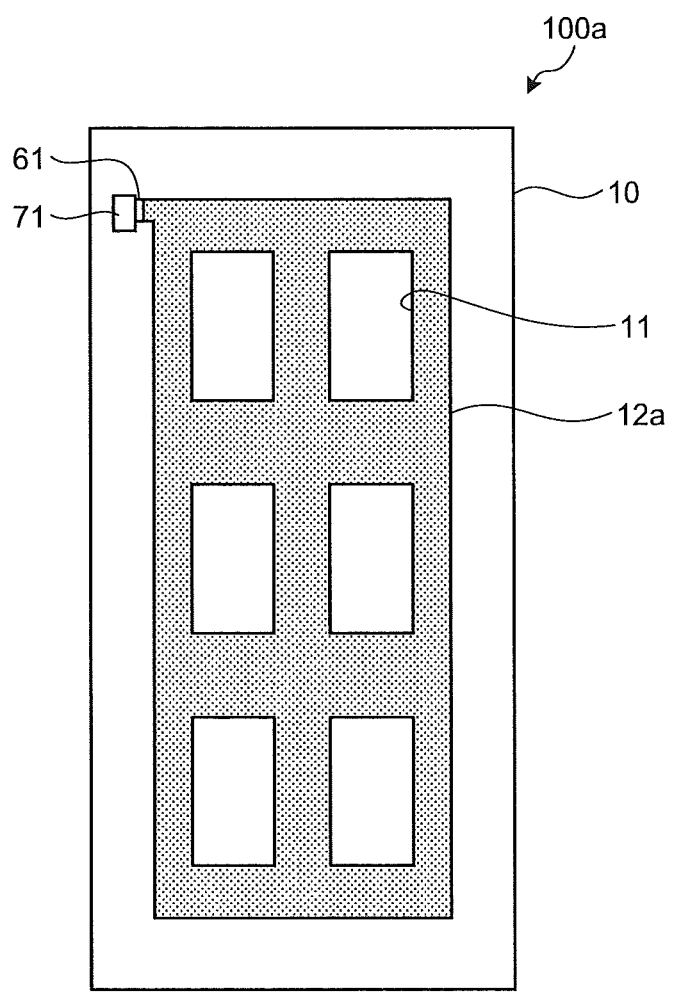
FIG. 30 is a plan view schematically illustrating an analysis chip according to Modified Example 2 of the fourth construction.

FIG. 30 is a plan view schematically illustrating an analysis chip according to Modified Example 2 of the fourth construction. In the above-described fourth construction, it has been described that the partition portion 12 surrounds the reaction portions 11 at a predetermined distance from the outer edge. In Modified Example 2, however, a partition portion 12a is formed in a region continuous with the outer edge of the reaction portions 11 and surrounds reaction portions 11. An analysis chip 100a according to Modified Example 2 is formed in a rectangular region including the outer edge of the reaction portions 11, instead of the above-described partition portion 12 and has a partition portion 12a partitioning the reaction portions 11. Hereinafter, it will be described that the extension portion extends to the corner portion formed by the projection portion in Modified Examples according to the fourth construction as illustrated in FIG. 28.

Modified Example 3 of Fourth Construction

Figure 31:
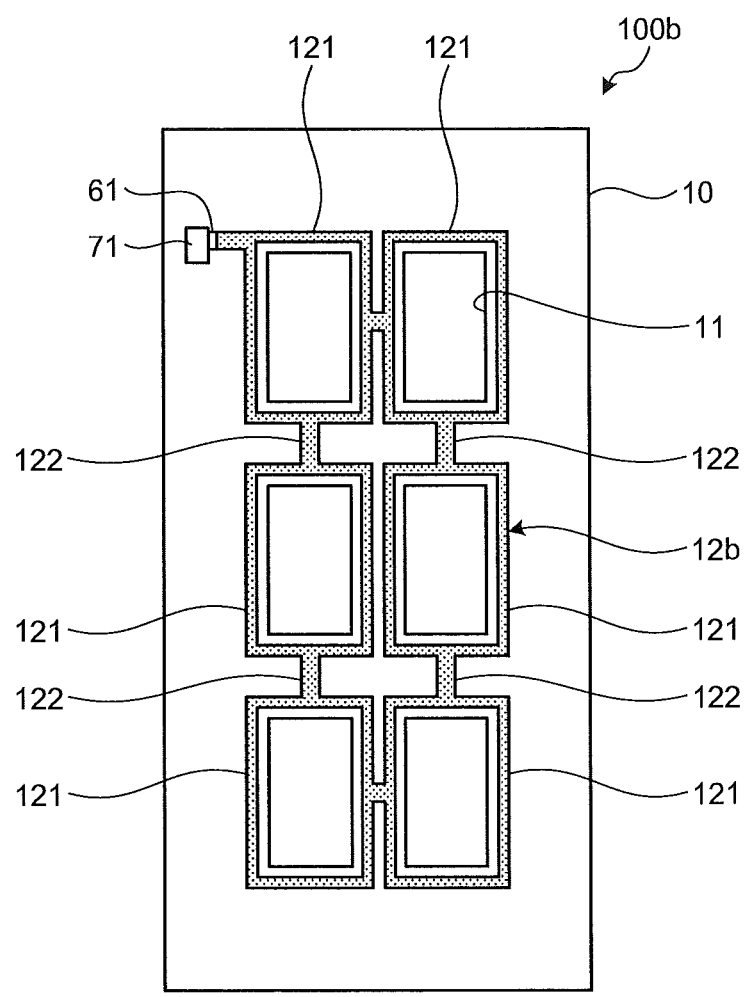
FIG. 31 is a plan view schematically illustrating an analysis chip according to Modified Example 3 of the fourth construction.

FIG. 31 is a plan view schematically illustrating an analysis chip according to Modified Example 3 of the fourth construction. In the above-described fourth construction, it has been described that the reaction portions 11 are partitioned by dividing the inside of the annular frame of the partition portion 12. In Modified Example 3, a partition portion 12b individually surrounds each of the reaction portions 11. An analysis chip 100b according to Modified Example 3 has a partition portion 12b having a plurality of surrounding portions 121 that individually surround the reaction portions 11 and a plurality of coupling portions 122 coupling the surrounding portions 121 to each other, instead of the above-described partition portion 12. Each of the surrounding portion 121 and the coupling portion 122 is formed of the water repellent material.

Modified Example 4 of Fourth Construction

Figure 32:
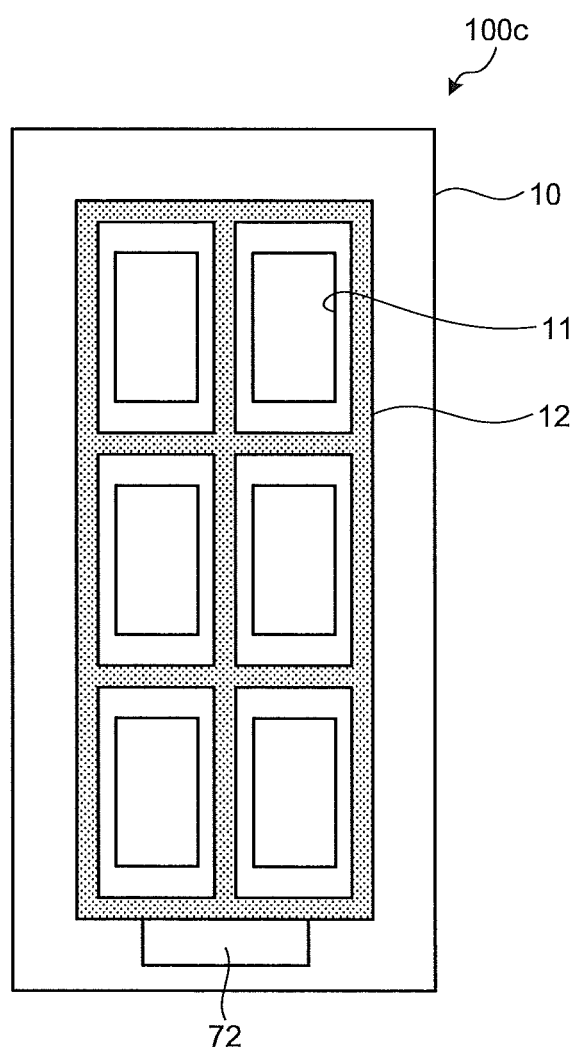
FIG. 32 is a plan view schematically illustrating an analysis chip according to Modified Example 4 of the fourth construction.

FIG. 32 is a plan view schematically illustrating an analysis chip according to Modified Example 4 of the fourth construction. In the above-described fourth construction, it has been described that the analysis chip 100 has an extension portion 61 connecting the partition portion 12 and the projection portion 71. An analysis chip 100c according to Modified Example 4, however, has a projection portion 72 continuous with the water repellent surface by directly contacting to the partition portion 12. In Modified Example 4, it is described that, in the projection portion 72, at least the side surface in contact with the partition portion 12 has water repellency, the water repellent surface forms a connection portion, and the connection portion is integrally provided with the projection portion 72. The projection portion 72 is formed by using, for example, a water repellent laminating material such as a material for a barcode to display information of the analysis chip 100c. In addition, the projection portion 72 according to Modified Example 4 has a larger surface area than that of the above-described projection portion 71. By this configuration, when the analysis chip 100c is pulled up from the washing liquid 601, the state in which a part of the projection portion 72 is in contact with the liquid surface can be more reliably maintained, even if the edge side is somewhat inclined with respect to the liquid surface. The projection portion 72 may be provided instead of the projection portion 71 of the analysis chip 100 described above.

Modified Example 5 of Fourth Construction

Figure 33:
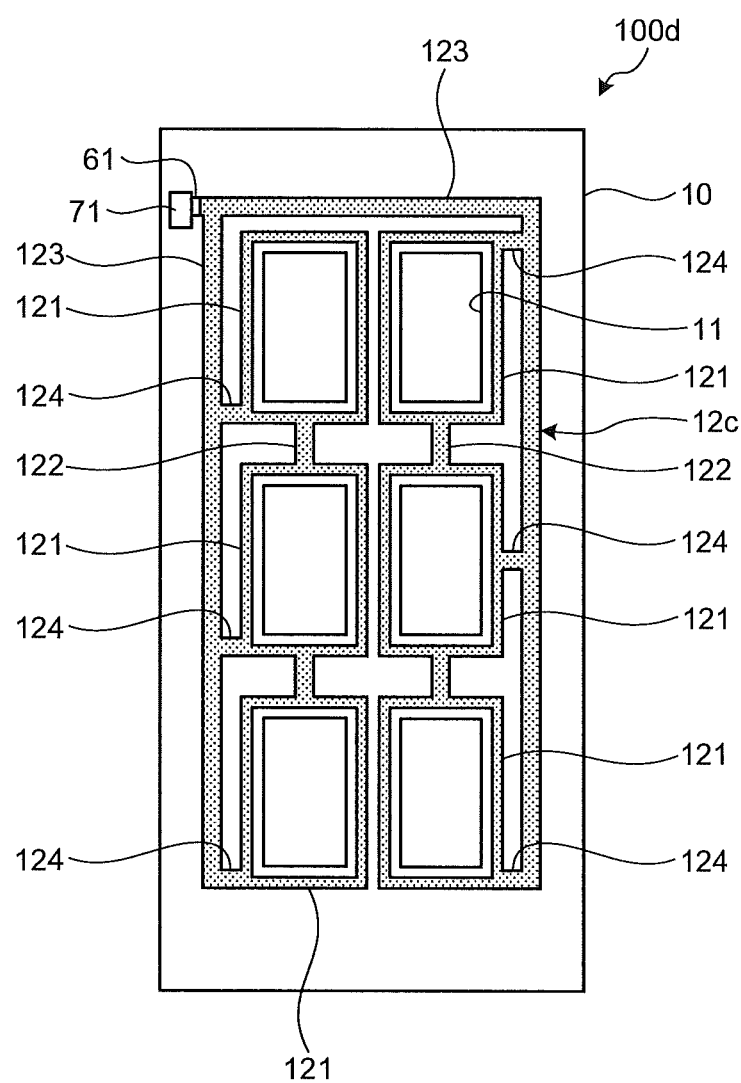
FIG. 33 is a plan view schematically illustrating an analysis chip according to Modified Example 5 of the fourth construction.

FIG. 33 is a plan view schematically illustrating an analysis chip according to Modified Example 5 of the fourth construction. In the above-described Modified Example 3 (refer to FIG. 31), it has been described that the extension portion 61 is connected to one surrounding portion 121 of the partition portion 12b. In Modified Example 5, however, the extension portion 61 is connected to the outer peripheral portion 123 (described below) of the partition portion 12c. An analysis chip 100d according to Modified Example 5 has a plurality of surrounding portions 121 individually surrounding the reaction portions 11, a plurality of coupling portions 122 coupling the surrounding portions 121 to each other, a substantially U-shaped outer peripheral portion 123 that forms the outer periphery of the partition portion 12c and surrounds the reaction portions 11, and a plurality of second coupling portions 124 coupling the surrounding portions 121 and the outer peripheral portion 123, instead of the above-described partition portion 12. In the partition portion 12c, each of the surrounding portions 121 is connected as one water repellent surface by the outer peripheral portions 123 and the second coupling portions 124. The extension portion 61 is connected to a part of the outer peripheral portion 123 of the partition portion 12c.

Modified Example 6 of Fourth Construction

Figure 34:
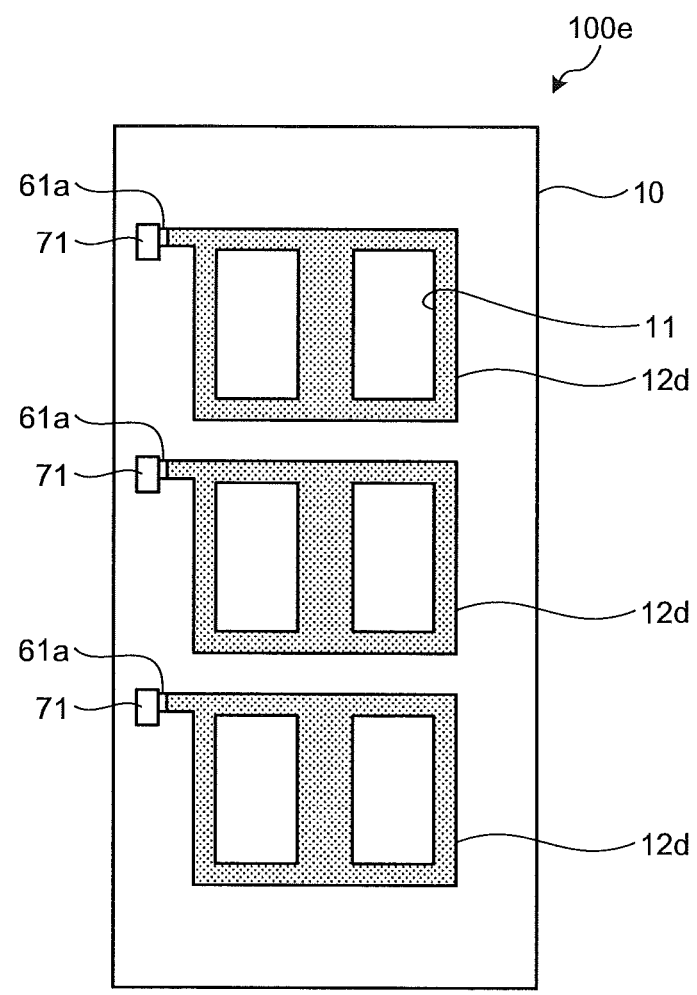
FIG. 34 is a plan view schematically illustrating an analysis chip according to Modified Example 6 of the fourth construction.

FIG. 34 is a plan view schematically illustrating an analysis chip according to Modified Example 6 of the fourth construction. In the above-described fourth construction, it has been described that the partition portion 12 forms one continuous water repellent surface. In Modified Example 6, however, a partition portion is formed of three partition portions 12d surrounding and portioning the two reaction portions 11 as one set. The analysis chip 100e according to Modified Example 6 has the three partition portions 12d surrounding and partitioning the two reaction portions 11 as one set, three extension portions 61a each connected to the partition portions 12d, and the projection portions 71 provided at an end portion in the side different from the side of each of the extension portions 61a connected to the partition portion 12d. Even when the analysis chip 100e has extension portions 61a, the above-described effect can be obtained when each of the extension portions 61a is connected to the same edge side of the substrate 10.

Modified Example 7 of Fourth Construction

Figure 35:
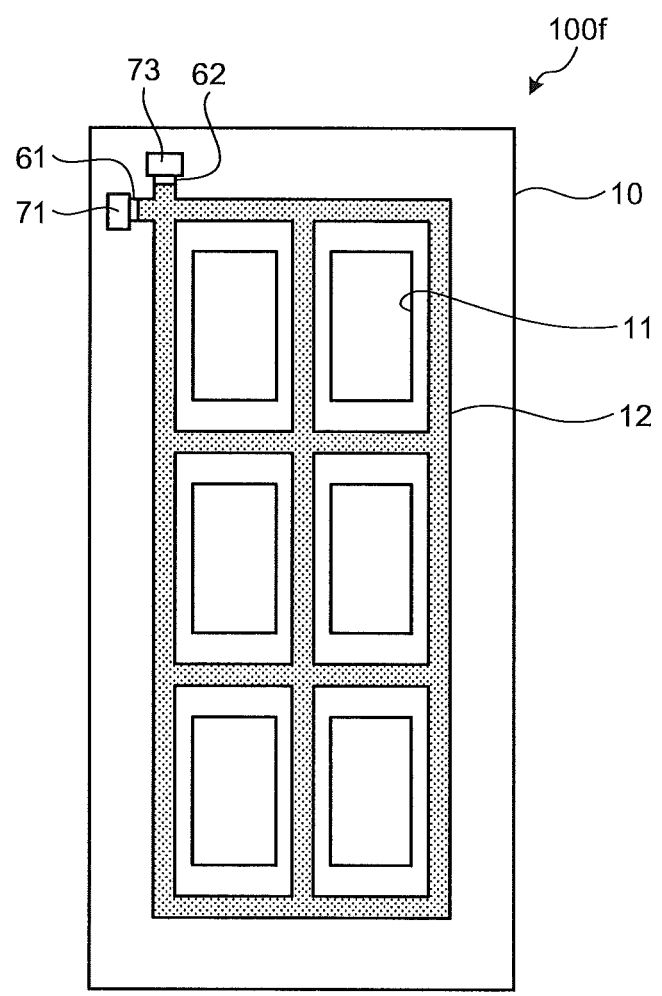
FIG. 35 is a plan view schematically illustrating an analysis chip according to Modified Example 7 of the fourth construction.

FIG. 35 is a plan view schematically illustrating an analysis chip according to Modified Example 7 of the fourth construction. In the above-described fourth construction, it has been described that the extension portion 61 is connected to one edge side of the substrate 10. In Modified Example 7, however, an analysis chip 100f has the extension portion 62 connected to an edge side different from the edge side to which the extension portion 61 is connected, in addition to the extension portion 61. In addition to the configuration of the above-described analysis chip 100, the analysis chip 100f according to Modified Example 7 has the extension portion 62 extending in a direction different from the direction in which the extension portion 61 extends and the projection portion 73 connected to the end portion in the side different from the side where the extension portion 62 is connected to the partition portion 12. The shape and the size of the projection portion 73 may be the same as or different from the shape and the size of the projection portion 71. By forming the extension portion 62, when the analysis chip 100f is pulled up from the washing liquid 601, the edge side where the extension portion 62 (the projection portion 73) is located can also be selected as the edge side to be downward and thus the degree of freedom for pulling up can be increased. In addition, each of the projection portions 71 and 73 are provided facing the edge sides having different lengths, whereby the washing processing can be carried out by changing the orientation of the analysis chip 100f depending on, for example, the size of the opening of the container 600.

Modified Example 8 of Fourth Construction

Figure 36:
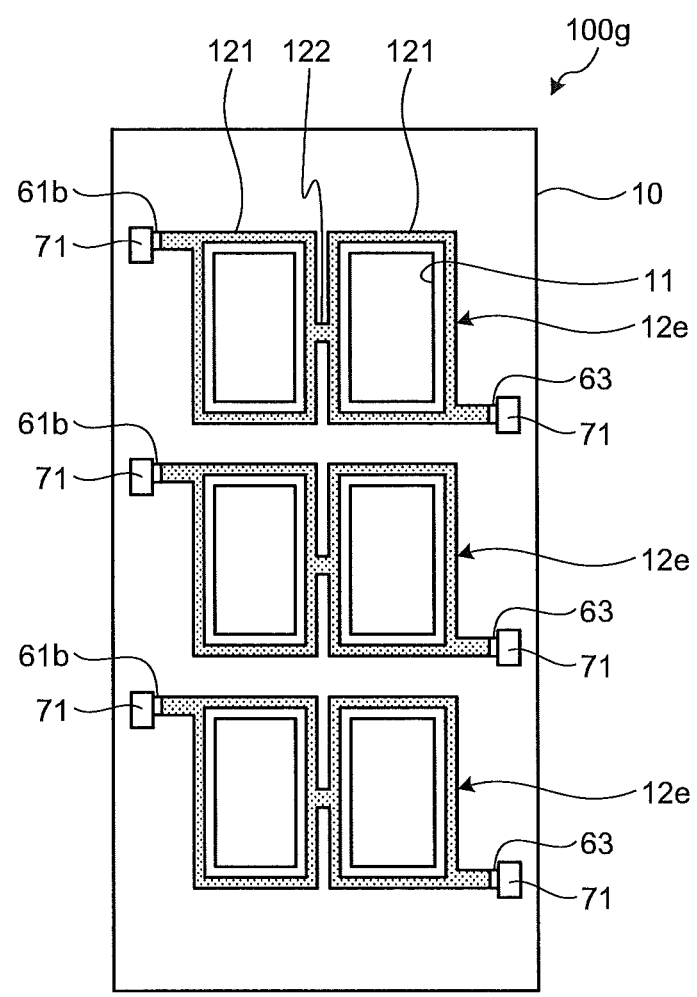
FIG. 36 is a plan view schematically illustrating an analysis chip according to Modified Example 8 of the fourth construction.

FIG. 36 is a plan view schematically illustrating an analysis chip according to Modified Example 8 of the fourth construction. In the above-described Modified Example 6, it has been described that the partition portions are formed of the three partition portions 12d surrounding and partitioning the two reaction portions 11 as one set and the extension portions 61a extend from each of the partition portions. In Modified Example 8, however, the extension portions extend from both directions of each of the partition portions and are connected to the projection portions. An analysis chip 100g according to Modified Example 8 has three partition portions 12e surrounding and partitioning the two reaction portions 11 as one set, three extension portions 61b extending from the partition portions 12e to one outer edge of the substrate 10, and three extension portions 63 extending from the partition portions 12e to one outer edge of the substrate 10 facing the outer edge to which the extension portion 61b is connected. The partition portion 12e has the surrounding portions 121 surrounding the reaction portions 11 and the coupling portions 122 coupling the adjacent surrounding portions 121 to each other. The extension portion 61b may be connected to the partition portion 12d according to Modified Example 6 (refer to FIG. 34).

Modified Example 9 of Fourth Construction

Figure 37:
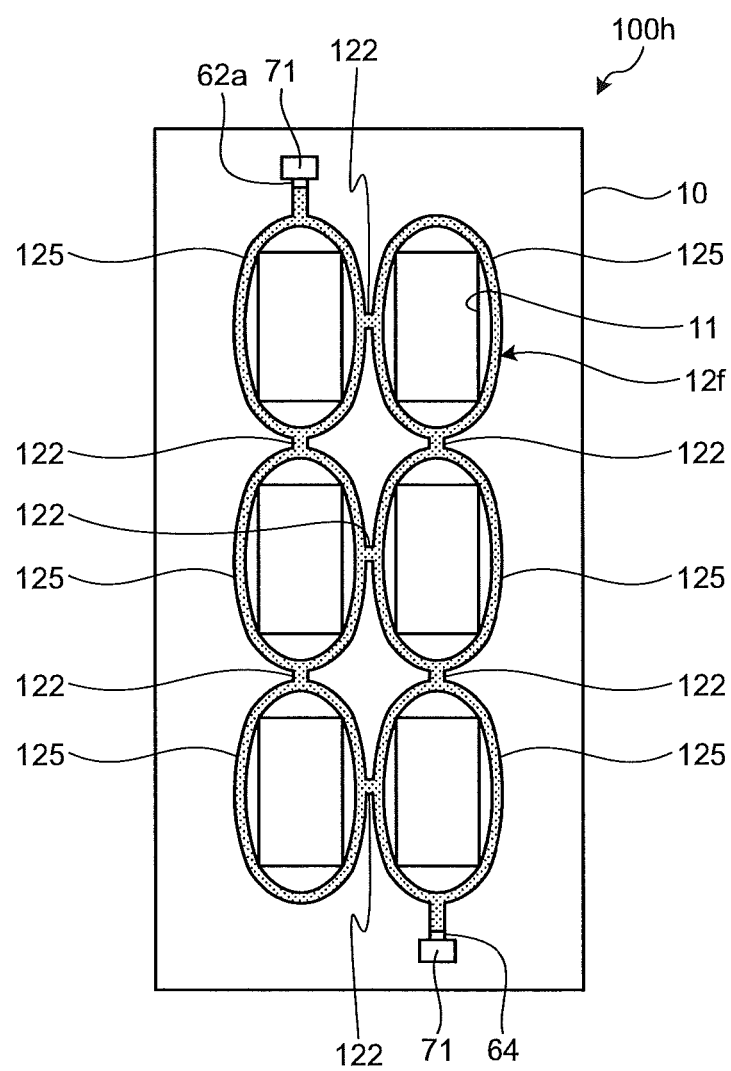
FIG. 37 is a plan view schematically illustrating an analysis chip according to Modified Example 9 of the fourth construction.

FIG. 37 is a plan view schematically illustrating an analysis chip according to Modified Example 9 of the fourth construction. In the above-described Modified Example 3 (refer to FIG. 31), it has been described that the surrounding portions 121 forms a rectangular annular shape and surrounds the reaction portions 11. In Modified Example 9, however, surrounding portions in an elliptical annular shape surround the reaction portions 11. An analysis chip 100h according to Modified Example 9 has a plurality of surrounding portions 125 that individually surround the reaction portion 11, a partition portion 12f having a plurality of coupling portions 122 coupling the surrounding portions 125 to each other, an extension portion 62a extending from one surrounding portion 125 among the surrounding portions 125 to the edge side of the substrate 10, an extension portion 64 extending from an different surround-ing portion 125 from this surrounding portion 125 in an opposite direction to the extension portion 62a, and two projection portions 71 each connected to the extension portion 62a and 64. In addition to the surrounding portion 125 that forms an elliptical annular shape surrounding the reaction portion 11 in Modified Example 9, the surrounding portion may be a surrounding portion forming a circular shape or a polygonal shape surrounding the reaction portion.

Modified Example 10 of Fourth Construction

Figure 38:
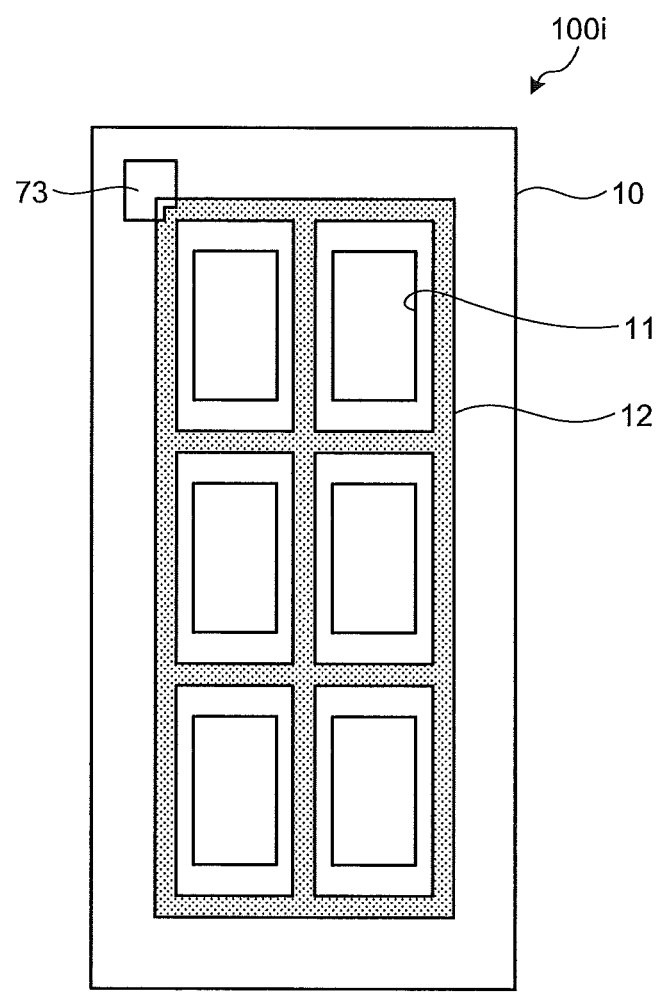
FIG. 38 is a plan view schematically illustrating an analysis chip according to Modified Example 10 of the fourth construction.

FIG. 38 is a plan view schematically illustrating an analysis chip according to Modified Example 10 of the fourth construction. In the above-described Modified Example 4 (refer to FIG. 32), it has been described that the projection portion 72 is continuous with the water repellent surface by contacting the linear portion of the outer periphery of the partition portion 12. In Modified Example 10, however, a projection portion 73 is continuous with the water repellent surface by providing the projection portion 73 at the corner portion of the outer periphery of the partition portion 12. An analysis chip 100i according to Modified Example 10 has a projection portion 73 provided at a corner portion formed by the rectangle of the partition portion 12 and connected to the water repellent surface. Similar to Modified Example 4 described above, in Modified Example 10, it is described that, in the projection portion 73, at least the side surface in contact with the partition portion 12 has water repellency, the water repellent surface forms a connection portion, and the connection portion is integrally provided with the projection portion 73. As in Modified Example 10, the projection portion 73 may be connected to the corner portion of the partition portion 12 to be connected to two orthogonal straight line portions of the partition portion 12. According to Modified Example 10, the analysis chip can be pulled up with the different edge sides of the substrate 10 being downward as well as can be pulled up with the corner of the substrate 10 being downward.

Modified Example 11 of Fourth Construction

Figure 39:
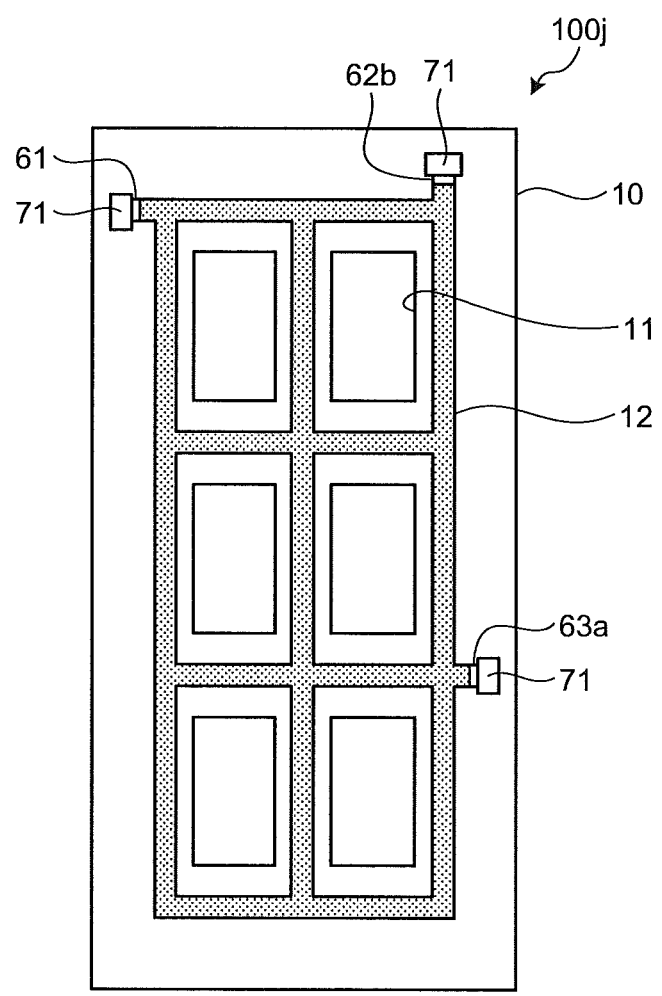
FIG. 39 is a plan view schematically illustrating an analysis chip according to Modified Example 11 of the fourth construction.

FIG. 39 is a plan view schematically illustrating an analysis chip according to Modified Example 11 of the fourth construction. In the above-described fourth construction, it has been described that the extension portion 61 extends toward one edge side of the substrate 10. In Modified Example 11, however, extension portions 62b and 63a extend toward different edge sides from each other in addition to the extension portion 61. In addition to the configuration of the above-described analysis chip 100, an analysis chip 100j according to Modified Example 11 has an extension portion 62b connected to an edge side different from and orthogonal to the edge side intersecting with the orientation direction of the extension portion 61, and an extension portion 63a extending toward an edge side different from and facing the edge side intersecting with the orientation direction of the extension portion 61. By forming the extension portions 62b and 63a, when the analysis chip 100j is pulled up from the washing liquid 601, any one of the edge sides where the projection portions connected to the extension portions 61, 62b, and 63a are located can be selected as the lower edge side and thus the degree of freedom for pulling up can be increased.

Modified Example 12 of Fourth Construction

Figure 40:
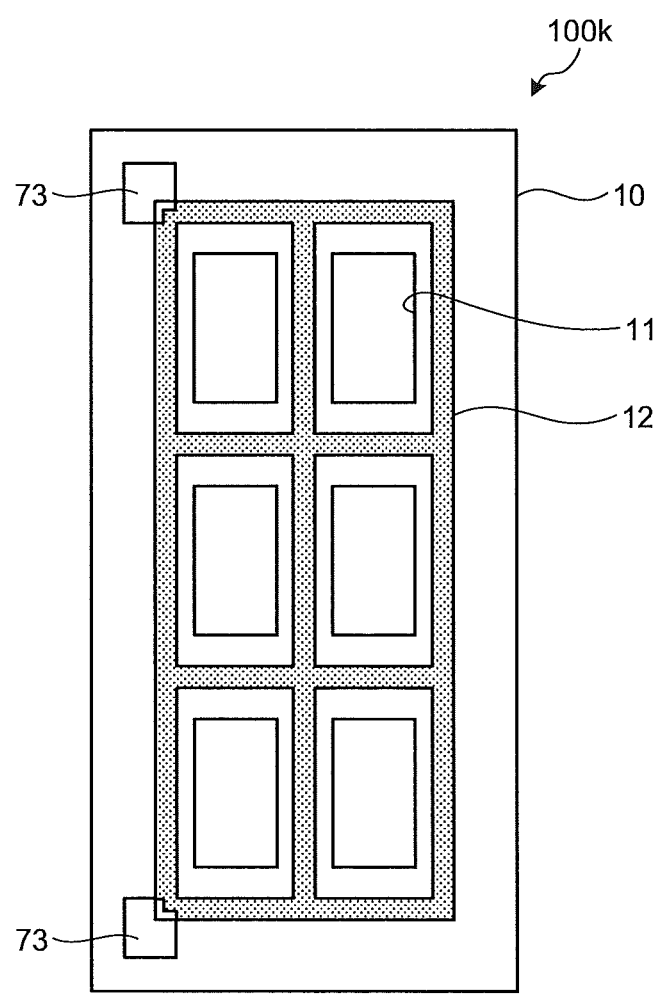
FIG. 40 is a plan view schematically illustrating an analysis chip according to Modified Example 12 of the fourth construction.

FIG. 40 is a plan view schematically illustrating an analysis chip according to Modified Example 12 of the fourth construction. In Modified Example 12, a projection portion is also provided at a different corner in addition to the projection portion of the above-described Modified Example 10 (refer to FIG. 38). In an analysis chip 100k according to Modified Example 12, projection portions 73 are provided at two corner portions among the corner portions formed in the rectangular of the partition portion 12 with respect to the above-described analysis chip 100i. According to Modified Example 12, the analysis chip can be pulled up with the different edge sides of the substrate 10 being downward as well as can be pulled up with the corner of the substrate 10 being downward.

Modified Example 13 of Fourth Construction

Figure 41:
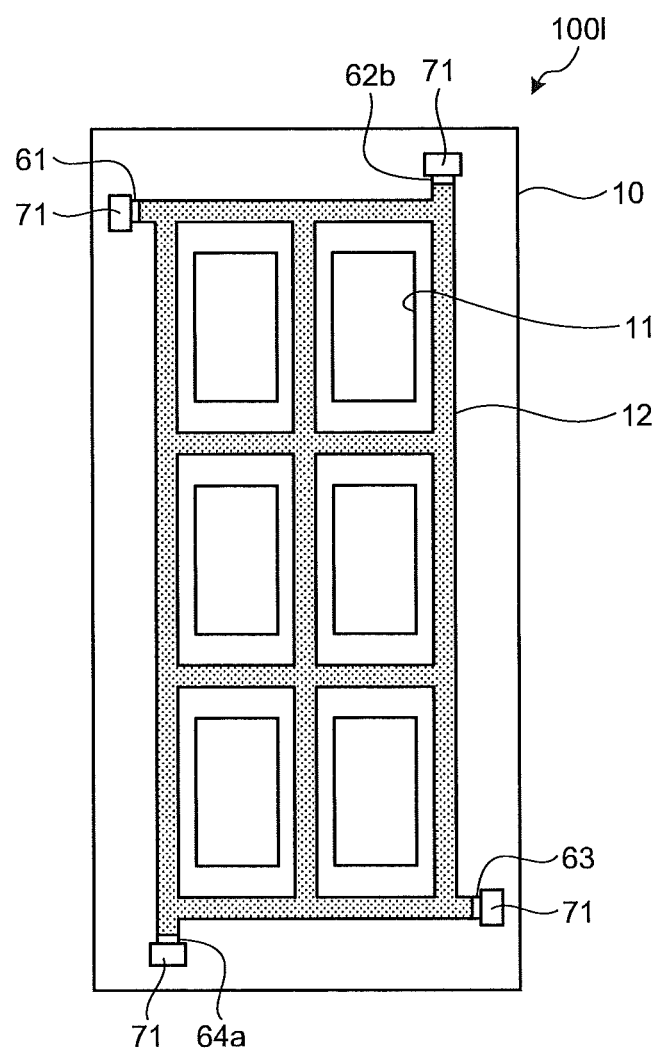
FIG. 41 is a plan view schematically illustrating an analysis chip according to Modified Example 13 of the fourth construction.

FIG. 41 is a plan view schematically illustrating an analysis chip according to Modified Example 13 of the fourth construction. In the above-described fourth construction, it has been described that the extension portion 61 extends toward one edge side of the substrate 10. In Modified Example 13, however, an analysis chip 100l has extension portions 62b, 63, and 64a each extending toward different edge sides from each other and the projection portions 71 each connected to the extension portions 62b, 63, and 64a, in addition to the extension portion 61. In other words, in addition to the configuration of the above-described analysis chip 100, the analysis chip 100l according to Modified Example 13 has three extension portions 62b, 63, and 64a each connected to different edge sides from each other and the projection portions 71 each connected to the extension portions 62b, 63, and 64a. By forming the extension portions 61, 62b, 63, and 64a, when the analysis chip 100l is pulled up from the washing liquid 601, the washing treatment can be carried out without noticing the orientation of the edge side to be downward due to existence of projection portions 71 at the sides of four edge sides of the substrate 10.

Modified Example 14 of Fourth Construction

Figure 42:
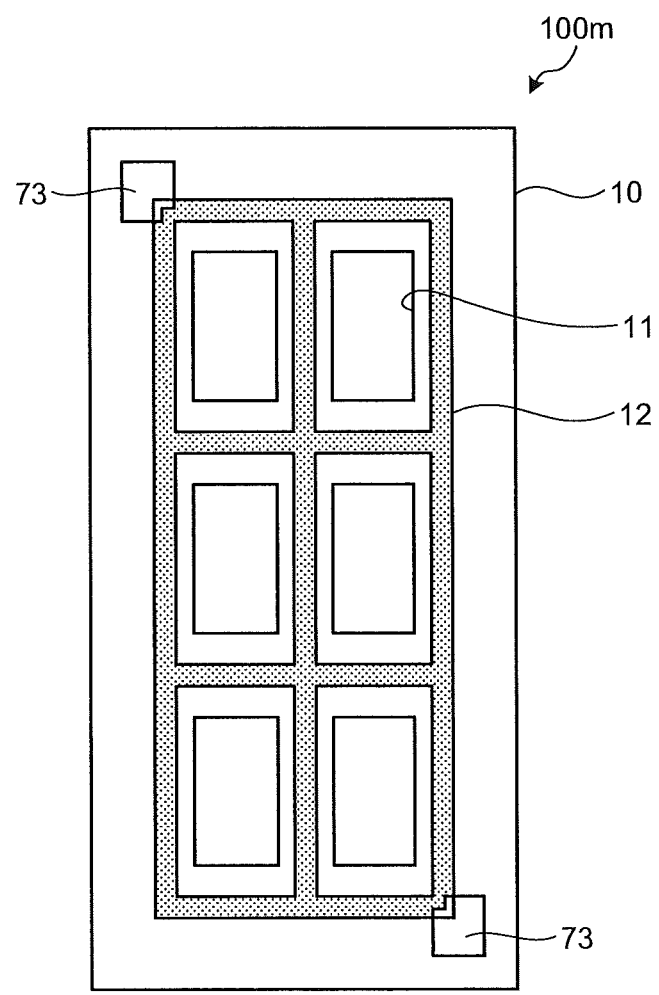
FIG. 42 is a plan view schematically illustrating an analysis chip according to Modified Example 14 of the fourth construction.

FIG. 42 is a plan view schematically illustrating an analysis chip according to Modified Example 14 of the fourth construction. In the above-described Modified Example 12, it has been described that the projection portions 73 are provided at the corner portions adjacent to each other in the partition portion 12. An analysis chip 100 m according to Modified Example 14 has two projection portions 73 each provided at corner portions facing each other of the partitioning portion 12. By providing the two projection portions 73 at the corner portions facing each other of the partition portion 12, when the analysis chip 100m is pulled up from the washing liquid 601, the washing treatment can be carried out without noticing the orientation of the edge side to be downward.

Modified Example 15 of Fourth Construction

Figure 43:
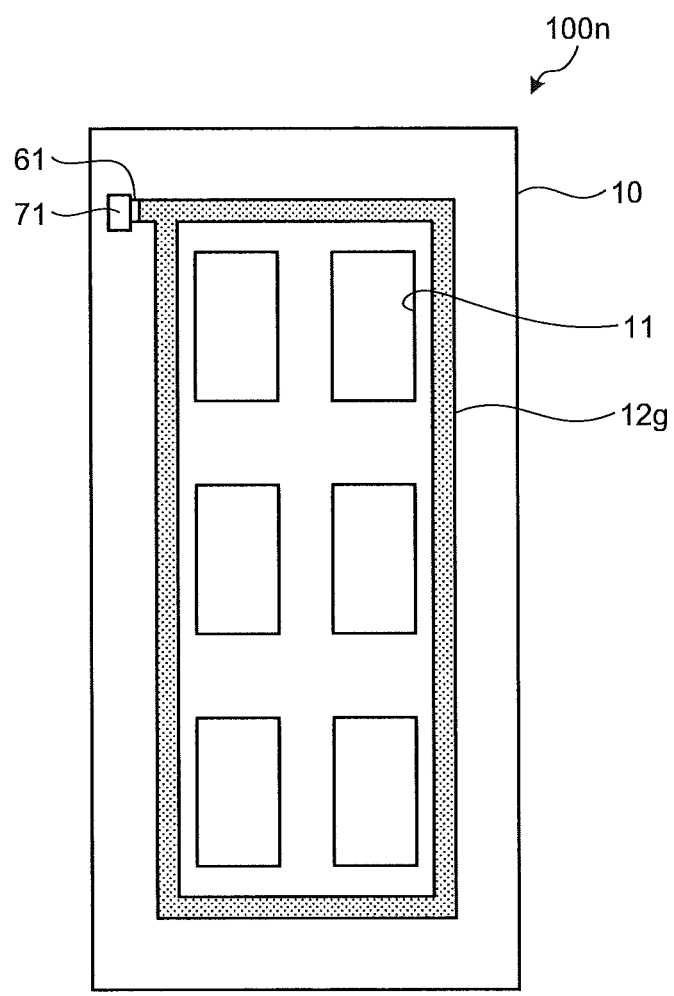
FIG. 43 is a plan view schematically illustrating an analysis chip according to Modified Example 15 of the fourth construction.

FIG. 43 is a plan view schematically illustrating an analysis chip according to Modified Example 15 of the fourth construction. In the above-described fourth construction and Modified Examples 1 to 14, it has been described that the partition portion individually partitions each of the reaction portions. An analysis chip 100n according to Modified Example 15, however, has a partition portion 12g collectively surrounds the reaction portions 11. As in the partition portion 12g, the partition portion may collectively surround the reaction portions 11 to prevent the leakage of the sample from the substrate 10.

Modified Example 16 of Fourth Construction

Figure 44:
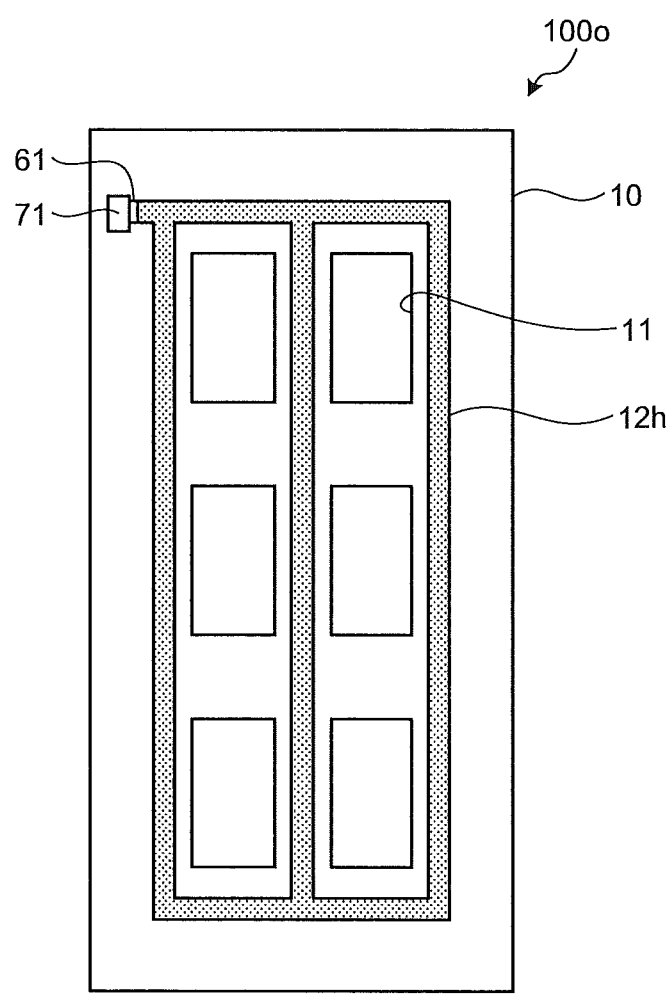
FIG. 44 is a plan view schematically illustrating an analysis chip according to Modified Example 16 of the fourth construction.

FIG. 44 is a plan view schematically illustrating an analysis chip according to Modified Example 16 of the fourth construction. In addition to the above-described Modified Example 15 (refer to FIG. 43), as in the analysis chip 100o according to Modified Example 16, the partition portion may be a partition portion 12h surrounding each of the predetermined number of the reaction portions 11 (three reaction portions in Modified Example 16).

Modified Example 17 of Fourth Construction

Figure 45:
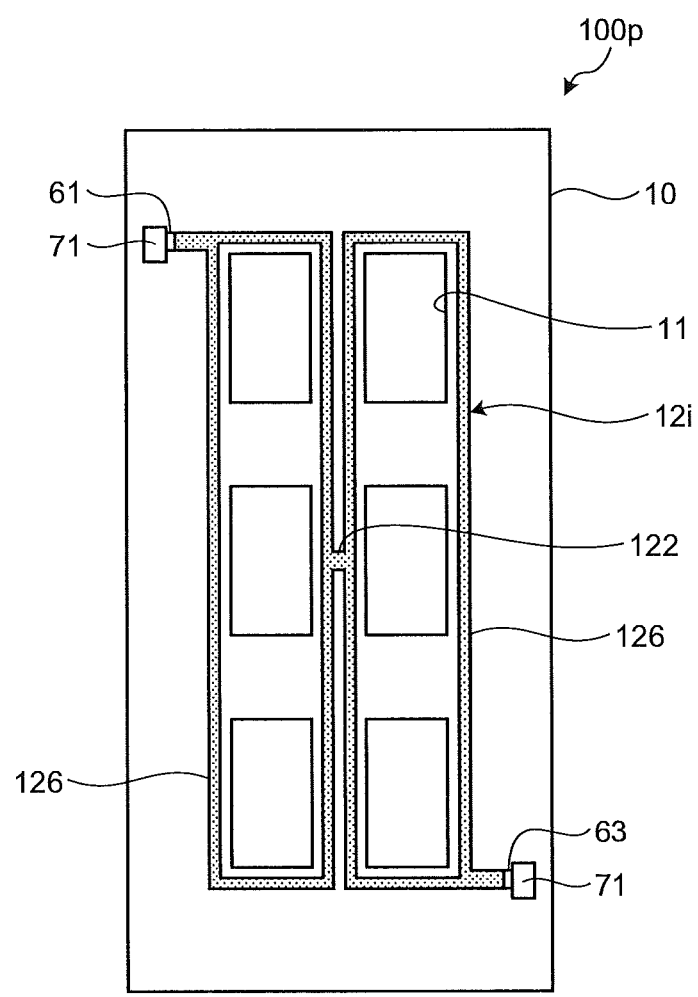
FIG. 45 is a plan view schematically illustrating an analysis chip according to Modified Example 17 of the fourth construction.

FIG. 45 is a plan view schematically illustrating an analysis chip according to Modified Example 17 of the fourth construction. With respect to the above-described Modified Example 16 (refer to FIG. 44), as in an analysis chip 100p according to Modified Example 17, the analysis chip 100p may be an analysis chip having the two surrounding portions 126 each surrounding the predetermined number of the reaction portions 11 (three reaction portions in Modified Example 17), a partition portion 12i having a coupling portion 122 coupling the surrounding portions 126 to each other, extension portions 61 and 63 each extending from the partition portion 12i to different edge sides from each other of the substrate 10, and the two projection portions 71 connected to the end portions opposite to the side where the extension portions 61 and 63 are connected to the partition portions 12i.

Modified Example 18 of Fourth Construction

Figure 46:
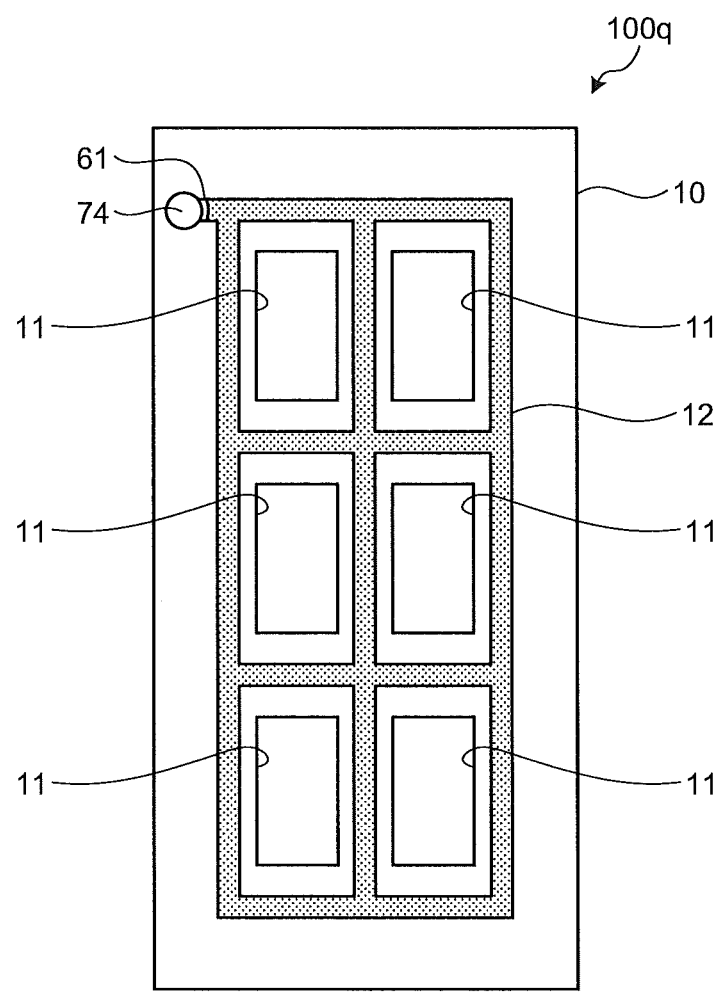
FIG. 46 is a plan view schematically illustrating an analysis chip according to Modified Example 18 of the fourth construction.

FIG. 46 is a plan view schematically illustrating an analysis chip according to Modified Example 18 of the fourth construction. It has been described that, in the projection portion 71 of the analysis chip 100 according to the above-described fourth construction, the shape of the upper surface is a rectangular shape. However, the shape is not limited to the rectangular shape and as in a projection portion 74 of an analysis chip 100q according to Modified Example 18, the upper surface of the projection portion 74 may form a circular shape. In the projection portion 74, a corner portion is formed by the upper surface and the side surface continuous with the upper surface. The extension portion 61 extends from the partition portion 12 to the corner portion along the side surface forming the curved surface.

Modified Example 19 of Fourth Construction

Figure 47:
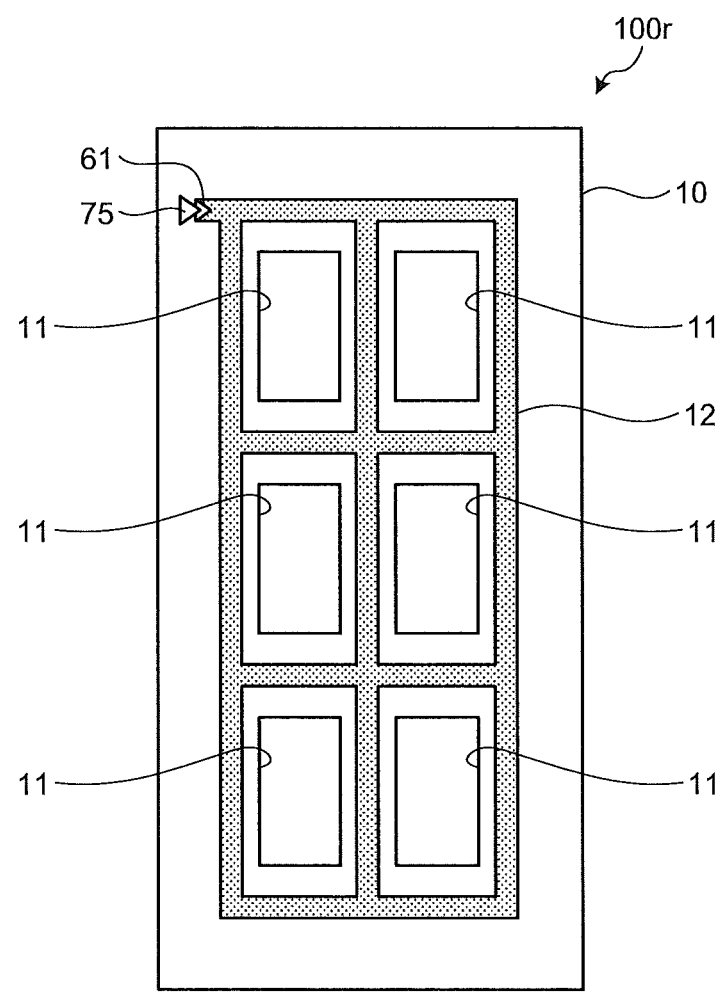
FIG. 47 is a plan view schematically illustrating an analysis chip according to Modified Example 19 of the fourth construction.

FIG. 47 is a plan view schematically illustrating an analysis chip according to Modified Example 19 of the fourth construction. In addition to the projection portion 74 according to Modified Example 18 described above, the projection portion may be a projection portion 75 in which the upper surface forms a triangular shape as in the projection portion 75 of an analysis chip 100r according to Modified Example 19. In the projection portion 75, a corner portion is formed by the upper surface and any one of the three side surfaces connected to the upper surface. The extension portion 61 extends from the partition portion 12 to this corner portion along the side surface.

Fifth Construction

Figure 48:
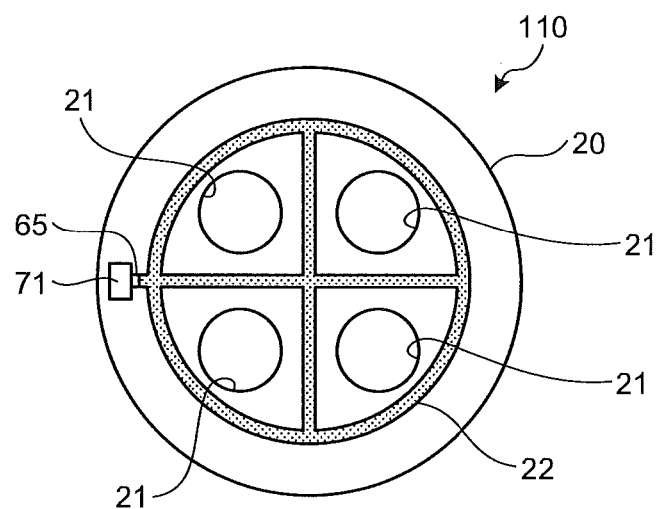
FIG. 48 is a plan view schematically illustrating an analysis chip according to a fifth construction.

FIG. 48 is a plan view schematically illustrating an analysis chip according to an fifth construction. In the above-described fourth construction, it has been described that the substrate 10 is a flat plate the main surface of which forms a rectangular shape. An analysis chip 110 according to the fifth construction, however, includes a planar substrate 20 having a plurality of reaction portions 21 (four reaction portions in the fifth construction), a partition portion 22, an extension portion 65, and a projection portion 71 and is provided with a flat plate-like substrate 20 the main surface of which is a circular shape. The material of the substrate 20 is the same as the material of the above-described substrate 10.

A plurality of recessed reaction portions 21 are formed on one main surface of the substrate 20. The reaction portion 21 is composed of a bottom surface and a wall surface connecting the bottom surface and the main surface of the substrate 20. The selective binding substance is immobilized in the hollow space formed by the bottom surface and the wall surfaces. Similar to the reaction portion 11, the reaction portion 21 has a plurality of protrusion portions protruding from the bottom surface in a protruding shape.

The partition portion 22 is provided on the main surface of the substrate 20 and partitions the reaction portions 21 by surrounding each of the reaction portions 21 with a water repellent material. The partition portion 22 forms a circular ring outer periphery, forms independent partitions for each of reaction portions 21, and forms a water repellent surface having a surface with water repellency.

The extension portion 65 is provided on the main surface of the substrate 20, extends from a part of the partition portion 22 toward the outer edge (the edge side) of the substrate 20, and is connected to the projection portion 71 at the end portion opposite to the side connected to the partition portion 22. The extension portion 65 extends in a strip-like shape and forms a water repellent surface having water repellency. The extension portion 65 is continuous with the partition portion 22. In other words, the water repellent surface of the partition portion 22 and the water repellent surface of the extension portion 65 form a continuous surface. The partition portion 22 and the extension portion 65 are formed using the same water repellent material and method as the material and the method of the partition portion 12 and the extension portion 61 described above.

Similar to the first construction, according to the fifth construction described above, sample contamination in the adjacent reaction portions 11 can be avoided and the unreacted labeled substance adhering to the water repellent surface can be efficiently washed off because the analysis chip 110 having the reaction portions 21 is formed so that the water repellent surface is formed by the partition portion 22 partitioning the reaction portions 21 and the extension portion 65 extending from a part of the partition portion 22 to an outer edge (an edge side) of the substrate 20 by surrounding each of the reaction portions 11 using the water repellent material and the washing liquid 601 on the water repellent surface runs out via the projection portion 71 provided at the end portion opposite to the side where the extension portion 65 is connected to the partition portion 22. Generation of the background noise due to the unreacted labeled substance generated after washing can be reduced by this configuration.

Sixth Construction

Figure 49:
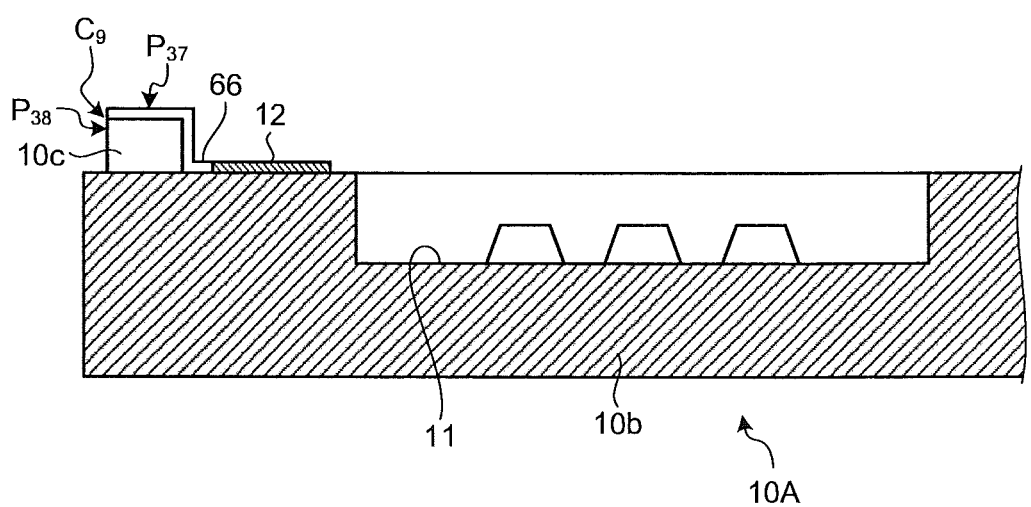
FIG. 49 is a cross-sectional view schematically illustrating an analysis chip according to a sixth construction.

FIG. 49 is a cross-sectional view schematically illustrating an analysis chip according to a sixth construction and a view illustrating the configuration of the main part of the analysis chip corresponding to FIG. 28. In the above-described fourth construction, it has been described that the projection portion 71 is formed by bonding the member formed separately from the substrate 10. An analysis chip of the sixth construction has a projection portion integrally provided with the substrate main body. The analysis chip illustrated in FIG. 49 has a substrate 10A, a partition portion 12, and an extension portion 66. The material of the substrate 10A is the same as the material of the above-described substrate 10.

The substrate 10A has a plate-like main body portion 10b (substrate main body) having the same shape as the above-described substrate 10 and provided with the reaction portions 11, the partition portion 12, and the extension portion 66 described above and a projection portion 10c extending from the surface of the main body portion 10b in a direction orthogonal to the surface. In the sixth construction, a corner portion $C_9$ formed by the projection portion 10c is an angle formed by a top surface $P_{37}$ in the projected top side and a side surface $P_{38}$ opposite to the reaction portion 11 side among the side surfaces orthogonal to the top surface $P_{37}$. The top surface $P_{37}$ and the side surface $P_{38}$ form straight lines with each other in the cross section of the substrate 10A and the corner portions $C_9$ is formed by intersecting these straight lines. The entire side surface of the projection portion 10c may have water repellency.

The extension portion 66 is formed using the water repellent material, extends from the partition portion 12, further extends along the side surface and the top surface $P_{37}$ of the projection portion 10c, and reaches the above-described corner portion $C_9$.

According to the sixth construction described above, sample contamination in the adjacent reaction portions 11 can be avoided and the unreacted labeled substance adhering to the water repellent surface can be efficiently washed off because the analysis chip having the projection portion 10c integrally provided with the main body portion 10b and the reaction portions 11 is formed so that the water repellent surface is formed by the partition portion 12 partitioning the reaction portions 11 and the extension portion 66 extending from a part of the partition portion 12 to the corner portion $C_9$ formed by the projection portion 10c by surrounding each of the reaction portions 11 using the water repellent material and the washing liquid 601 on the water repellent surface runs out via the corner portion $C_9$ of the projection portion 10c integrally provided with the main body portion 10b of the substrate 10A and connected to the end portion opposite to the side where the extension portion 66 is connected to the partition portion 12. Generation of the background noise due to the unreacted labeled substance generated after washing can be reduced by this configuration.

Seventh Construction

Figure 50:
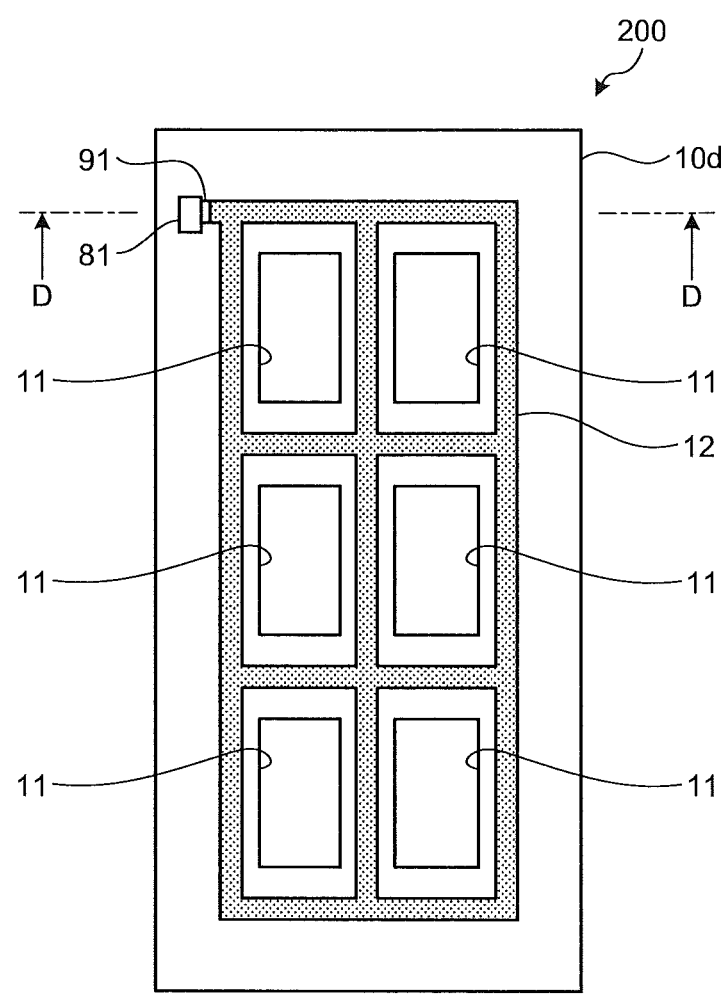
FIG. 50 is a plan view schematically illustrating an analysis chip according to a seventh construction.
Figure 51:
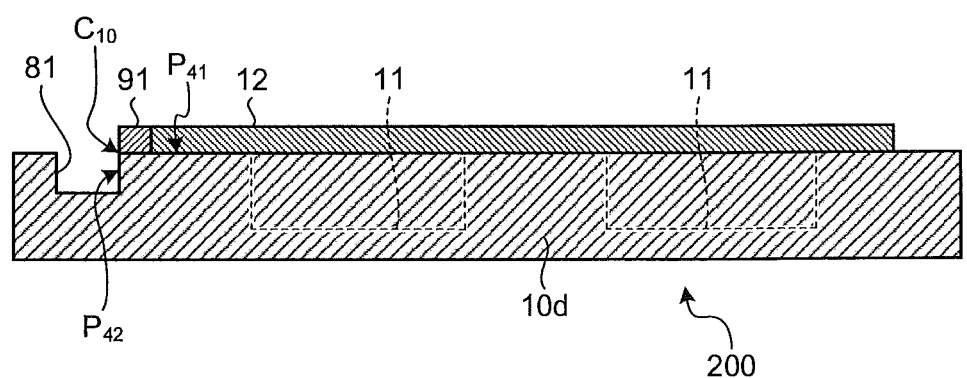
FIG. 51 is a cross-sectional view taken along the line D-D of FIG. 50.

FIG. 50 is a plan view schematically illustrating an analysis chip according to a seventh construction. FIG. 51 is a cross-sectional view taken along the line D-D of FIG. 50. In the above-described fourth construction, it has been described that the analysis chip has the projection portion 71 projecting from the substrate 10. An analysis chip 200 of the sixth construction, however, has a recessed portion 81 provided in the substrate main body and forming a shape in which a part of the substrate main body is recessed. The analysis chip 200 according to the seventh construction has a plurality of reaction portions 11 (six reaction portions in the seventh construction), a partition portion 12, a recessed portion 81, and an extension portion 91 being a connection portion and provided with a flat plate-like substrate 10$d$ the main surface of which forms a rectangular shape. The recessed portion 81 forms a shape recessed from the surface of the substrate 10 on the side where the partition portion 12 is provided, in a direction orthogonal to the surface. The material of the substrate 10$d$ is the same as the material of the above-described substrate 10. In FIG. 51, the positions of the reaction portions 11 in the substrate 10$d$ are exemplified by dashed lines.

The shape of the recessed portion 81 is not particularly limited. Example of the shape may include a rectangular column or truncated pyramid in which the outer peripheral shape of the opening portion and the bottom surface of the recessed portion is a polygonal shape such as a quadrangular shape and a hexagonal shape, a cylinder or truncated cone in which the outer peripheral shape of the opening portion and the bottom surface of the recessed portion is a circular shape or an elliptical shape, a pyramid in which the outer peripheral shape of the opening portion is a polygonal shape, a cone in which the outer peripheral shape of the opening portion is a circular shape or an elliptical shape, and a hemispheric shape.

The substrate 10$d$ has a similar shape to the above-described substrate 10 and has the substrate main body provided with the reaction portions 11 and the partition portion 12 described above, the recessed portion 81 recessed from the surface of the main body portion 10$d$, and the extension portion 91 being a connection portion formed with the water repellent material and connecting the partition portion 12 and the recessed portion 81.

The extension portion 91 is connected to a part of a corner portion $C_{10}$ being a part of the opening end of the recessed portion 81 to the side close to the partition portion 12. The corner portion $C_{10}$ according to the seventh construction is an angle formed by a surface $P_{41}$ of the substrate 10$d$ and a side surface $P_{42}$ being the side surface of the recessed portion 81 on the side close to the partition portion 12.

According to the seventh construction described above, sample contamination in the adjacent reaction portions 11 can be avoided and the unreacted labeled substance adhering to the water repellent surface can be efficiently washed off because the extension portion 91 forms a water repellent surface extending from a part of the partition portion 12 toward the outer edge (the edge side) of the substrate 10$d$ and extends to the corner portion $C_{10}$ formed by a part of the opening end of the recessed portion 81 at the side close to the partition portion 12 and the surface of the substrate 10$d$. Generation of the background noise due to the unreacted labeled substance generated after washing can be reduced by this configuration.

In the seventh construction described above, the water repellent surface may be connected to the opening end of the recessed portion 81 by arranging the partition portion 12 and the recessed portion 81 in a similar manner to Modified Example 4 illustrated in FIG. 32. In this case, the extension portion 91 is provided integrally with the partition portion 12 and forms a part of the partition portion 12.

Modified Example of Seventh Construction

Figure 52:
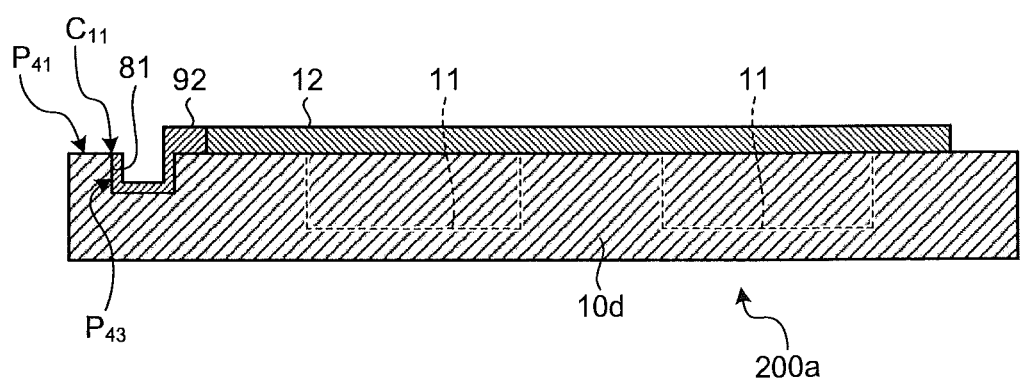
FIG. 52 is a cross-sectional view schematically illustrating an analysis chip according to Modified Example of the seventh construction.

FIG. 52 is a cross-sectional view schematically illustrating an analysis chip according to Modified Example of the seventh construction and a cross-sectional view corresponding to the cross section taken along the line D-D of FIG. 50. In the above-described seventh construction and, it has been described that the extension portion 91 is a part of the opening end of the recessed portion 81 and connects to a part of the side close to the partition portion 12. In the analysis chip according to Modified Example, however, the extension portion extends to the inside of the recessed portion 81. The analysis chip 200$a$ according to Modified Example of the seventh construction has a plurality of reaction portions 11 (six reaction portions in the seventh construction), a partition portion 12, a recessed portion 81, and an extension portion 92 being a connection portion and provided with a flat plate-like substrate 10$d$ the main surface of which forms a rectangular shape.

The extension portion 92 passes through a part of the side surface and a part of the bottom surface of the recessed portion 81 and connects to a part of a corner portion $C_{11}$ being a part of the opening end of the recessed portion 81 on the side far from the partition portion 12. The corner portion $C_{11}$ according to Modified Example is formed by the surface $P_{41}$ of the substrate 10$d$ and the side surface $P_{43}$ being the side surface of the recessed portion 81 far from the partition portion 12. The extension portion 92 extends from the partition portion 12 through the bottom surface of the recessed portion 81 to the corner portion $C_{11}$.

According to the modified example described above, sample contamination in the adjacent reaction portions 11 can be avoided and the unreacted labeled substance adhering to the water repellent surface can be efficiently washed off because the extension portion 92 forms a water repellent surface extending from a part of the partition portion 12 toward the outer edge (the edge side) of the substrate 10$d$ and extends to the corner portion $C_{11}$ formed by a part of the opening portion of the recessed portion 81 on the side far from the partition portion 12 and the surface of the substrate 10$d$. Generation of the background noise due to the unreacted labeled substance generated after washing can be reduced by this configuration.

Eighth Construction

Figure 53:
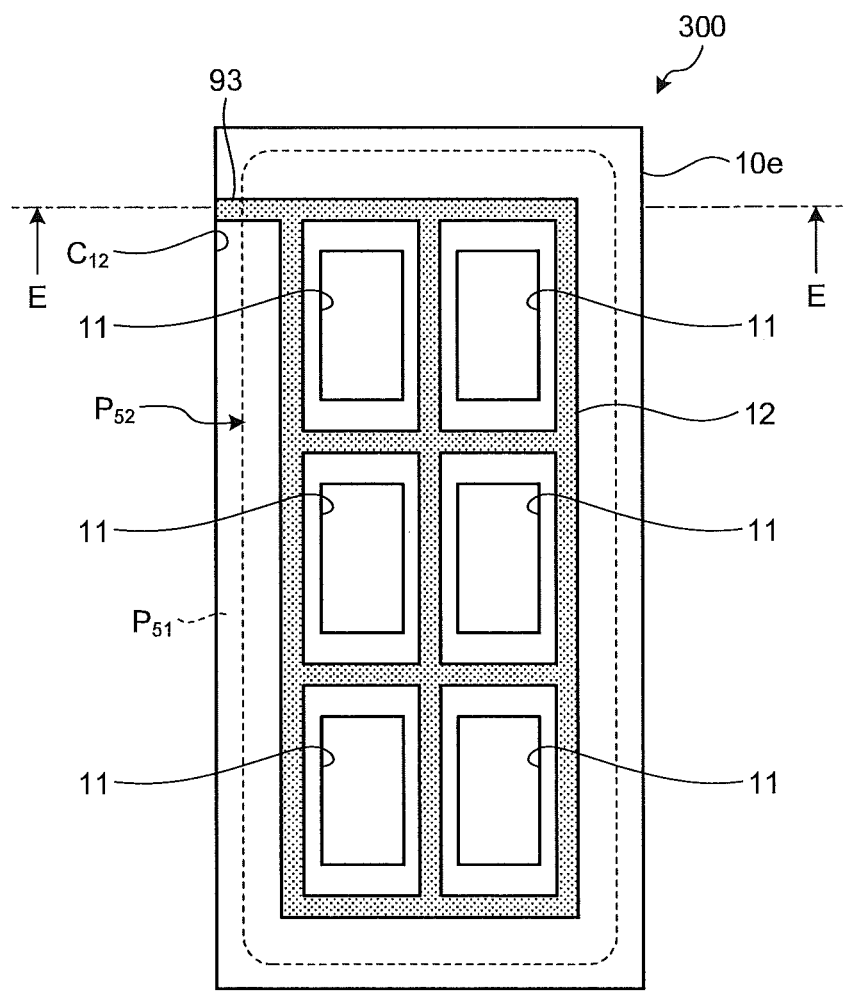
FIG. 53 is a plan view schematically illustrating an analysis chip according to an eighth construction.
Figure 54:
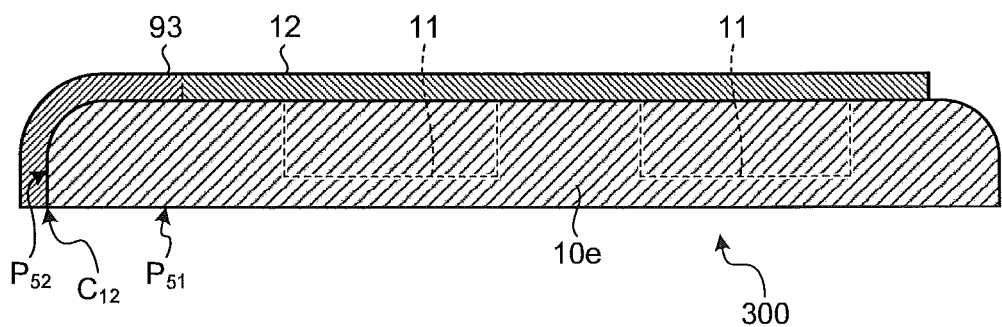
FIG. 54 is a cross-sectional view taken along the line E-E of FIG. 53.

FIG. 53 is a plan view schematically illustrating an analysis chip according to an eighth construction. FIG. 54 is a cross-sectional view corresponding to the cross-section taken along the line E-E of FIG. 53. In the above-described first to seventh constructions, it has been described that the substrate is a flat plate the main surface of which forms a rectangular shape. In an analysis chip according to the eighth construction, however, a coupling part between the main surface on one side of the substrate on which the reaction portions 11 are provided and the side surface continuous with the main surface is chamfered to form a curved surface.

An analysis chip 300 according to the eighth construction has a plurality of reaction portions 11, a partition portion 12, and an extension portion 93 being a connection portion and is provided with a flat plate-like substrate 10$e$ the main surface of which forms a rectangular shape. One end of the extension portion 93 is connected to a partition portion 12 and the other end extends to a corner portion $C_{12}$ formed by a surface $P_{51}$ on the side of the substrate 10$e$ where the reaction portions 11 are not formed and a side surface $P_{52}$ continuous with the surface $P_{51}$.

According to the eighth construction described above, sample contamination in the adjacent reaction portions 11 can be avoided and the unreacted labeled substance adhering to the water repellent surface can be efficiently washed off because the extension portion 93 forms a water repellent surface extending from a part of the partition portion 12 toward the outer edge (the edge side) of the substrate 10e and extends to the corner portion $C_{12}$ formed by the surface of the substrate 10e on the side where the reaction portions 11 are not formed and the side surface continuous with the surface. Generation of the background noise due to the unreacted labeled substance generated after washing can be reduced by this configuration.

Ninth Construction

Figure 55:
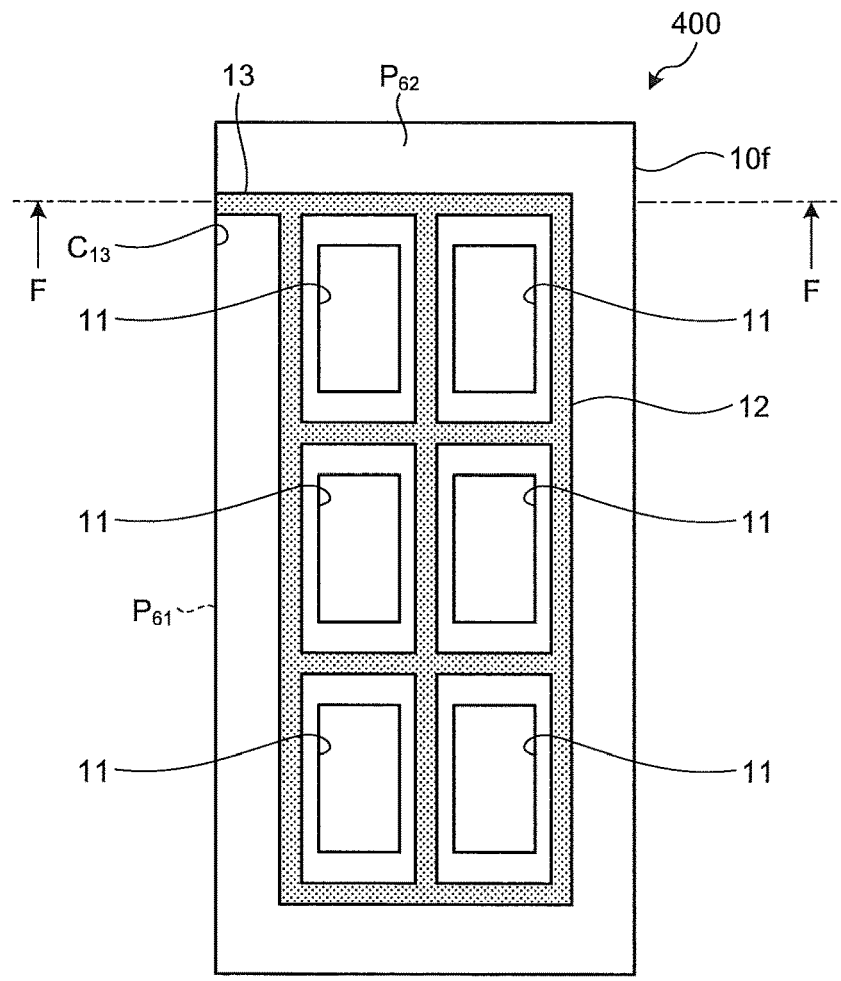
FIG. 55 is a plan view schematically illustrating an analysis chip according to a ninth construction.
Figure 56:
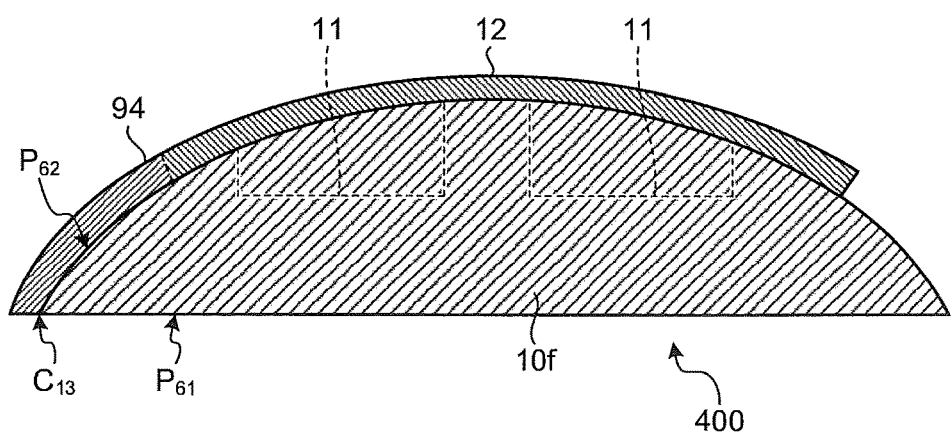
FIG. 56 is a cross-sectional view taken along the line F-F of FIG. 55.

FIG. 55 is a plan view schematically illustrating an analysis chip according to a ninth construction. FIG. 56 is a cross-sectional view corresponding to the cross section taken along the line F-F of FIG. 55. In the above-described first to eighth constructions, it has been described that the surface on which the reaction portions 11 are formed among the surfaces of the substrate forms a flat surface. In an analysis chip according to the ninth construction, the main surface being one main surface of the substrate on the side where the reaction portions 11 are provided forms a curved surface.

The analysis chip 400 according to the ninth construction has a plurality of reaction portions 11, a partition portion 12, and an extension portion 94 being a connection portion, and provided with a substrate 10f having one main surface on the side where the reaction portions 11 are provided forming a curved surface and the other main surface forming a flat surface continuous with one main surface. One end of the extension portion 94 is connected to the partition portion 12 and the other end extends to a corner portion $C_{13}$ formed by one main surface $P_{61}$ and the other main surface $P_{62}$. It is assumed that the main surface $P_{61}$ forms a flat surface and the main surface $P_{62}$ forms a curved surface. In other words, in the cross section of the substrate 10f passing through the main surface $P_{61}$ and the main surface $P_{62}$, the main surface $P_{61}$ is linear and the main surface $P_{62}$ is curved.

According to the eighth construction described above, sample contamination in the adjacent reaction portions 11 can be avoided and the unreacted labeled substance adhering to the water repellent surface can be efficiently washed off because the extension portion 94 forms a water repellent surface extending from a part of the partition portion 12 toward the outer edge (the edge side) of the substrate 10f and extends to the corner portion $C_{13}$ formed by one main surface and the other main surface of the substrate 10f. Generation of the background noise due to the unreacted labeled substance generated after washing can be reduced by this configuration.

In addition to the above-described first to ninth constructions and Modified Examples, an analysis chip having a connection portion connecting a corner portion intersecting different straight lines or curved lines from each other in a cross section in which a plane passing through the surface on which the reaction portions are provided is a cut surface and the partition portion partitioning the reaction portions can have the above-described effect.

EXAMPLES

Hereinafter, our chips will be further described in detail with reference to Examples. This disclosure, however, is not construed as being limited by these Examples.

Reference Example 1

Preparation of Substrate of Analysis Chip

Two kinds of molds for injection molding were produced using the Lithographie Galvanoformung Abformung (LIGA) process being a known method and substrates made of polymethyl methacrylate (PMMA) having shapes as described below were obtained by an injection molding method. The average molecular weight of PMMA used was 50,000 and carbon black (#3050B, manufactured by Mitsubishi Chemical Corporation) was contained in PMMA in a ratio of 1% by weight to make the substrate black. When the spectral reflectance and the spectral transmittance of this black substrate were measured, the spectral reflectance was 5% or less at any wavelength in a visible light region (wavelength is from 400 nm to 800 nm) and the transmittance was 0.5% or less at the wavelength in the same range. Neither the spectral reflectance nor the spectral transmittance had specific spectral patterns (peaks and the like) in the visible light region and the spectra were uniformly flat. The spectral reflectance was determined by using the device (CM-2002, manufactured by Minolta Camera Co., Ltd.) equipped with an illumination/light receiving optical system conforming to Condition C of JIS Z 8722 when specular reflection light from the substrate was taken.

The substrate having an outer shape of 75.0 mm in length, 25.4 mm in width, and 1.0 mm in thickness was produced by injection molding using the above molds. On the substrate, 24 rectangular and recessed reaction portions having a long side of 7.20 mm, a short side of 2.70 mm, and a depth of 0.12 mm were provided and 300 protrusion portions having a diameter of 0.1 mm and a height of 0.05 mm were provided in each of the reaction portions. The pitch of the protrusion portions was 0.17 mm The substrate was immersed into a 10 N sodium hydroxide aqueous solution at 70° C. for 12 hours. This substrate was washed with pure water, a 0.1 N HCl aqueous solution, and pure water in this order to generate carboxy groups on the surface of the substrates. The resulting substrate was used as the substrates for analysis chips.

Immobilization of Selective Binding Substance

A selective binding substance was immobilized on the reaction portions of the analysis chip by the following method. As the selective binding substance, a substance synthesized by modifying an amino group at the 5' end of an oligonucleotide indicating a sequence complementary to the sequences of several hundred kinds of human microRNAs was used. This oligonucleotide was dissolved in pure water to be a concentration of 0.3 nmol/µL to prepare a stock solution. When this stock solution is spotted on the substrate, the stock solution was diluted ten times with PBS (a solution prepared by dissolving in combination of 8 g of NaCl, 2.9 g of $Na_2HPO_4 \cdot 12H_2O$, 0.2 g of KCl, and 0.2 g of $KH_2PO_4$ in pure water, adjusting the volume to 1 L, and then adjusting the pH to 5.5 by adding hydrochloric acid) to set the final concentration of the probe DNA to 0.03 nmol/µL. 1-ethyl-3-(3-dimethyl aminopropyl)carbodiimide (EDC) was added for condensing the carboxy group formed on the surface of the PMMA substrate with the terminal amino group of the probe DNA to obtain a final concentration of 50 mg/mL. This solution was spotted on 22 protrusion portions using an arrayer (spotter) ("Gene Stamp-II" manufactured by Japan Laser Electronics Co., Ltd.). Subsequently, each spotted substrate was placed in a sealed plastic container and incubated under conditions of a humidity of 100% at 37° C. for about 20 hours. Finally, the substrate was washed with pure water, centrifuged with a spin dryer to dry.

Reference Example 2

Preparation of Sample Plate

BASE and CATALYST of DOW CORNING (registered trademark) SH 9555 W/C-K (manufactured by Dow Corning Toray Co., Ltd.) were kneaded at a ratio of 10:1 and the mixture was defoamed under vacuum. Thereafter, the defoamed mixture was poured into each of the molds having the outer shape of a length of 75.0 mm, a width of 23.4 mm, and a thickness of 2.0 mm and allowed to stand overnight at room temperature. On the sample plate, 24 rectangular recess-shaped wells having a long side of 7.80 mm, a short side of 3.30 mm, and a depth of 0.50 mm were provided. After curing, the sample plate was removed from the mold to obtain a molded article.

Example 1

Figure 57:
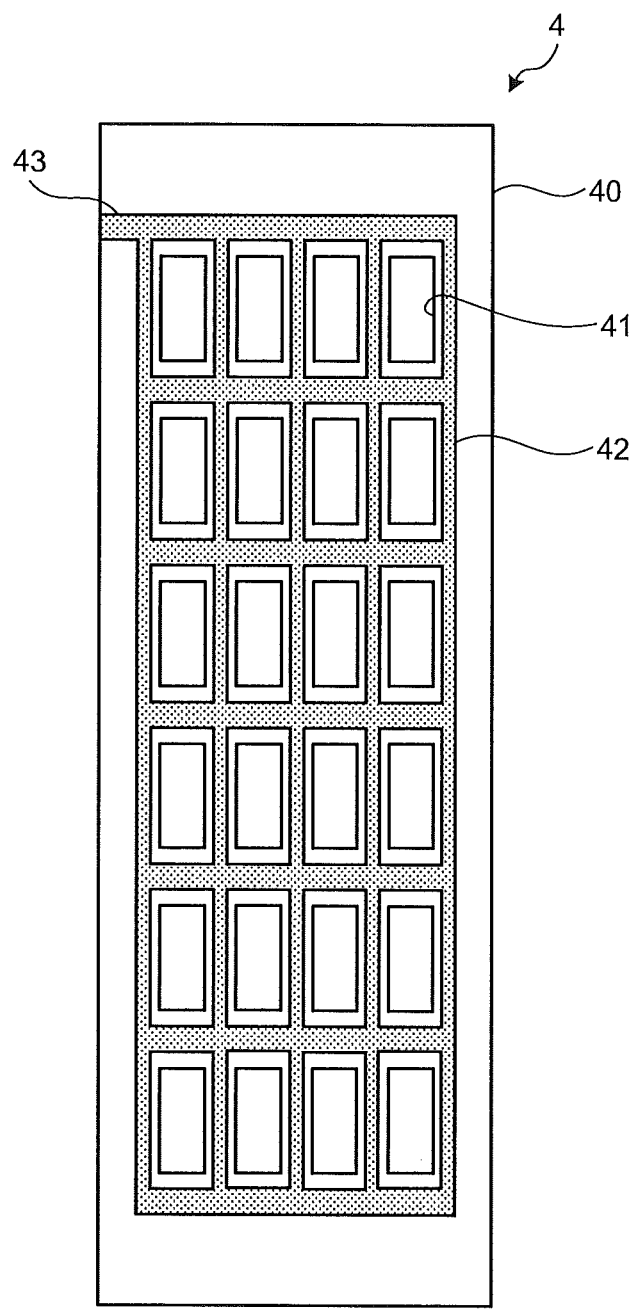
FIG. 57 is a plan view schematically illustrating an analysis chip used as an Example.

The outer periphery of the reaction portions of the analysis chip prepared in Reference Example 1 was coated with the fluorine-based water repellent material FS-1010C (manufactured by Fluoro Technology Co., Ltd.) to partition the reaction portions, whereby an analysis chip in which a part of the continuous water repellent surface was in contact with a part of the edge side on the surface was prepared. FIG. 57 is a plan view schematically illustrating an analysis chip used as this Example. The analysis chip 4 includes a substrate 40 having 24 reaction portions 41, a partition portion 42 surrounding and partitioning the reaction portions 41, and an extension portion 43 connecting the partition portion 42 and the substrate 40. The following operation was carried out using the analysis chip 4.

Sample Preparation/Fluorescent Label

Human Prostate total RNA (Thermo Fisher Scientific Inc. (registered trademark)) was used as the sample and adjusted to be 250 ng/μL with sterilized purified water. This solution was dephosphorylated by alkaline phosphatase treatment and thereafter a labeling dye (Cy5) was added using a ligation enzyme. Subsequently, the resultant solution was diluted with 1× hybridization solution (1% by weight bovine serum albumin (BSA), 5×SSC, 1% by weight sodium dodecyl sulfate (SDS), 50 ng/mL salmon sperm DNA solution, 5% by weight dextran sodium sulfate, and 30% formamide) so that the nucleic acid concentration was 1 amol/μL, and used as the sample.

Hybridization Process

14 μL of the sample was dropped to 6 wells out of 24 wells provided in the sample plate prepared in Reference Example 2 and the analysis chip and the sample plate were stacked so that the reaction portions of the analysis chip and the wells of the sample plate corresponded to each other. At this time, the reaction portions of the analysis chip were stacked from the top of the sample plate in a direction where the reaction portions faced downward and fixed (refer to, for example, FIG. 3). Subsequently, the stacked analysis chip was set to a stirring device (rotating radius 2 mm, number of rotation 2130 rpm) placed in an oven controlled at 32° C. and stirred for 3 hours.

Washing Process

After the completion of the hybridization, the analysis chip was washed using a 1100 mL capacity of stainless square pot (washing container/manufactured by SANSYO Co. Ltd.) according to the following procedure. In Washing Process 1, the analysis chip was entirely immersed into Washing Liquid 1 (0.5×SSC, 0.1% by weight SDS) and thereafter the analysis chip was entirely pulled up from the liquid into the air. This operation was repeated and subsequently the analysis chip was reciprocated several times from the left to the right in the liquid. In Washing Process 2, the analysis chip was entirely immersed into Washing Liquid 2 (0.5×SSC, 0.1% by weight SDS) and moved up and down 15 times in the liquid. This movement was carried out 5 times at 1 minute intervals. In Washing Process 3, the analysis chip was entirely immersed into Washing Liquid 3 (0.2×SSC, 0.1% by weight SDS) and moved up and down 15 times in the liquid. This movement was carried out 10 times at 1 minute intervals. In Washing Process 4, the analysis chip was entirely immersed into Washing Liquid 4 (0.05×SSC) and moved up and down 15 times in the liquid. This movement was carried out 1 time. In Washing Process 5, the analysis chip was entirely immersed into Washing Liquid 5 (0.05×SSC) and moved up and down 15 times in the liquid. This movement was carried out 5 times at 1 minute intervals. Between each Washing Process, the analysis chip was completely taken out into the air and the liquid was allowed to run out. After completion of Washing Process 5, the analysis chip was pulled up from the liquid such that the water repellent surface in contact with the edge side of the analysis chip was finally pulled up from the washing liquid and the remaining liquid was allowed to run out on paper towel.

Drying Process

After completion of the washing process, the analysis chip was centrifugally dried using a centrifuge spin dryer mini for slide glasses (manufactured by WAKENBTECH CO, LTD) for 1 minute.

Evaluation of Fluorescence Signal on Water Repellent Surface

With respect to the analysis chip after the drying process, the fluorescent dye attached to the water repellent surface was evaluated by using the high resolution fluorescence detection apparatus ("3D-Gene (registered trademark) Scanner" manufactured by Toray Industries, Inc.) by reading the image under conditions of a laser intensity of 100%, a focus of 0 μm, and a PhotoMultiplier Tube (PMT) of 38. At this time, the signal intensities obtained in any 10 points on the water repellent surface are listed in Table 1. The signal intensities indicated low values of 61 to 92 and the variation was also small.

TABLE 1

| | Arbitrary position on water repellent surface | | | | | | | | | |
|---|---|---|---|---|---|---|---|---|---|---|
| | 1 | 2 | 3 | 4 | 5 | 6 | 7 | 8 | 9 | 10 |
| Example 1 | 81 | 61 | 65 | 64 | 70 | 91 | 87 | 83 | 92 | 84 |

Comparative Example 1

Figure 58:
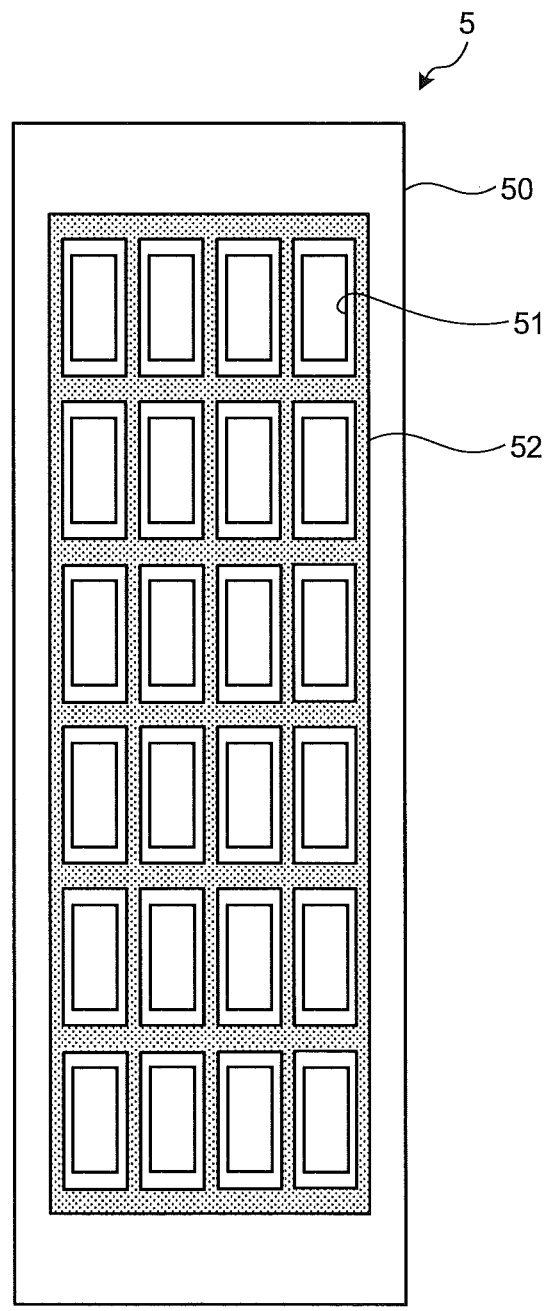
FIG. 58 is a plan view schematically illustrating an analysis chip used as a Comparative Example.

The outer periphery of the reaction portions alone of the analysis chip prepared in Reference Example 1 was coated with the fluorine-based water repellent material FS-1010C (manufactured by Fluoro Technology Co., Ltd.), whereby an analysis chip in which the reaction portions were partitioned by the water repellent surface was prepared. FIG. 58 is a plan view schematically illustrating an analysis chip used as this Comparative Example. The analysis chip 5 includes a substrate 50 having 24 reaction portions 51 and a partition portion 52 surrounding and partitioning the reaction portions 51. In the analysis chip 5, no extension portion is formed. The analysis chip 5 was used and set with the sample plate similar to Example 1. Each of the processes of sample preparation/fluorescent label, hybridization, washing, and drying was carried out. Thereafter, the image was read by using 3D-Gene (registered trademark) Scanner under conditions of a laser intensity of 100%, a focus of 0 μm, and a PMT of 38. Similar to Example 1, the signal intensities obtained in any 10 points on the water repellent surface are listed in Table 2. The signal intensities were 1170 to 8400, which were larger than those of Example 1 and the variation was also large. The numbers at arbitrary positions on the water repellent surface in Comparative Example 1 and the respective numbers in arbitrary positions in Example 1 are relatively the same positions (coordinates) on the substrate surface.

TABLE 2

| | Arbitrary position on water repellent surface | | | | | | | | | |
|---|---|---|---|---|---|---|---|---|---|---|
| | 1 | 2 | 3 | 4 | 5 | 6 | 7 | 8 | 9 | 10 |
| Comparative Example 1 | 8390 | 7320 | 8400 | 8360 | 1470 | 1780 | 1170 | 2300 | 8290 | 6380 |

Example 2

Each of the processes of sample preparation/fluorescent label, hybridization, washing, and drying was carried out using an analysis chip similar to the analysis chip in Example 1. The signals were detected with 3D-Gene (registered trademark) Scanner. In the hybridization process, the sample was reacted using six reaction portions out of the 24 reaction portions of the analysis chip. For the six reaction portions used, each of the signal intensities of the spots to which the selective binding substance was immobilized and the signal intensity of the blank was read and the S/N ratio was calculated. The results are listed in Table 3. The value of low-signal microRNA (hsa-miR-663b) was evaluated as the substance to be examined. All of the S/N ratios were 2 or more and thus accurate values were detected without the effect of noise. In addition, the coefficient of variation: standard deviation/average (CV) of the signal intensities of the microRNA among the six reaction portions was 5% and the CV of the blank signal intensity was 1%, both of which indicated small variations.

TABLE 3

| | Reaction portion | | | | | |
|---|---|---|---|---|---|---|
| | No. 1 | No. 2 | No. 3 | No. 4 | No. 5 | No. 6 |
| Signal (hsa-miR-663b) | 107 | 99 | 108 | 97 | 94 | 101 |
| Noise (Blank) | 41 | 40 | 40 | 40 | 40 | 40 |
| S/N ratio | 2.6 | 2.5 | 2.7 | 2.4 | 2.3 | 2.5 |

Comparative Example 2

Similar to Example 2, each of the processes of sample preparation/fluorescent label, hybridization, washing, and drying was carried out using an analysis chip similar to the analysis chip in Comparative Example 1. The signals were detected with 3D-Gene (registered trademark) Scanner. In the hybridization process, the sample was reacted using six reaction portions out of the 24 reaction portions of the analysis chip. For the six reaction portions used, each of the signal intensities of the spots to which the selective binding substance was immobilized and the signal intensity of the blank was read and the S/N ratio was calculated. The results are listed in Table 4. The value of low-signal microRNA (hsa-miR-663b) was evaluated as the substance to be examined. All of the S/N ratios were 2 or less and thus the signals could not be correctly detected. In addition, both of CVs of the signal intensities of the microRNA among the six reaction portions and the blank signal intensity were 17%, both of which indicated large variations. This is probably because unreacted labeled dye nonspecifically adheres not only to the blank in the reaction portion but also to the selective binding substance, which affected the data.

TABLE 4

| | Reaction portion | | | | | |
|---|---|---|---|---|---|---|
| | No. 1 | No. 2 | No. 3 | No. 4 | No. 5 | No. 6 |
| Signal (hsa-miR-663b) | 84 | 116 | 131 | 143 | 137 | 122 |
| Noise (Blank) | 68 | 83 | 70 | 98 | 77 | 63 |
| S/N ratio | 1.2 | 1.4 | 1.9 | 1.5 | 1.8 | 1.9 |

Example 3

Using a similar analysis chip to the analysis chip in Example 1, the remaining amount of the solution in the reaction portion was measured when the analysis chip was pulled out of the washing liquid from the state of being entirely immersed in the washing liquid. As the washing liquid, Washing Liquid 1 (0.5×SSC, 0.1% by weight SDS) used in the washing process was used. When the analysis chip was pulled up from the washing liquid, it was pulled up from the washing liquid such that the water repellent surface in contact with the edge side of the analysis chip was finally pulled up from the washing liquid. After placing the analysis chip on an experiment table, the amount of liquid in the reaction portion was measured for any four portions using a micropipette. The results are listed in Table 5. The amounts of liquid in the four reaction portions were 1.02 μL to 1.20 μL and the CV was 7%, which indicated the small variation.

TABLE 5

| | Remaining amount in reaction portion (μL) | | | | |
|---|---|---|---|---|---|
| | No. 1 | No. 2 | No. 3 | No. 4 | CV (%) |
| Example 3 | 1.20 | 1.10 | 1.12 | 1.02 | 7 |

Comparative Example 3

A sheet-like water repellent material (Nitoflon No. 903UL/No. 9030UL (manufactured by NITTO DENKO CORPORATION)) having a thickness of 70 μm was attached to the analysis chip prepared as in the case of Reference Example 1 to partition the reaction portions. At this time, the sheet-like water repellent material was applied so that a part of the continuous water repellent surface was in contact with a part of the edge side on the surface of the analysis chip. Similar to Example 3, using this analysis chip, the remaining amount of the solution in the reaction portion was measured when the analysis chip was pulled out of the washing liquid from the state of being entirely immersed in the washing liquid. As the washing liquid, Washing Liquid 1 (0.5×SSC, 0.1% by weight SDS) used in the washing process was used. When the analysis chip was pulled up from the washing liquid, it was pulled up from the washing liquid such that the water repellent surface in contact with the edge side of the analysis chip was finally pulled up from the washing liquid. After placing the analysis chip on an experiment table, the amount of liquid in the reaction portion was measured for any four portions using a micropipette. The results are listed in Table 6. The amounts of liquid in the four reaction portions were 1.48 µL to 2.52 µL, which indicated larger values than the values of Example 3, and the CV was 25%, which also indicated the larger variation. This was probably because the thickness of the water repellent surface increased due to forming the water repellent surface in the form of a sheet and a large contact angle was formed so that the water repellent action started regardless of the pulling direction and a large amount of solution flowed nonuniformly into the reaction portions.

TABLE 6

| | Remaining amount in reaction portion (µL) | | | | |
|---|---|---|---|---|---|
| | No. 1 | No. 2 | No. 3 | No. 4 | CV (%) |
| Comparative Example 3 | 1.66 | 2.30 | 2.52 | 1.48 | 25 |

The analysis chip does not leave any unreacted labeled substance on the water repellent surface of the outer periphery of the reaction portion and reduces background noise, and thus enables the substance to be examined to be accurately detected or quantified. Therefore, our chip allows diseases to be diagnosed and examined by measuring markers of genes, proteins, and the like at clinical sites and inspection centers. Therefore, our chips are remarkably industrially useful.

Example 4

Each analysis chip was prepared by applying the fluorine-based water repellent material FS-1010C (manufactured by Fluoro Technology Co., LTD.) onto the outer periphery of the reaction portions of the analysis chip prepared in Reference Example 1 to partition the reaction portions, forming an extension portion extending from a part toward the outer edge, and thereafter attaching 1 to 10 water repellent tape(s) of 12 mm×6 mm and 60 µm in thickness to form a projection portion. Specifically, the projection portion 72 of the analysis chip 100c illustrated in FIG. 32 was made of a water repellent tape. The following operation was carried out using these analysis chips. In addition, an analysis chip having the partition portion alone without attaching the tape was also prepared for comparison.

Measurement of Time Period for the Liquid to Run Out

After Washing Processes 1 to 5 described above were carried out and Washing Process 5 was completed, the analysis chip was pulled up from the washing liquid such that the projection portion, among the reaction portion, the partition portion, the extension portion, and the projection portion, of the analysis chip was finally pulled up, and the liquid was allowed to run out on a paper towel. The time period for the liquid to run out was measured. As the time period for the liquid to run out, the period from when the analysis chip was pulled up until the liquid disappeared on the water repellent surface was measured. In Table 7, measurement results of the time period for the liquid to run out for each number of laminated tapes are listed.

TABLE 7

| | Number of laminated tapes | | | | | | | | | | |
|---|---|---|---|---|---|---|---|---|---|---|---|
| | 0 | 1 | 2 | 3 | 4 | 5 | 6 | 7 | 8 | 9 | 10 |
| Time for the liquid to run out (Second) | — | 20 | 45 | 9 | 11 | 11 | 10 | 5 | 4 | 7 | 5 |

As shown in Table 7, in the analysis chip to which no tape was attached, that is, the analysis chip having no projection portions, the liquid did not run out and thus the time period for the liquid to run out was impossible to be measured. In contrast, we found that the liquid run out by laminating the tapes and, when the three or more layers of the tapes are laminated, the liquid run out about 10 seconds.

The analysis chip does not leave any unreacted labeled substance on the water repellent surface of the outer periphery of the reaction portion and reduces the generation of background noise, and thus enables the substance to be examined to be accurately detected or quantified. Therefore, our chips allow diseases to be diagnosed and examined by measuring markers of genes, proteins and the like at clinical sites and inspection centers and enables to obtain highly reliable data. Therefore, our chips are remarkably industrially useful.

INDUSTRIAL APPLICABILITY

The analysis chip can be suitably employed to reduce the generation of background noises generated after washing.

The invention claimed is:
1. An analysis chip comprising:
 a substrate main body having a plurality of reaction portions in which a selective binding substance selectively binding to a substance to be examined is immobilized;
 a corner portion provided on or above a surface of the substrate main body on which the reaction portions are provided;
 a partition portion formed by applying water repellent treatment to the surface of the substrate main body on which the reaction portions are provided, the partition portion being configured to partition the reaction portions inside an outer edge formed by the surface, and
 a connection portion having water repellency, the connection portion configured to connect between a part of the partition portion and the corner portion,
 wherein a water repellent surface of the partition portion and the connection portion is only formed on a part of the surface of the substrate main body.
2. The analysis chip according to claim 1, wherein
 the corner portion is the outer edge of the surface of the substrate main body, and
 the connection portion has one extension portion or a plurality of extension portions extending from a part of the partition portion to at least a part of the corner portion.
3. The analysis chip according to claim 2, wherein
 the substrate main body has a rectangular shape formed by the outer edge, and
 the extension portion is in contact with a part of one edge side out of four sides of the outer edge.

4. The analysis chip according to claim 2, wherein
the substrate main body has a rectangular shape formed by the outer edge, and
the plurality of extension portions are in contact with a part of different edge sides from each other out of four edge sides of the outer edge.

5. The analysis chip according to claim 2, further comprising an indicator portion indicating a position of the one extension portion.

6. The analysis chip according to claim 2, wherein the connection portion is a cutout portion being a part of the substrate main body, formed by cutting out a region from the outer edge of the substrate main body to the partition portion, and having the corner portion.

7. The analysis chip according to claim 1, further comprising a projection portion connected to a water repellent surface of the partition portion, the projection portion being configured to project from the substrate main body, wherein,
the corner portion is formed from a side surface along a projecting direction of the projecting portion by at least a top surface of the projection portion in the projecting direction and the side surface, the side surface being connected to the partition portion; and
a projecting length of the top surface of the projection portion from the substrate main body is longer than a protruding length of the water repellent surface of the partition portion from the substrate main body.

8. The analysis chip according to claim 7, wherein
the connection portion has one extension portion or a plurality of extension portions extending from a part of the partition portion toward the outer edge of the substrate main body, and connected to the corner portion at an end portion of the projection portion opposite to an end portion of the projection portion connected to the partition portion; and
the projection portion is connected to the water repellent surface of the partition portion via the extension portion and includes one or more projection portions depending on number of the extension portion(s).

9. The analysis chip according to claim 7, wherein the projection portion is provided adjacent to a part of the partition portion.

10. The analysis chip according to claim 9, wherein
the partition portion has a rectangular shape formed by the outer edge;
the projection portion is in contact with a linear portion in the outer edge; and
the connection portion is integrally provided with the projection portion.

11. The analysis chip according to claim 9, wherein
the partition portion has a rectangular shape formed by the outer edge;
the projection portion is in contact with a corner portion in the outer edge; and
the connection portion is integrally provided with the projection portion.

12. The analysis chip according to claim 7, wherein the projection portion comprises a sheet-like member.

13. The analysis chip according to claim 7, wherein the projection portion is integrally formed with the substrate main body.

14. The analysis chip according to claim 1, further comprising a recessed portion having one end connected to a water repellent surface of the partition portion and having a recessed shape with respect to the surface of the substrate main body, wherein
the corner portion is formed by an end of an opening of the recessed portion.

15. The analysis chip according to claim 14, wherein
the connection portion has one extension portion or a plurality of extension portions extending from a part of the partition portion toward the outer edge of the substrate main body, and connected to a part of the opening of the recessed portion at an end portion of the recessed portion opposite to an end portion of the recessed portion connected to the partition portion; and
the recessed portion is connected to the water repellent surface of the partition portion via the extension portion and includes one or more recessed portions depending on number of the extension portion(s).

16. The analysis chip according to claim 15, wherein the extension portion is connected to the water repellent surface of the partition portion and includes a water repellent surface extending from a part of a side that is a side surface of the recessed portion along a depression direction of the recessed portion and that is connected to the partition portion to a part of a side surface of the recessed portion different from the side via a bottom surface of the recessed portion in the depression direction of the recessed portion.

17. The analysis chip according to claim 16, wherein the extension portion is configured to form a part of the partition portion.

18. The analysis chip according to claim 1, wherein the partition portion is configured to independently partition each of the reaction portions.

19. The analysis chip according to claim 1, wherein the partition portion is configured to partition the reaction portions as each set of a plurality of reaction portions.

20. The analysis chip according to claim 1, wherein the reaction portion has a recessed shape with respect to the surface of the substrate main body.

* * * * *